(12) United States Patent
Kalyanaraman et al.

(10) Patent No.: US 11,612,610 B2
(45) Date of Patent: Mar. 28, 2023

(54) MITO-MAGNOLOL COMPOUNDS AND METHODS OF SYNTHESIS AND USE THEREOF

(71) Applicants: The Medical College of Wisconsin, Inc., Milwaukee, WI (US); AIX-MARSEILLE UNIVERSITE, Marseilles (FR)

(72) Inventors: Balaraman Kalyanaraman, Milwaukee, WI (US); Jacek Michal Zielonka, Wauwatosa, WI (US); Gang Cheng, Milwaukee, WI (US); Micael Joël Hardy, Nîmes (FR); Olivier Ouari, Marseilles (FR)

(73) Assignees: Medical College of Wisconsin, Inc., Milwaukee, WI (US); Aix-Marseille Universite, Marseilles (FR)

( * ) Notice: Subject to any disclaimer, the term of this patent is extended or adjusted under 35 U.S.C. 154(b) by 0 days.

(21) Appl. No.: 17/397,672

(22) Filed: Aug. 9, 2021

(65) Prior Publication Data
US 2022/0211727 A1 Jul. 7, 2022

Related U.S. Application Data

(63) Continuation of application No. 16/714,461, filed on Dec. 13, 2019, now Pat. No. 11,083,739.

(60) Provisional application No. 62/779,795, filed on Dec. 14, 2018.

(51) Int. Cl.
| | | |
|---|---|---|
| C07F 9/54 | (2006.01) | |
| A61K 31/66 | (2006.01) | |
| A61P 35/00 | (2006.01) | |
| A61K 45/06 | (2006.01) | |

(52) U.S. Cl.
CPC .............. *A61K 31/66* (2013.01); *A61K 45/06* (2013.01); *A61P 35/00* (2018.01); *C07F 9/54* (2013.01)

(58) Field of Classification Search
CPC ....................................................... C07F 9/54
See application file for complete search history.

(56) References Cited

PUBLICATIONS

Sarrica et al., 2018. Safety and Toxicology of Magnolol and Honokiol. Planta Med 84: 1151-64.
Schlie et al., 2015. Survival of effector CD8+ T cells during influenza infection is dependent on autophagy. J Immunol 194: 4277-86.
Schockel et al., 2015. Targeting mitochondrial complex I using BAY 87-2243 reduces melanoma tumor growth. Cancer Metab 3:11.
Sena et al., 2013. Mitochondria are required for antigen-specific T cell activation through reactive oxygen species signaling. Immunity 38: 225-36.
Smith et al., 2008. Mitochondria-targeted antioxidants in the treatment of disease. Ann. N. Y. Acad. Sci 1147: 105-11.
Spoerri et al., 2017. Real-Time Cell Cycle Imaging in a 3D Cell Culture Model of Melanoma. Methods Mol Biol 1612 401-16.
Sukumar et al., 2016. Mitochondrial Membrane Potential Identifies Cells with Enhanced Sternness for Cellular Therapy. Cell Metab 23: 63-76.
Sun et al., 2017. A fluorescence-based imaging method to measure in vitro and in vivo mitophagy using mt-Keima. Nat Protoc 12:1576-87.
Tan et al., The Role of PGC1α in Cancer Metabolism and its Therapeutic Implications. Mol Cancer Ther. May 2016;15(5):774-82.
Tian et al., Magnolol Alleviates Inflammatory Responses and Lipid Accumulation by AMP-Activated Protein Kinase-Dependent Peroxisome Proliferator-Activated Receptor α Activation. Front Immunol. Feb. 5, 2018;9:147. doi: 10.3389/fimmu.2018.00147. eCollection 2018.
Titova et al., 2018. Mitochondria-targeted antioxidant SkQ1 suppresses fibrosarcoma and rhabdomyosarcoma tumour cell growth. Cell Cycle 17: 1797-811.
Tsai et al., 2018. Development of primary human pancreatic cancer organoids, matched stromal and immune cells and 3D tumor microenvironment models. BMC Cancer 18: 335.
Tsao et al., 2004. Genetic interaction between NRAS and BRAF mutations and PTEN/MMAC1 inactivation in melanoma. J Invest Dermatol 122:337-41.
Van de Bittner et al., 2010. In vivo imaging of hydrogen peroxide production in a murine tumor model with a chemoselective bioluminescent reporter. Proc Natl Acad Sci U S A 107: 21316-21.
Vander Heiden et al., 2017. Understanding the Intersections between Metabolism and Cancer Biology. Cell 168: 657-69.
Vazquez et al., PGC1α expression defines a subset of human melanoma tumors with increased mitochondrial capacity and resistance to oxidative stress. Cancer Cell Mar. 18, 2018;23(3):287-301.
Vellinga et al., SIRT1/PGC1α-Dependent Increase in Oxidative Phosphorylation Supports Chemotherapy Resistance of Colon Cancer Clin Cancer Res. Jun. 15, 2015;21(12):2870-9.
Wang et al., 1998. Chemokines and their role in tumor growth and metastasis. J. Immunol. Methods 220: 1-17.
Weinberg et al., Mitochondrial metabolism and ROS generation are essential for Kras-mediated tumorigenicity. Proc Natl Acad Sci U S A. May 11, 2010;107(19):8788-93.
Weinberg et al., 2015. Targeting mitochondria metabolism for cancer therapy. Nat Chem Biol 11:9-15.
Weinberg et al., 2015. Mitochondria in the regulation of innate and adaptive immunity. Immunity 42: 406-17.
Wendt et al., 2008. Epigenetic silencing of CXCL12 increases the metastatic potential of mammary carcinoma cells. Oncogene 27:1461-71.
Wendt et al., 2008. Constitutive CXCL12 expression induces anoikis in colorectal carcinoma cells. Gastroenterology 135: 508-17.
Wood et al., 2003. Peroxiredoxin evolution and the regulation of hydrogen peroxide signaling. Science 300: 650-3.

(Continued)

*Primary Examiner* — Shawquia Jackson
(74) *Attorney, Agent, or Firm* — Quarles & Brady LLP

(57) ABSTRACT

The present invention provides mito-magnolol compounds, pharmaceutical compositions thereof, and methods of using the mito-magnolol compounds in the treatment of cancer, especially anti-cancer therapy or kinase resistant cancers.

18 Claims, 17 Drawing Sheets

(56) References Cited

PUBLICATIONS

Zha et al., 2004. Negative regulation of T-cell function by PD-1. Crit Rev Immunol 24: 229-37.

Ziegler et al., 2018. Mitophagy in Intestinal Epithelial Cells Triggers Adaptive Immunity during Tumorigenesis. Cell 174: 88-101.e16.

Zielonka et al., Mitochondria-Targeted Triphenylphosphonium-Based Compounds: Syntheses, Mechanisms of Action, and Therapeutic and Diagnostic Applications. Chem Rev. Aug. 9, 2017;117(15):10043-120.

Zielonka et al., 2018. Small-molecule luminescent probes for the detection of cellular oxidizing and nitrating species. Free Radic Biol Med 128: 3-22.

Zielonka et al., 2016. On the use of peroxy-caged luciferin (PCL-1) probe for bioluminescent detection of inflammatory oxidants in vitro and in vivo—Identification of reaction intermediates and oxidant-specific minor products. Free Radic Biol Med 99: 32-42.

Zimmerman et al., 2011. Targeted intestinal epithelial deletion of the chemokine receptor CXCR4 reveals important roles for extracellular-regulated kinase—1/2 in restitution. Lab Invest 91: 1040-55.

Dancerand Metastasis Reviews (1998), 17(1), 91-106.

Science (1999), vol. 286, 531-537.

Dancer [online], [retrieved on Jul. 6, 2007. Retrieved from the internet, URL http://www.nim.nih.gov/medlineplus/cancer.html>.

Abildgaard et al., 2014. Bioenergetic modulation with dichloroacetate reduces the growth of melanoma cells and potentiates their response to BRAFV600E inhibition. J Transl Med 12: 247.

Allavena et al., 2016. Suppressed translation and ULK1 degradation as potential mechanisms of autophagy limitation under prolonged starvation. Autophagy 12: 2085-97.

Andreyev et al., 2015. Mitochondrial ROS Metabolism: 10 Years Later. Biochemistry (Mosc) 80: 517-31.

Araki et al., 2009. mTOR regulates memory CD8 T-cell differentiation. Nature 460: 108-12.

Asin-Cayuela et al., Fine-tuning the hydrophobicity of a mitochondria-targeted antioxidant. FEBS Lett. Jul. 30, 2004;571(1-3):9-16.

Batus et al., 2013. Optimal management of metastatic melanoma: current strategies and future directions. Am J Clin Dermatol 14: 179-94.

Beier et al., 2015. Essential role of mitochondrial energy metabolism in Foxp3(+) T-regulatory cell function and allograft survival. Faseb j 29: 2315-26.

Bengsch et al., 2017. CTLA-4/CD80 pathway regulates T cell infiltration into pancreatic cancer. Cancer Immunol Immunother 66: 1609-17.

Bentolila et al., 2018. Intravital Imaging of Human Melanoma Cells in the Mouse Ear Skin by Two-Photon Excitation Microscopy. Methods Mol Biol 1755: 223-32.

Berridge et al., Effects of mitochondrial gene deletion on tumorigenicity of metastatic melanoma: reassessing the Warburg effect. Rejuvenation Res. Apr.-Jun. 2010;13(2-3):139-41.

Blank et al., 2006. Blockade of PD-L1 (B7-H1) augments human tumor-specific T cell responses in vitro. Int J Cancer 119: 317-27.

Boyle et al., 2018. Mitochondria-targeted drugs stimulate mitophagy and abrogate colon cancer cell proliferation. J Biol Chem 293: 14891-904.

Brahmer et al., 2010. Phase I study of single-agent anti-programmed death-1 (MDX-1106) in refractory solid tumors safety, clinical activity, pharmacodynamics, and immunologic correlates. J Clin Oncol 28: 3167-75.

Brandt et al., 2018. Augmentation of intracellular iron using iron sucrose enhances the toxicity of pharmacological ascorbate in colon cancer cells. Redox Biol 14: 82-7.

Brunen D, Bernards R. 2017. Drug therapy: Exploiting synthetic lethality to improve cancer therapy. Nat Rev Clin Oncol 14: 331-2.

Bryant et al., 2017. A Mitochondrial-targeted purine-based HSP90 antagonist for leukemia therapy. Oncotarget 8: 112184-98.

Buck et al., 2015. T cell metabolism drives immunity. J Exp Med 212: 1345-60.

Cha et al., 2018. Metformin Promotes Antitumor Immunity via Endoplasmic-Reticulum-Associated Degradation of PD-L1. Mol Cell 71: 606-20.e7.

Chamoto et al., Mitochondrial activation chemicals synergize with surface receptor PD-1 blockade for T cell-dependent antitumor activity. Proc Natl Acad Sci U S A. Jan. 31, 2017;114(5):E761-E70.

Chandran et al., 2009. Doxorubicin inactivates myocardial cytochrome c oxidase in rats: cardioprotection by Mito-Q. Biophys. J 96: 1388-98.

Chandrashekaran et al., 2017. HMGB1-RAGE pathway drives peroxynitrite signaling-induced IBD-like inflammation in murine nonalcoholic fatty liver disease. Redox Biol 13: 8-19.

Chen et al., 2013. Oncology meets immunology: the cancer-immunity cycle. Immunity 39: 1-10.

Chen et al., 2017. Elements of cancer immunity and the cancer-immune set point. Nature 541: 321-30.

Cheng et al., 2011. Mitochondria-targeted nitroxides exacerbate fluvastatin-mediated cytostatic and cytotoxic effects in breast cancer cells. Cancer Biol. Ther 12: 707-17.

Cheng et al., Mitochondria-targeted drugs synergize with 2-deoxyglucose to trigger breast cancer cell death. Cancer Res. May 15, 2012;72(10):2634-44.

Cheng et al., 2015. Antiproliferative effects of mitochondria-targeted cationic antioxidants and analogs: Role of mitochondrial bioenergetics and energy-sensing mechanism. Cancer Lett 365: 96-106.

Cheng et al., Profiling and targeting of cellular bioenergetics: inhibition of pancreatic cancer cell proliferation. Br J Cancer. Jul. 8, 2014;111(1):85-93.

Cheng et al., Mitochondria-targeted vitamin E analogs inhibit breast cancer cell energy metabolism and promote cell death. BMC Cancer Jun. 13, 2013;13:285.

Cheng et al., 2016. Mitochondria-Targeted Analogues of Metformin Exhibit Enhanced Antiproliferative and Radiosensitizing Effects in Pancreatic Cancer Cells. Cancer Res 76: 3904-15.

Cheng et al., 2018. Detection of mitochondria-generated reactive oxygen species in cells using multiple probes and methods: Potentials, pitfalls, and the future. J Biol Chem 293: 10363-80.

Chuang et al., Magnolia polyphenols attenuate oxidative and inflammatory responses in neurons and microglial cells. J Neuroinflammation. Jan. 29, 2013;10:15 doi: 10.1186/1742-2094-10-15.

Corazao-Rozas et al., Mitochondrial oxidative stress is the Achille's heel of melanoma cells resistant to Braf-mutant inhibitor. Oncotarget Nov. 2013;4(11):1986-98.

Cox et al., 2009. Mitochondrial peroxiredoxin involvement in antioxidant defence and redox signalling. Biochem J 425: 313-25.

Cunha et al., 2018. LC3-Associated Phagocytosis in Myeloid Cells Promotes Tumor Immune Tolerance. Cell 75: 429-41.

Das et al., 2015. NADPH Oxidase-Derived Peroxynitrite Drives Inflammation in Mice and Human Nonalcoholic Steatohepatitis via TLR4-Lipid Raft Recruitment. Am J Pathol 185: 1944-57.

Deng et al., 2017. Mitochondria Targeted Nanoscale Zeolitic Imidazole Framework-90 for ATP Imaging in Live Cells. J Am Chem Soc 139: 5877-82.

Domingues et al., 2018. Melanoma treatment in review. Immunotargets Ther 7: 35-49.

Dowling et al., 2018. Autophagy and T cell metabolism. Cancer Lett 419: 20-6.

Drury et al., 2011. Monomeric and dimeric CXCL12 inhibit metastasis through distinct CXCR4 interactions and signaling pathways. Proc. Natl. Acad. Sci. U. S. A 108: 17655-60.

Eikawa et al., 2015. Immune-mediated antitumor effect by type 2 diabetes drug, metfomnin. Proc Natl Acad Sci U S A 112: 1809-14.

Fanciulli et al., Energy Metabolism of Human LoVo Colon Carcinoma Cells: Correlation to Drug Resistance and Influence of Lonidamine. Clin Cancer Res. Apr. 2000;6(4):1590-7.

Gajewski et al., 2013. Innate and adaptive immune cells in the tumor microenvironment. Nat Immunol 14: 1014-22.

Gajewski. 2006. Identifying and overcoming immune resistance mechanisms in the melanoma tumor microenvironment. Clin Cancer Res 12:2326s-30s.

(56) References Cited

PUBLICATIONS

Gide et al., 2018. Primary and Acquired Resistance to Immune Checkpoint Inhibitors in Metastatic Melanoma. Clin Cancer Res 24: 1260-70.
Goffaux et al., 2017. A Dynamic Metabolic Flux Analysis of Myeloid-Derived Suppressor Cells Confirms Immunosuppression-Related Metabolic Plasticity. Sci Rep 7: 9850.
Gopal et al., 2014. Inhibition of mTORC1/2 overcomes resistance to MAPK pathway inhibitors mediated by PGC1alpha and oxidative phosphorylation in melanoma. Cancer Res 74: 7037-47.
Gottesman et al., Multidrug resistance in cancer: role of ATP-dependent transporters. Nat Rev Cancer. Jan. 2002;2(1):48-58.
Gottschalk et al., Imatinib (STI571)-mediated changes in glucose metabolism in human leukemia BCR-ABL-positive cells. Clin Cancer Res. Oct. 1, 2004;10(19):6661-8.
Gropper et al., 2017. Culturing CTLs under Hypoxic Conditions Enhances Their Cytolysis and Improves Their Anti-tumor Function. Cell Rep 20: 2547-55.
Gubser et al., 2013. Rapid effector function of memory CD8+ T cells requires an immediate-early glycolytic switch. Nat Immunol 14: 1064-72.
Hamid et al., 2013. Safety and tumor responses with lambrolizumab (anti-PD-1) in melanoma. N Engl J Med 369: 134-44.
Hanahan et al., 2011. Hallmarks of cancer: the next generation. Cell 144: 646-74.
Haq et al., Molecular pathways: BRAF induces bioenergetic adaptation by attenuating oxidative phosphorylation. Clin Cancer Res. May 1, 2014;20(9):2257-63.
Haq et al., Oncogenic BRAF regulates oxidative metabolism via PGC1α and MITF. Cancer Cell. Mar. 18, 2013;23(3):302-15.
Hardeman et al., 2017. Dependence On Glycolysis Sensitizes BRAF-mutated Melanomas For Increased Response To Targeted BRAF Inhibition. Sci Rep 7: 42604.
Hardie et al., 2014. AMPK: regulating energy balance at the cellular and whole body levels. Physiology. (Bethesda.) 29: 99-107.
Hardy et al., 2018. Detection and Characterization of Reactive Oxygen and Nitrogen Species in Biological Systems by Monitoring Species-Specific Products. Antioxid Redox Signal 28: 1416-32.
Hodi et al., 2010. Improved survival with ipilimumab in patients with metastatic melanoma. N Engl J Med 363: 711-23.
Holmstrom et al., 2014. Cellular mechanisms and physiological consequences of redox-dependent signalling. Nat Rev Mol Cell Biol 15: 411-21.
Hong et al., 2017. Suppression of B-Raf(V600E) melanoma cell survival by targeting mitochondria using triphenyl-phosphonium-conjugated nitroxide or ubiquinone. Cancer Biol Ther 18: 106-14.
Hosios et al., 2018. The redox requirements of proliferating mammalian cells. J Biol Chem 293: 7490-8.
Hwang et al., 2012. E-cadherin is critical for collective sheet migration and is regulated by the chemokine CXCL12 protein during restitution. J Biol. Chem 287: 22227-40.
Ippolito et al., Metabolic shift toward oxidative phosphorylation in docetaxel resistant prostate cancer cells. Oncotarget. Sep. 20, 2016;7(38):61890-904.
Janji et al., 2016. The multifaceted role of autophagy in tumor evasion from immune surveillance. Oncotarget 7: 17591-607.
Johnson et al., 1981. Monitoring of relative mitochondrial membrane potential in living cells by fluorescence microscopy. J Cell Biol 88: 526-35.
Kaelin. The concept of synthetic lethality in the context of anticancer therapy. Nat Rev Cancer. Sep. 2005;5(9):689-98.
Kalyanaraman et al., 2018. A review of the basics of mitochondrial bioenergetics, metabolism, and related signaling pathways in cancer cells: Therapeutic targeting of tumor mitochondria with lipophilic cationic compounds. Redox Biol 14: 316-27.
Kalyanaraman et al., 2018. Low-Temperature EPR Spectroscopy as a Probe-Free Technique for Monitoring Oxidants Formed in Tumor Cells and Tissues: Implications in Drug Resistance and OXPHOS-Targeted Therapies. Cell Biochem Biophys Sep. 26, 2018. doi: 10.1007/s12013-018-0858-1. [Epub ahead of print].
Kaminski et al., 2012. T cell activation is driven by an ADP-dependent glucokinase linking enhanced glycolysis with mitochondrial reactive oxygen species generation. Cell Rep 2: 1300-15.
Katayama et al., 2011. A sensitive and quantitative technique for detecting autophagic events based on lysosomal delivery. Chem Biol 18: 1042-52.
Kim et al., Current and upcoming mitochondrial targets for cancer therapy. Semin Cancer Biol. Dec. 2017;47:154-67.
Le Bourgeois et al., 2018. Targeting T Cell Metabolism for Improvement of Cancer Immunotherapy. Front Oncol 8: 237.
Li et al., 2018. Metformin-Induced Reduction of CD39 and CD73 Blocks Myeloid-Derived Suppressor Cell Activity in Patients with Ovarian Cancer. Cancer Res 78: 1779-91.
Liberman et al., 1969. Mechanism of coupling of oxidative phosphorylation and the membrane potential of mitochondria. Nature 222: 1076-8.
Lichtshtein et al., 1979. Use of a lipophilic cation for determination of membrane potential in neuroblastoma-glioma hybrid cell suspensions. Proc Natl Acad Sci U S A 76: 650-4.
Luengo et al., 2017. Targeting Metabolism for Cancer Therapy. Cell Chem Biol 24: 1161-80.
Ma et al., 2014. Targeting ER stress-induced autophagy overcomes BRAF inhibitor resistance in melanoma. J Clin Invest 124: 1406-17.
Melnikova et al., 2004. Genomic alterations in spontaneous and carcinogen-induced murine melanoma cell lines. Oncogene 23: 2347-56.
Mihm et al., 1996. Tumor infiltrating lymphocytes in lymph node melanoma metastases: a histopathologic prognostic indicator and an expression of local immune response. Lab Invest 74: 43-7.
Miller et al., 2016. Cancer treatment and survivorship statistics, 2016. CA Cancer J Clin 66: 271-89.
Mocholi et al., 2018. Autophagy Is a Tolerance-Avoidance Mechanism that Modulates TCR-Mediated Signaling and Cell Metabolism to Prevent Induction of T Cell Anergy. Cell Rep 24: 1136-50.
Modica-Napolitano et al., 1987. Basis for the selective cytotoxicity of rhodamine 123. Cancer Res 47:4361-5.
Molina et al., 2018. An inhibitor of oxidative phosphorylation exploits cancer vulnerability. Nat Med 24: 1036-46.
Mukhopadhyay et al., 2012. Mitochondrial reactive oxygen species generation triggers inflammatory response and tissue injury associated with hepatic ischemia-reperfusion: Therapeutic potential of mitochondrially targeted antioxidants. Free Radic. Biol. Med 53: 1123-38.
Muller et al., 2018. A 3D Organotypic Melanoma Spheroid Skin Model. J Vis Exp May 18, 2018;(135). doi: 10.3791/57500.
Murphy et al., Targeting antioxidants to mitochondria by conjugation to lipophilic cations. Annu Rev Pharmacol Toxicol. 2007;47:629-56.
Myers. 2016. Enhanced targeting of mitochondrial peroxide defense by the combined use of thiosemicarbazones and inhibitors of thioredoxin reductase. Free Radic Biol Med 91: 81-92.
Nadakavukaren et al., 1985. Increased rhodamine 123 uptake by carcinoma cells. Cancer Res 45: 6093-9.
Nakamura et al., 2002. Characterization of mouse melanoma cell lines by their mortal malignancy using an experimental metastatic model. Life Sci 70: 791-8.
Owens et al., 2012. Genomic instability induced by mutant succinate dehydrogenase subunit D (SDHD) is mediated by O2(-*) and H2O2. Free Radic Biol Med 52: 160-6.
Ozsvari et al., 2018. Exploiting mitochondrial targeting signal(s), TPP and bis-TPP, for eradicating cancer stem cells (CSCs). Aging (Albany NY) 10: 229-40.
Pan et al., 2018. Mitochondria-Targeted Honokiol Confers a Striking Inhibitory Effect on Lung Cancer via Inhibiting Complex I Activity iScience 3: 192-207.
Pearce et al., 2009. Enhancing CD8 T-cell memory by modulating fatty acid metabolism. Nature 460: 103-7.
Pereira et al., 2018. Metformin exerts antitumor activity via induction of multiple death pathways in tumor cells and activation of a protective immune response. Oncotarget 9: 25808-25.
Petrylak et al., Docetaxel and estramustine compared with mitoxantrone and prednisone for advanced refractory prostate cancer. N Engl J Med. Oct. 7, 2004;351(15):1513-20.

(56) References Cited

PUBLICATIONS

Pollak. Targeting oxidative phosphorylation: why, when, and how. Cancer Cell. Mar. 18, 2013;23(3):263-4.

Puleston et al., 2014. Autophagy in the immune system. Immunology 141:1-8.

Roesch et al., 2013. Overcoming intrinsic multidrug resistance in melanoma by blocking the mitochondrial respiratory chain of slow-cycling JARID1B(high) cells. Cancer Cell 23: 811-25.

Roy et al., 2015. Pancreatic Cancer Cell Migration and Metastasis Is Regulated by Chemokine-Biased Agonism and Bioenergetic Signaling. Cancer Res 75: 3529-42.

Roy et al., 2014. CXCL12 chemokine expression suppresses human pancreatic cancer growth and metastasis. PLoS. ONE 9: e90400.

$^{31}$P NMR of Mito-MGN $^{1}$H NMR of Mito-MGN $^{13}$C NMR of Mito-MGN $^{31}$P NMR of Mito$_{Me}$-MGN

A

B

R= H, Me; X= Alkyl chain, phenyl, PEG...; Y= H, CF$_3$, Me, Cl, OMe, C(O)CH$_3$, NO$_2$, N(Me)$_2$, ...

MITO-MAGNOLOL COMPOUNDS AND METHODS OF SYNTHESIS AND USE THEREOF

CROSS-REFERENCE TO RELATED APPLICATIONS

This Application is a continuation application of U.S. application Ser. No. 16/714,461 filed on Dec. 13, 2019 which claims priority to U.S. Provisional Application No. 62/779,795 filed on Dec. 14, 2018, the contents of which are incorporated by reference in their entireties.

STATEMENT REGARDING FEDERALLY SPONSORED RESEARCH OR DEVELOPMENT

Not Applicable.

FIELD OF THE INVENTION

This invention relates generally to mitochondria-targeting cationic drugs, specifically to mito-magnolol compounds, and methods of using the compounds to overcome drug resistance including kinase resistance in cancers.

BACKGROUND

Chemotherapy, drug resistance, and metabolic reprogramming. Most forms of chemotherapy (conventional antitumor agents such as doxorubicin, cis-platin, targeted therapies involving kinase inhibitors such as BRAF inhibitors) and immunotherapy using the check point inhibitors invariably induce drug resistance that renders them eventually ineffective (1). Numerous mechanisms (e.g., activation of drug efflux pumps) for drug resistance have been proposed (2). Recent reports suggest that metabolic reprogramming between a glycolytic phenotype and oxidative phosphorylation (OXPHOS) occurs during tumorigenesis or during oncogenic kinase inhibition in cancer cells (3,4). The critical dependence of cancer cells on OXPHOS or mitochondrial respiration for energy and survival suggests that cancer cell-selective and potent inhibitors of OXPHOS may be therapeutically exploited for inhibiting tumor growth, preventing or delaying resistance to kinase inhibitors (5).

Melanoma cancer. Melanoma is a very aggressive form of skin cancer accounting for the majority of skin cancer deaths. Currently, there exist no drugs for prolonged treatment of melanoma Mutations BRAFV600E are oncogenic driver mutations in cancers. Nearly 50% of melanoma patients exhibit a BRAFV600E mutation. The existing drugs (BRAF inhibitors) provide only a short-term benefit, followed by the rapid onset of drug resistance. Metastatic melanoma is characterized as a metabolic disease. Recent research classified melanomas into two categories: a Warburg-like glycolytic type and a high OXPHOS type characterized by high peroxisome proliferator-activated receptor gamma coactivator 1-alpha (PGC-1α), the master regulator of mitochondrial biogenesis and respiration (6,7). The high OXPHOS melanoma cells are sensitive to inhibitors of OXPHOS. The glycolytic melanoma cells are sensitive to inhibitors of kinases such as vemurafenib (as are most glycolytic phenotypes to kinase inhibitors) that decreases glycolytic flux (7). However, BRAF inhibitors cause metabolic reprogramming in a subset of melanomas and induced an increase in OXPHOS.

Colon cancer. Alterations in tumor metabolism is proposed as one of the reasons for acquired drug resistance following chemotherapy of colon cancer (8). Chemotherapy induced a shift in metabolism from glycolysis to OXPHOS in human colorectal tumors. Transcriptomics analyses revealed an increased expression of SIRT1 and PGC-1α in colon cancer cells following chemotherapy (9). In addition to inducing DNA repair processes, SIRT1 deacetylates PGC-1α, leading to PGC-1α activation that is essential for enhancing mitochondrial biogenesis and function (10). Facilitation of the SIRT1/PGC-1α signaling pathway activates the OXPHOS program and oxidative energy metabolism in colon cancer cells (10). Knockdown of SIRT1 or PGC-1α expression restored the chemotherapeutic efficacy (10). The chemoresistance was attributed to the increase in OXPHOS in colon cancer cells. From a therapeutic point of view, knockdown of these transcription factors in patients is not a viable option.

Prostate cancer. Drug-induced metabolic reprogramming—shifting from glycolysis to OXPHOS—was also shown in castration-resistant prostate cancer (11). Docetaxel (Taxotere) is being used as a "standard of care" chemotherapy for patients with castration-resistant metastatic prostate cancer (12). However, prolonged treatment with docetaxel induced acquired resistance in prostate cancer patients. Docetaxel-resistant PC3 cells (PC3-DR) displayed metabolic reprogramming and consequently increased OXPHOS (11).

Leukemia. Chronic myelogenous leukemia (CML.) is one of the most fatal forms of cancer in adults. Tyrosine kinases play a critical role during tumor development by promoting phosphorylation of ras-GTPase-activating protein in BCR-ABL oncogene protein (13). Imatinib (or Gleevec) inhibits phosphorylation of tyrosine kinase BCR-ABL, (13). A major concern, however, with Gleevec is development of drug resistance in CML patients.

A need exists for compounds that are effective in inhibiting tumor formation (i.e., reducing the severity or slowing the progression of symptoms of cancer) which have increased efficacy at lower doses while also mitigating resistance to chemo and radiotherapies. There is an urgent need to develop a new class of OXPHOS-targeting drugs which can be used for cancer treatment, including treating drug-resistant cancers.

SUMMARY OF THE INVENTION

Other features of the present invention will become apparent after review of the specification, claims and drawings.

The present disclosure provides mito-magnolol compounds, compositions comprising mito-magnolol compounds, kits and methods of use.

In one aspect, the disclosure provides a mito-magnolol compound of formula (I)

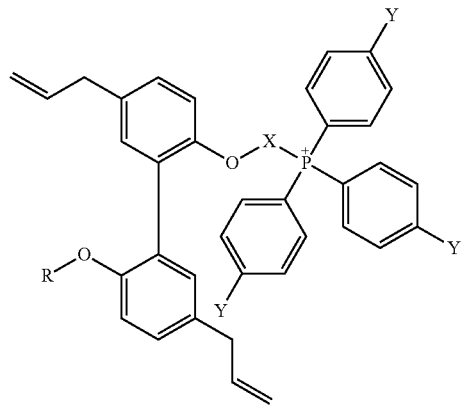

wherein
- X is selected from a $C_1$-$C_{18}$ alkyl, phenyl and polyethylene glycol (PEG);
- Each Y is independently selected from —H, —$CF_3$, methyl (Me), Cl, OMe, C(O)$CH_3$, $NO_2$, N(Me)$_2$; and
- R is selected from H, $C_1$-$C_{18}$ alkyl, phenyl, benzyl and polyethylene glycol (PEG).

For example, in one aspect, the disclosure provides a mito-magnolol compound of

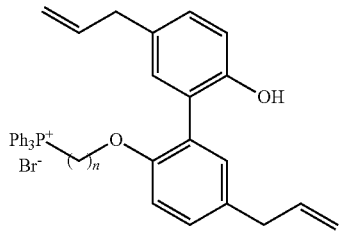

wherein n is an integer between 1 and 18.

In another aspect, the disclosure provides a mito-magnolol compound of

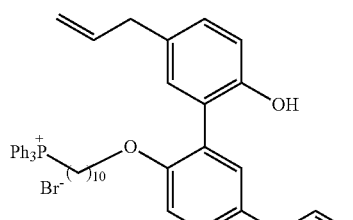

In another aspect the mito-magnolol compound is:

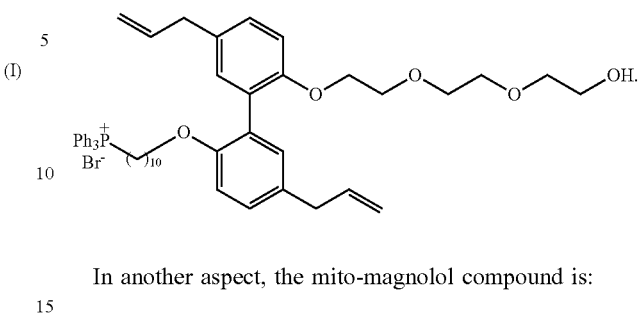

In another aspect, the mito-magnolol compound is:

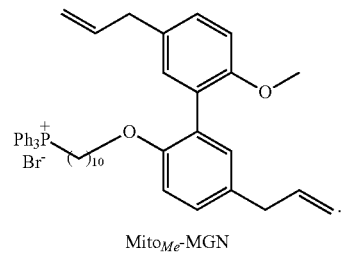

Mito$_{Me}$-MGN

In another aspect, the mito-magnolol compound is:

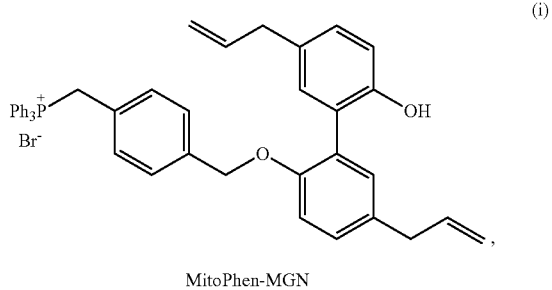

MitoPhen-MGN

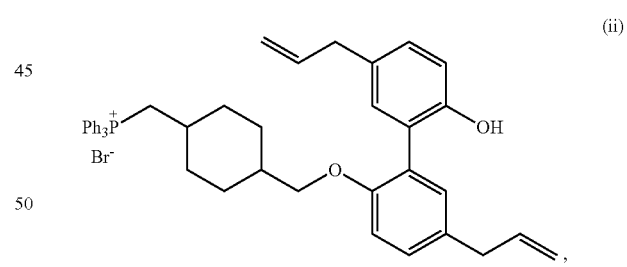

MitoCy-MGN

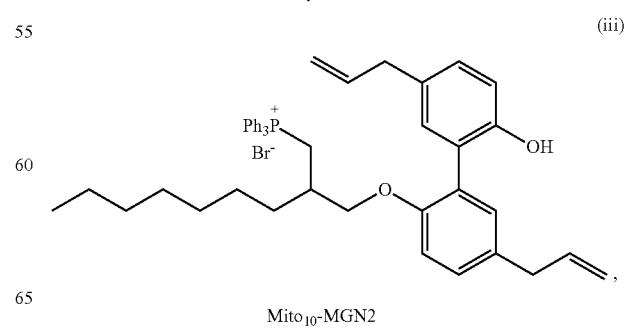

Mito$_{10}$-MGN2

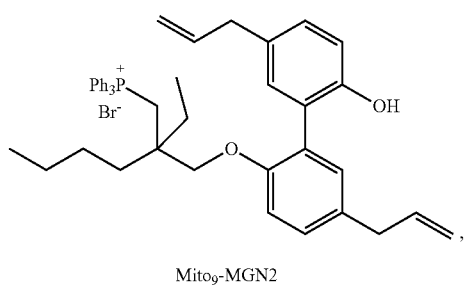

Mito₉-MGN2

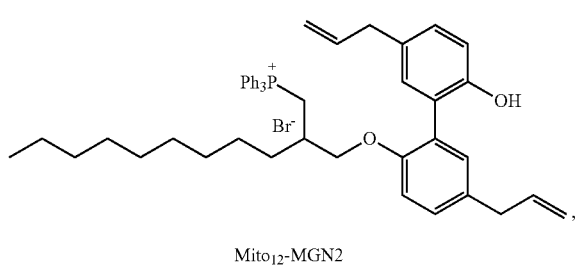

Mito₁₂-MGN2

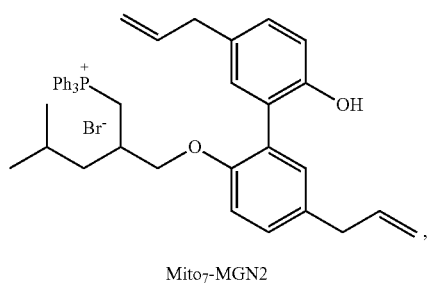

Mito₇-MGN2

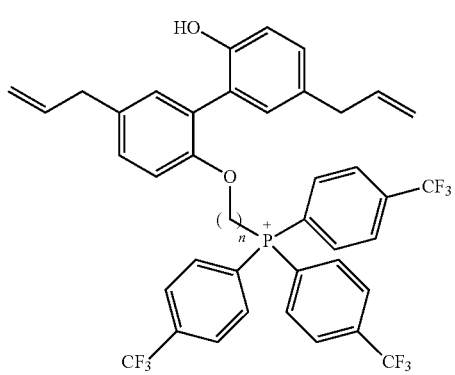

(vii)

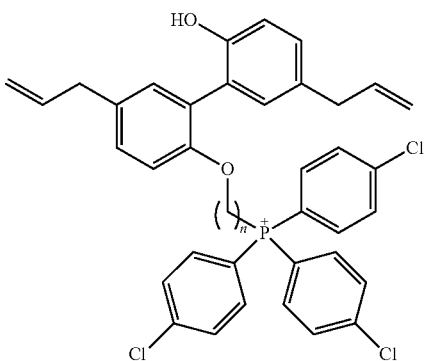

(viii)

Wherein n is an integer selected from 1-18, or wherein n is an integer selected from 1-18.

In another aspect, the disclosure provides a mito-magnolol compound of formula (II)

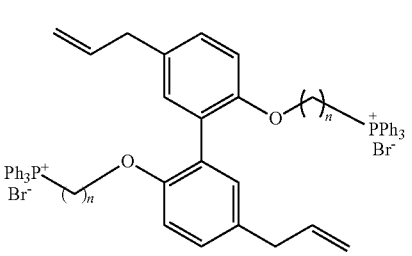

(II)

wherein each n is independently selected from an integer from 1-18.

In yet another aspect, the mito-magnolol compound is

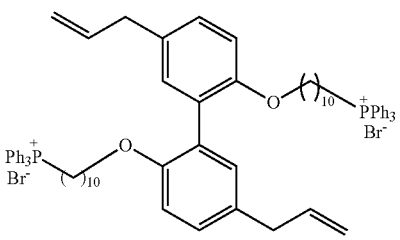

In a further embodiment, the disclosure provides a composition comprising the mito-magnolol compound described herein and a pharmaceutically acceptable carrier.

In yet another embodiment, the disclosure provides a method of treating cancer in a subject having cancer comprising administering the mito-magnolol compound or composition described herein in a therapeutically effective amount to treat the cancer.

In yet another embodiment, the disclosure provides a method of reducing or inhibiting cancer cell growth in a subject having cancer, the method comprising administering the mito-magnolol compound or composition described herein in a therapeutically effective amount to reduce or inhibit cancer cell growth.

In yet another aspect, the present disclosure provides a method of preventing or delaying resistance of a cancer to an anti-cancer therapy in a subject, the method comprising administering the mito-magnolol compound or composition described herein in a therapeutically effective amount to prevent or delay resistance of the cancer to the anti-cancer therapy.

In yet a further aspect, the disclosure provides a method of increasing a T cell response to an anti-cancer therapy in a cancer patient, the method comprising administering the mito-magnolol compound described herein in a therapeutically effective amount to increase the T cell response to the anti-cancer therapy.

In yet another aspect, the disclosure provides a kit comprising at least one mito-magnolol compound described herein, a pharmaceutically acceptable carrier or diluent, and instructional material.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
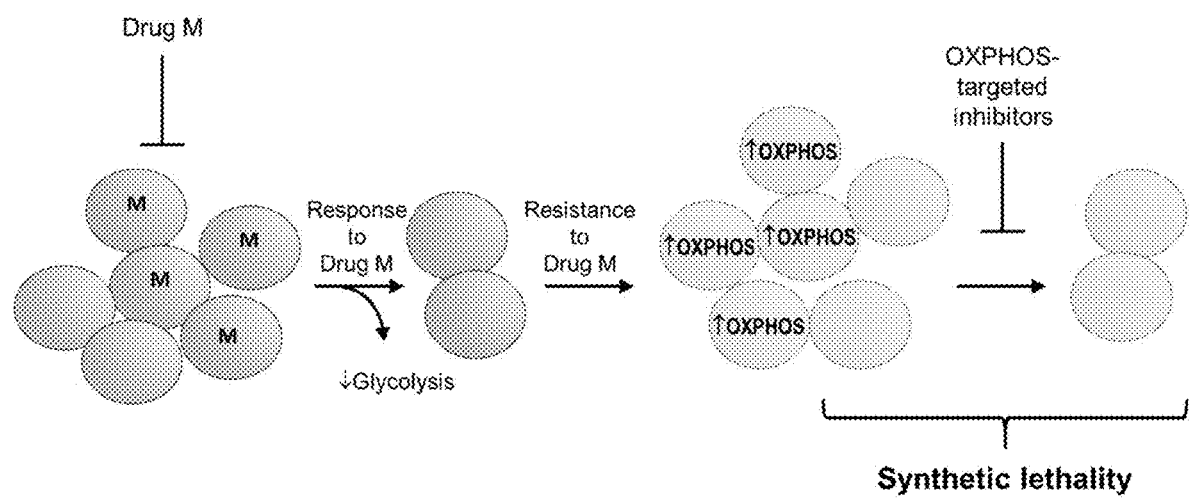
FIG. 1 shows a schematic representation of an OXPHOS inhibitor inducing synthetic lethality to tumor cells which are resistant to kinase inhibitor, Drug M.

In General. Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, cell lines, vectors, animals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

Compounds, Compositions and Synthesis

Tri-phenyl-phosphonium (TPP$^+$)-conjugated mitochondria-targeted agents, including mito-magnolol described herein are potent and selective inhibitors of OXPHOS in tumor cells (14-17). Compared to their untargeted analogs, the TPP$^+$-conjugated analogs are typically more potent, for example about 100 to 1,000 times more potent in inhibiting tumor cell proliferation. In addition, TPP$^+$-containing analogs lack the toxicity associated with usual mitochondrial OXPHOS inhibitors (e.g., rotenone, cyanide), exhibiting a high therapeutic index and limited off-target effects. Conventional inhibitors of mitochondrial electron transport chain complexes such as cyanide, oligomycin, 2,4-dinitrophenol, are not specific for cancer cell mitochondria, and these all have a low therapeutic index. Biguanides (e.g., metformin) exhibit antitumor effects, and a proposed mechanism involves targeting mitochondrial OXPHOS, albeit weakly. Metformin efficacy is further limited by transport requiring the presence of organic cation transporters (OCT).

In contrast, the newly developed mitochondria targeted agents (MTAs) described herein consist of the TPP$^+$ moiety conjugated to an organic molecule (magnolol) via an aliphatic side chain MTAs are targeted to mitochondria, driven by the presence of an increased negative mitochondrial membrane potential in cancer cells (18,19). MTAs are lipophilic and cationic, and diffuse across the cell membrane. The presence of OCT is not required for efficient intracellular accumulation of MTAs.

The present disclosure provides mito-magnolol compounds (e.g., Mito-MGN), a mitochondria-targeted derivative of the naturally occurring bioactive polyphenolic molecule, magnolol. Magnolol is the most abundant bioactive component of *magnolia* extract, a traditional herbal formula used effectively for centuries in East Asia for treating multiple diseases (32). One advantage of magnolol is its ability to be modified into a single monosubstituted isomer that is easily separated and purified, enabling synthesis of large quantities of Mito-magnolol.

In one embodiment, the present disclosure provides novel mito-magnolol compounds modified to selectively and synergistically inhibit cancer proliferation and progression Specifically, the inventors have shown that linking triphenylphosphonium (TPP) to magnolol via long alkyl chains yields a novel mito-magnolol compound which can treat cancer, including chemotherapeutic resistant cancers. The compound comprises mono- and bis-substituted mito-magnolol molecules.

In one embodiment, the disclosure provides a mito-magnolol compound of formula (I)

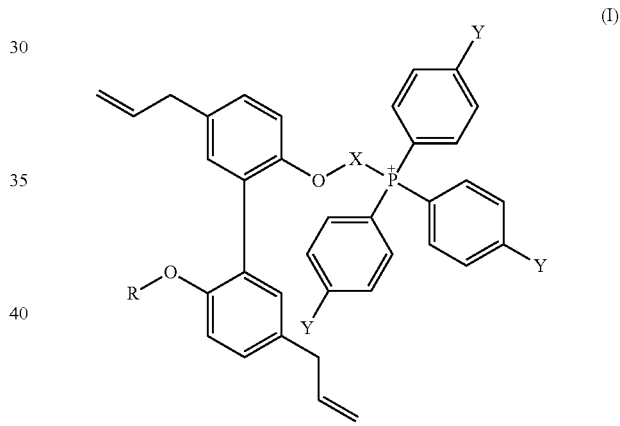

(I)

wherein

X is selected from a $C_1$-$C_{18}$ alkyl, phenyl and polyethylene glycol (PEG) or using other linkers (e.g., benzyl, ramification of the alkyl side chain, double bound, etc.);

each Y is independently selected from —H, —CF, methyl (Me), Cl, and OMe, C(O)CHI, $NO_2$, $N(Me)_2$;

and R is selected from H, alkyl chain ($C_nH_{2n+1}$, n=1-18), phenyl, benzyl, and polyethylene glycol (PEG).

For Example, the mito-magnolol compound can be

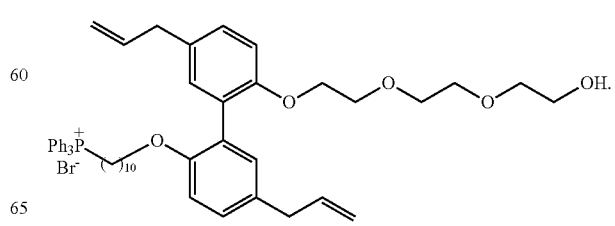

In another example, the mito-magnolol can be

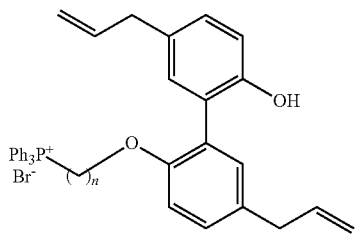

wherein n is an integer selected from 1-18. In another embodiment. n is an integer selected from 6-12.

In a preferred example, the mito-magnolol of formula (I) comprises X is $C_1$-$C_{18}$ alkyl, each Y is H and R is H.

In one embodiment, the mito-magnolol is:

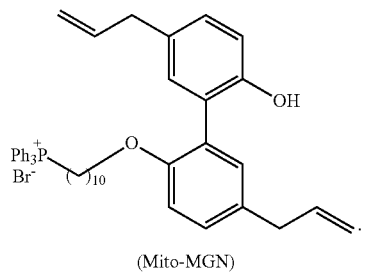

(Mito-MGN)

Another embodiment provides a mito-magnolol compound of:

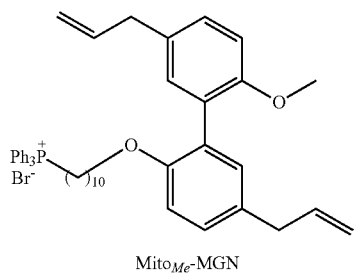

Mito$_{Me}$-MGN

Other structures are as follows:

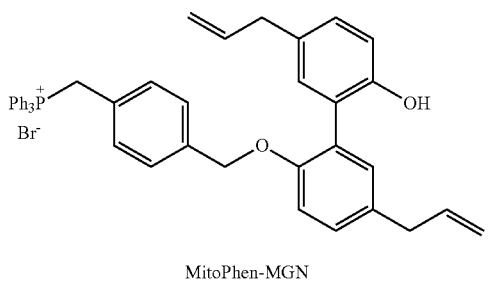

MitoPhen-MGN

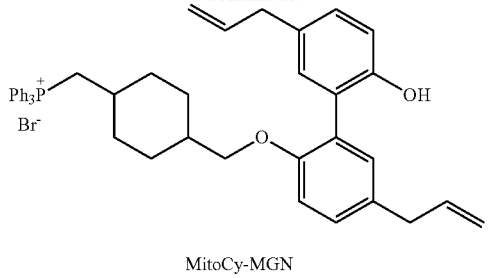

MitoCy-MGN

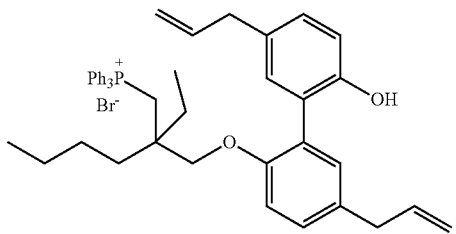

Mito$_{10}$-MGN2

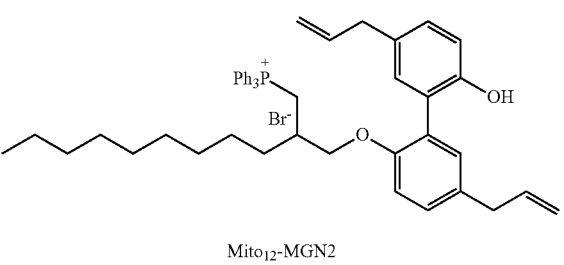

Mito$_9$-MGN2

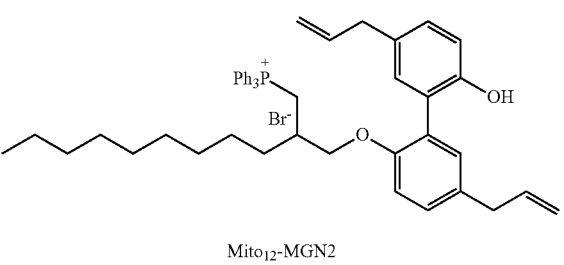

Mito$_{12}$-MGN2

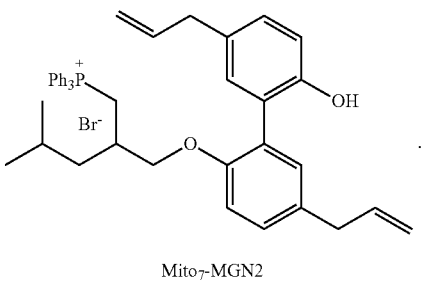

Mito$_7$-MGN2

In another embodiment, the mito-magnolol compound is formula (II)

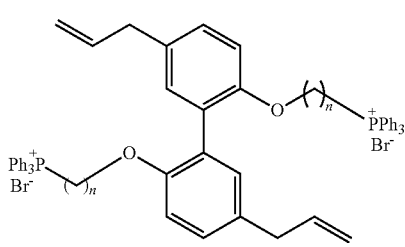

wherein each n is selected independently from an integer from 1-18.

In one embodiment, the mito-magnolol of formula (II) is

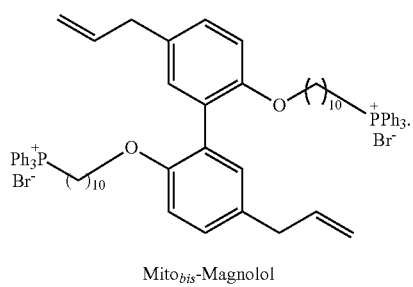

Mito$_{bis}$-Magnolol

The present disclosure also provides composition comprising the mito-magnolol compound described herein and a pharmaceutically acceptable carrier A "pharmaceutically acceptable carrier" means any conventional pharmaceutically acceptable carrier, vehicle, or excipient that is used in the art for production and administration of compositions to a subject. Pharmaceutically acceptable carriers are typically non-toxic, inert, solid or liquid carriers which are physiologically balanced. Typically, phosphate buffered saline or other saline solutions are physiologically acceptable carriers. A pharmaceutically acceptable carrier can be selected on the basis of the selected route of administration and standard pharmaceutical practice. The compounds may be formulated into dosage forms according to standard practices in the field of pharmaceutical preparations. See Alphonso Gennaro, ed., Remington's Pharmaceutical Sciences. 18th Ed., (1990) Mack Publishing Co., Easton, Pa, which is incorporated by reference in its entirety. Suitable dosage forms may comprise, but are not limited to, for example, solutions, parenteral solutions, injectable solutions, troches, suppositories, or suspensions.

For oral administration, the active agent may be combined with one or more solid inactive ingredients for the preparation of tablets, capsules, pills, powders. granules or other suitable oral dosage forms. For example, the active agent may be combined with at least one excipient such as fillers, binders, humectants, disintegrating agents, solution retarders, absorption accelerators, wetting agents, absorbents or lubricating agents Additional oral administration forms are contemplated, including, but not limited to, elixirs, liquids, solutions, suspensions, emulsions, multi-layer tablets, soft gelatin capsules, hard gelatin capsules, troches, lozenges, beads. granules, particles, microparticles, dispensable granules, cachets, among others. Formulations of the present technology suitable for oral administration can be presented as discrete units, such as capsules, caplets or tablets. These oral formulations also can comprise a solution or a suspension in an aqueous liquid or a non-aqueous liquid. The formulation can be an emulsion, such as an oil-in-water liquid emulsion or a water-in-oil liquid emulsion. The oils can be administered by adding the purified and sterilized liquids to a prepared enteral formula, which can then be placed in the feeding tube of a patient who is unable to swallow. Another oral administration may be the formation of a liquid or gel suitable for oral dosage. In one embodiment, the compounds may be formulated in water, juice, or other beverage for oral consumption.

For parenteral administration, the active agent may be mixed with a suitable carrier or diluent such as water, an oil (e.g., a vegetable oil), ethanol, saline solution (e.g., phosphate buffer saline or saline), aqueous dextrose (glucose) and related sugar solutions, glycerol, or a glycol such as propylene glycol or polyethylene glycol. Stabilizing agents, antioxidant agents and preservatives may also be added. Suitable antioxidant agents include sulfite, ascorbic acid, citric acid and its salts, and sodium EDTA. Suitable preservatives include benzalkonium chloride, methyl- or propylparaben, and chlorbutanol. The composition for parenteral administration may take the form of an aqueous or nonaqueous solution, dispersion, suspension or emulsion.

The pharmaceutical composition is preferably in unit dosage form. In such form the preparation is divided into unit doses containing appropriate quantities of the active component. The unit dosage form can be a packaged preparation, the package containing discrete quantities of preparation, such as packeted tablets, capsules, and powders in vials, or ampoules. Also, the unit dosage form can be a capsule, tablet, cachet, or lozenge itself, or it can be the appropriate number of any of these in packaged form.

Methods of synthesizing the mito-magnolols of the present disclosure are shown in FIGS. 13A and 13B, and described in the Examples below. Briefly, mito-magnolol was prepared by reacting 10-bromodecyltriphenylphosphonium bromide with magnolol in the presence of potassium carbonate in DMF (FIG. 13A). To a mixture of magnolol (0.2 g, 0.75 mmol) and anhydrous potassium carbonate (0.22 g, 1.5 mmol) in DMF (20 mL) was added 10-bromodecyltriphenylphosphonium bromide (0.42 g, 0.75 mmol) at 0° C. The mixture was stirred at 35° C. for 24 hours. The residue was taken up into water and extracted with $CH_2Cl_2$. The organic layer was dried over $Na_2SO_4$, and the solvent was removed under reduced pressure. Ether was added to precipitate the crude product. Purification by flash chromatography using the following gradient from $CH_2Cl_2$ (100%) to $CH_2Cl_2$/EtOH (80/20) as eluent delivered the corresponding Mito-magnolol (200 mg, 35% yield) and the Mito-bis-magnolol (80 mg. 14% yield) as white solids.

Me-magnolol and DiMe-magnolol were prepared by reacting methyl iodide with magnolol in the presence of potassium carbonate in DMF. Williamson reaction of 2-O-methylmagnolol and 10-bromodecyltriphenvlphosphonium bromide in the presence of potassium carbonate led to Mito$_{ME}$-magnolol (FIG. 13B). One skilled in the art is able to modify these methods to produce other mito-magnolols contemplated herein.

Methods of Use

The compounds and compositions of the present disclosure may be used for methods of treating cancer, including methods of overcoming resistance to chemotherapies, for example, overcoming resistance to oncogene-targeted therapies or checkpoint inhibitors. The compounds and compositions comprising mito-magnolols act as potent OXPHOS inhibitors, which can be used alone or in combination with other anti-cancer therapies, including chemotherapeutic agents, to treat cancer, including drug-resistant cancer (e.g., drug resistant-melanoma), in a subject in need thereof.

In one embodiment, the disclosure provides methods of treating cancer, including treatment of cancers associated with increases levels of OXPHOS. In one embodiment, the TPP$^+$-conjugated mitochondria-targeted mito-magnolols selectively localize within the more negative mitochondria of cancer cells and are potent and selective inhibitors of OXPHOS in cancer cells, including, but not limited to melanoma, breast, colon, lung, and pancreas cancer cells. As demonstrated in the examples, mito-magnolol potently inhibits OXPHOS and tumor cell proliferation in drug resistant melanoma.

In one embodiment, the mito-magnolol compounds of the present invention provide effective methods of treating cancer. In one embodiment, the mito-magnolol compounds potently inhibit tumor formation. In some embodiments, the cancer is a primary tumor. In some embodiments, the cancer is a metastatic cancer. In one embodiment, the mito-magnolol compounds or compositions described herein reduce or prevent metastasis. In another embodiment, the mito-magnolol compounds are able to treat or inhibit anti-cancer (e.g., chemotherapeutic) or drug resistant cancer, for example, drug resistant melanoma.

By "cancer" or "tumor" we mean any abnormal proliferation of tissues, including solid and non-solid tumors. For instance, the composition and methods of the present invention can be utilized to treat cancers that manifest solid tumors such as skin cancer including melanoma, pancreatic cancer, breast cancer, colon cancer, lung cancer, prostate cancer, thyroid cancer, ovarian cancer, bladder cancer, and the like. The composition and methods of the present disclosure can also be utilized to treat non-solid tumor cancers such as non-Hodgkin's lymphoma, leukemia and the like.

The term "metastasis," "metastatic tumor" or "secondary tumor" refers to cancer cells that have spread to a secondary site, e.g., outside of the primary tumor tissue. Secondary sites include, but are not limited to, the lymphatic system, skin, distant organs (e.g., liver, stomach, pancreas, brain, etc.) and the like. In some embodiments, the mito-magnolol compounds provide methods of treating a primary or secondary tumor.

In one embodiment, the disclosure provides a method of treating cancer in a subject having cancer comprising: administering the mito-magnolol compound described herein in a therapeutically effective amount to treat the cancer.

In a preferred embodiment, the cancer is a melanoma, and in some embodiments, is a melanoma resistant to cancer therapy, for example, chemotherapy or immunotherapy. In some embodiments, the melanoma is resistant to BRAF inhibitor. In other embodiments, the melanoma is resistant to MEK inhibitor.

In some embodiment, the cancer therapy is a BRAF inhibitor. Suitable BRAF inhibitors are known in the art and include, but are not limited to, vemurafenib, dabrafenib. encorafenib, among others. In one example, the BRAF inhibitor is vemurafenib.

In another embodiment, the cancer therapy is a MEK inhibitor. Suitable MEK inhibitors include, but are not limited to, for example, trametinib (Mekinist), cobimetinib (Cotellic), and binimetinib (Mektovi), among others.

In a further embodiment, the cancer therapy is a checkpoint inhibitor. Suitable checkpoint inhibitors are known in the art and include, but are not limited to, for example, a PD-1 inhibitors, PD-L1 inhibitors, CTLA-4 inhibitors, and the like. Suitable PD-1 inhibitors include, but are not limited to, for example, anti-PD-1 antibodies, e.g. pembrolizumab (Keytruda), Nivolumab (Opdivo), and Cemiplimab (Libtayo), among others. Suitable anti-PD-L 1 inhibitors, include, but are not limited to, for example, anti-PD-L1 antibodies, including, but not limited to, Atezolizumab (Tecentriq), Avelumab (Bavencio). and Durvalumab (Imtinzi), among others.

The present disclosure also provides methods of reducing or inhibiting cancer cell growth in a subject having cancer, the method comprising administering the mito-magnolol compound described herein in a therapeutically effective amount to reduce or inhibit cancer cell growth. In some embodiments, the cancer cell is resistant to an anti-cancer therapy or drug, for example, a BRAF inhibitor.

In another embodiment, the disclosure provides a method of inhibiting, preventing or delaying resistance of a cancer to an anti-cancer drug in a subject, the method comprising: administering the mito-magnolol compound or compositions described herein in a therapeutically effective amount to inhibit, prevent or delay resistance of the cancer to the anti-cancer drug.

In some embodiments, any of the methods described herein include administering the mito-magnolol compound in combination with one or more cancer therapies as further described herein. Suitable cancer therapies (i.e., anti-cancer therapies) are known in the art, and may include cancer therapies in which the tumor is resistant to when administered alone.

In some embodiments, the mito-magnolol compound is administered co-currently with the anti-cancer drug. In other embodiments, the mito-magnolol compound or composition is administered after beginning treatment with the anti-cancer drug. In other embodiments, the mito-magnolol compound or composition is administered before, during, or both before and during treatment with an anti-cancer drug.

By "subject" we mean mammals and non-mammals. "Mammals" means any member of the class Mammalia including, but not limited to, humans, non-human primates such as chimpanzees and other apes and monkey species; farm animals such as cattle, horses, sheep, goats, and swine; domestic animals such as rabbits, dogs, and cats; laboratory animals including rodents, such as rats. mice, and guinea pigs; and the like. Examples of non-mammals include, but are not limited to, birds, fish and the like. The term "subject" does not denote a particular age or sex. In a preferred embodiment, the subject is a human.

By "treating" we mean the management and care of a subject for the purpose of combating the disease, condition, or disorder. Treating includes the administration of a compound or composition described herein to reduce, prevent, ameliorate and/or improve the onset of the symptoms or complications, alleviating the symptoms or complications, or reducing or eliminating the disease, condition, or disorder. For example, treating cancer in a subject includes the reducing, repressing, delaying or preventing cancer growth, reduction of tumor volume, and/or preventing, repressing, delaying or reducing metastasis of the tumor. Treating cancer in a subject also includes the reduction of the number of tumor cells within the subject. The term "treatment" can be characterized by at least one of the following: (a) the reducing, slowing or inhibiting the growth of cancer and cancer cells, including slowing or inhibiting the growth of metastatic cancer cells; (b) preventing the further growth of tumors, (c) reducing or preventing the metastasis of cancer cells within a subject; and (d) reducing or ameliorating at least one symptom of cancer. In some embodiments, the optimum effective amount can be readily determined by one skilled in the art using routine experimentation.

By "ameliorate", "amelioration", "improvement" or the like we mean a detectable improvement or a detectable change consistent with improvement that occurs in a subject or in at least a minority of subjects, e.g., in at least about 2%, 5%, 10%, 15%, 20%, 25%, 30%, 40%, 50%. 60%, 70%, 75%, 80%, 85%, 90%, 95%, 98%, 100% or in a range about between any two of these values. Such improvement or change may be observed in treated subjects as compared to subjects not treated with the mito-magnolol compounds, where the untreated subjects have, or are subject to developing, the same or similar disease, condition, symptom or the like. Amelioration of a disease, condition, symptom or assay parameter may be determined subjectively or objectively, e.g., self-assessment by a subject(s), by a clinician's assessment or by conducting an appropriate assay or measurement, including, e.g., a quality of life assessment, a slowed progression of a disease(s) or condition(s), a reduced severity of a disease(s) or condition(s), or a suitable assay(s) for the level or activity(ies) of a biomolecule(s), cell(s) or by detection of cell migration within a subject Amelioration may be transient, prolonged or permanent or it may be variable at relevant times during or after the mito-magnolol compound is administered to a subject or is used in an assay or other method described herein or a cited reference, e.g., within about 1 hour of the administration or use of the mito-magnolol compounds to about 3, 6, 9 months or more after a subject(s) has received the mito-magnolol compounds.

By "modulation" of, e.g., a symptom, level or biological activity of a molecule, replication of a pathogen, cellular response, cellular activity or the like means that the cell level or activity is detectably increased or decreased. Such increase or decrease may be observed in treated subjects as compared to subjects not treated with the mito-magnolol compounds, where the untreated subjects have, or are subject to developing, the same or similar disease, condition, symptom or the like. Such increases or decreases may be at least about 2%, 5%, 10%, 15%, 20%, 25%, 30%, 40% NO, 50%, 60%, 70%, 75%, 80%, 85%, 90%, 95%, 98%, 100%, 150%, 200%, 250%, 300%, 400%, 500%. 1000% or more or about within any range about between any two of these values. Modulation may be determined subjectively or objectively, e.g., by the subject's self-assessment, by a clinician's assessment or by conducting an appropriate assay or measurement, including, e.g., quality of life assessments or suitable assays for the level or activity of molecules, cells or cell migration within a subject. Modulation may be transient, prolonged or permanent or it may be variable at relevant times during or after the mito-magnolol compound is administered to a subject or is used in an assay or other method described herein or a cited reference, e.g., within about 1 hour of the administration or use of the mito-magnolol compounds to about 3, 6, 9 months or more after a subject(s) has received the mito-magnolol compounds.

By "administering" we mean any means for introducing the mito-magnolol compounds or compositions into the body, preferably into the systemic circulation. Examples include but are not limited to oral, buccal, sublingual, pulmonary, transdermal, transmucosal, as well as subcutaneous, intraperitoneal, intravenous, and intramuscular injection. A preferred method of administering the mito-magnolol compounds or pharmaceutical compositions of the present invention for treatment of cancer, particularly melanoma, is by oral or topical administration. Administering also includes introducing the mito-magnolol compounds or compositions locally to the cancer, for example, but not limited to, by topical treatment or injection into the tumor site.

The term "effective amount" or "therapeutically effective amount" refers to an amount sufficient to effect beneficial or desirable biological and/or clinical results. That result can be reducing, inhibiting or preventing the growth of cancer cells, including drug-resistant or therapy resistant cancer cells, reducing, inhibiting or preventing metastasis of the cancer cells or invasiveness of the cancer cells or metastasis, or reducing, alleviating, inhibiting or preventing at least one symptoms of the cancer or metastasis thereof, or any other desired alteration of a biological system. An "effective treatment" refers to treatment producing a beneficial effect, e.g., amelioration of at least one symptom of a cancer. A beneficial effect can take the form of an improvement over baseline, i.e., an improvement over a measurement or observation made prior to initiation of therapy according to the method. A beneficial effect can also take the form of reducing, inhibiting or preventing further growth of cancer cells, reducing, inhibiting or preventing metastasis of the cancer cells or invasiveness of the cancer cells or metastasis or reducing, alleviating, inhibiting or preventing at least one symptoms of the cancer or metastasis thereof. Such effective treatment may, e.g., reduce patient pain, reduce the size or number of cancer cells, may reduce or prevent metastasis of a cancer cell, or may slow cancer or metastatic cell growth.

In one embodiment, the therapeutically effective amount ranges from between about 0.1-50 mg/kg. A therapeutically effective amount of the mito-magnolol compounds vary according to factors such as the disease state, age, sex, and weight of the subject, and the ability of the mito-magnolol compounds to elicit a desired response in the subject. Dosage regimens may be adjusted to provide the optimum therapeutic response. A therapeutically effective amount is also one in which any toxic or detrimental effects of the mito-magnolol compounds of the present invention are outweighed by the therapeutically beneficial effects.

The disclosure further provides methods of increasing a T cell response to an anti-cancer therapy in a cancer patient, the method comprising administering the mito-magnolol compound or composition in a therapeutically effective amount to increase the T cell response to the therapy. In some embodiments, the anti-cancer therapy is a BRAF inhibitor or an inhibitor of oncogenic kinase. In another embodiment, the anti-cancer therapy is a checkpoint inhibitor.

The term "anti-cancer therapy," "cancer therapy," and "anti-cancer drug" are used interchangeably to refer to therapeutics that are used for the treatment of cancer, including chemotherapy, immunotherapy, among others. Suitable anti-cancer therapies are known in the art and depend on the type of cancer being treated. Suitable anti-cancer therapies are described herein and include, for example kinase inhibitors, including BRAF inhibitors or MEK inhibitors, checkpoint inhibitors, and chemotherapeutics.

In another embodiment, the mito-magnolol compounds and compositions described herein are able to provide synthetic lethality as OXPHOS inhibitors. In one embodiment, the mito-magnolol compounds and compositions are able to overcome resistance to oncogene-targeted therapies. The concept of synthetic lethality that has been frequently used in targeted chemotherapy is schematically shown in FIG. 1. There are several types of synthetic lethality (20,21) as follows: 1) Genotype-specific synthetic lethality between two genes (gene products) occurs when the cell is functional with mutation of one gene but loss of both genes trigger cancer cell death; 2) Drug-specific synthetic lethality occurs when cells treated with an inhibitor or drug M for a mutated oncogene adapt another signaling pathway and the use of another drug (targeted inhibitor of OXPHOS) for the new adapted signaling pathway induces toxicity to mutated cancer cells (FIG. 1).

The therapeutic combinations of an anti-cancer therapy, preferably in one embodiment a kinase inhibitor (e.g., BRAF inhibitor) with mito-magnolols described herein can be used for inhibiting OXPHOS is an example of drug-specific synthetic lethality. This disclosure demonstrates synthetic lethality through pharmacological mechanism targeting the adaptive potential of transformed cells to upregulate OXPHOS in cancer cells subjected to oncogenic kinase inhibition. Through synthetic lethality mechanism, the MTAs described herein through inhibiting OXPHOS can mitigate and delay onset of drug resistance to anti-cancer therapies, including chemotherapies and immunotherapies, for example, the combination therapy of metformin and vemurafenib, inhibitor of oncogenic BRAFV600E, in metastatic melanoma patients. The Examples demonstrate the use Mito-magnolol in wild type and BRAFV600E-resistant melanoma cells.

In one embodiment, the compounds and compositions described herein are used in methods of reducing, suppressing, or killing BRAF inhibitor resistant cells.

In some embodiments, the mito-magnolol compounds and compositions described herein can be used synergistically in combination with a checkpoint inhibitor to treat cancer. In some embodiments, the checkpoint inhibitor is a PD-1 or a PD-L1 checkpoint inhibitor.

Kits.

In another embodiment, the present disclosure provides a kit comprising a pharmaceutical composition comprising the mito-magnolol compounds and instructional material. By "instructional material" we mean a publication, a recording, a diagram, or any other medium of expression which is used to communicate the usefulness of the pharmaceutical composition of the invention for one of the purposes set forth herein in a human. The instructional material can also, for example, describe an appropriate dose of the pharmaceutical composition. The instructional material of the kit of the invention can, for example, be affixed to a container which contains a pharmaceutical composition of the invention or be shipped together with a container which contains the pharmaceutical composition. Alternatively, the instructional material can be shipped separately from the container with the intention that the instructional material and the pharmaceutical composition be used cooperatively by the recipient.

In some embodiments, the kit may further comprise one or more anti-cancer therapies to use in combination with the mito-magnolol compounds.

EXAMPLES

The following examples are, of course, offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims. 100%1 Example 1. Development of OXPHOS inhibitors for use in treatment of cancer.

This Example demonstrates methods of making mito-magnolol, and the ability of mito-magnolol to inhibit proliferation of both wild type and drug resistant melanoma in vitro. This Example further demonstrates that mito-magnolol compounds can stimulate ROS and cause oxidation of mitochondrial antioxidative enzyme in BRAFV600E inhibitor-resistant melanoma cells.

Figure 12:
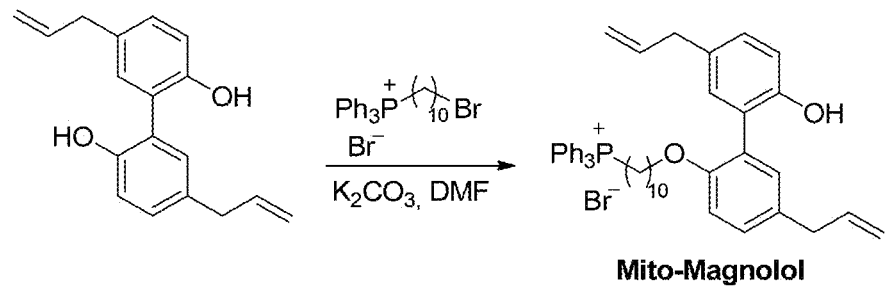
FIG. 12 shows schemes for synthesis of Mito-magnolol and $\text{Mito}_{Me}$-magnolol. (A) Synthesis of Mito-magnolol. Reagents and conditions: i, $K_2CO_3$, DMF, 40° C., 35%. (B) Synthesis of $\text{Mito}_{Me}$-magnolol Reagents and conditions: i, $CH_3I$, DMF, 6 h, $K_2CO_3$, 35° C., 64%. ii, $K_2CO_3$, DMF, 40° C., 60%. 2-O-Me-MGN is 2-O-methylmagnolol.
Figure 12:
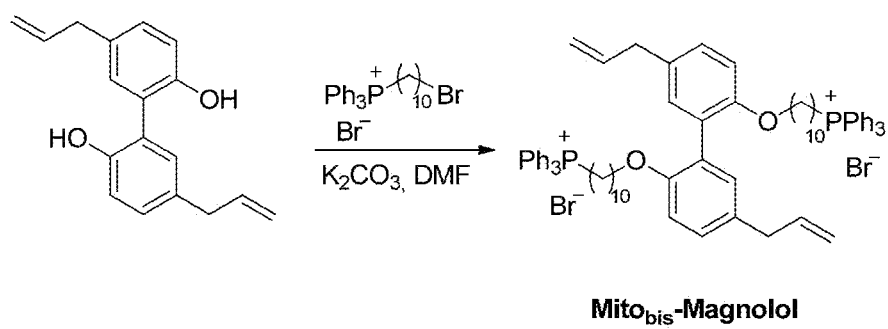
Figure 12:
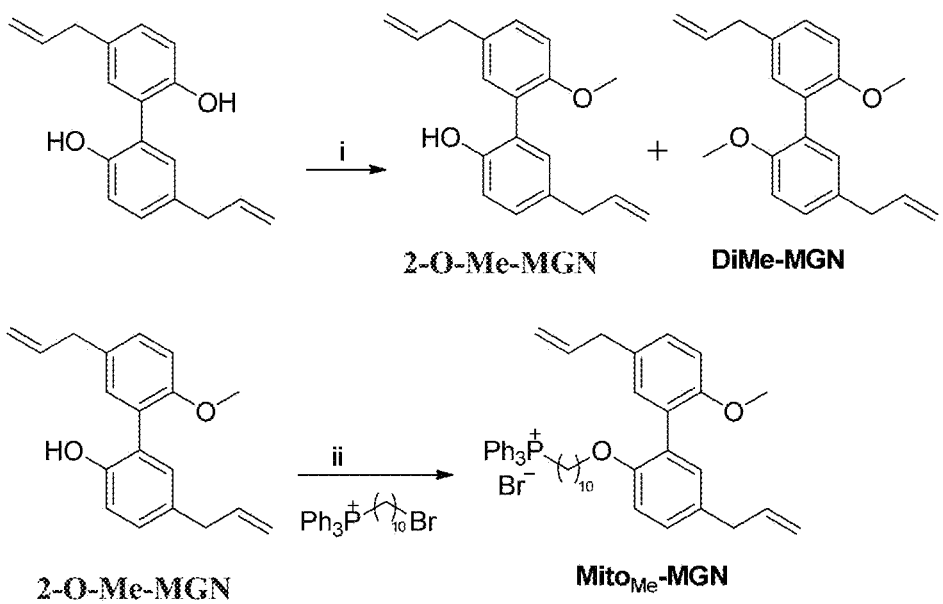

Synthesis of Mito-magnolol. Mito-magnolol was prepared by reacting 10-bromodecyltriphenylphosphonium bromide with magnolol in the presence of potassium carbonate in DMF (FIG. 12A). To a mixture of magnolol (0.2 g, 0.75 mmol) and anhydrous potassium carbonate (0.22 g, 1.5 mmol) in DMF (20 mL) was added 10-bromodecyltriphenylphosphonium bromide (0.42 g, 0.75 mmol) at 0° C. The mixture was stirred at 35° C. for 24 hours. The residue was taken up into water and extracted with $CH_2Cl_2$. The organic layer was dried over $Na_2SO_4$, and the solvent was removed under reduced pressure. Ether was added to precipitate the crude product. Purification by flash chromatography using the following gradient from $CH_2Cl_2$ (100%) to $CH_2Cl_2$/EtOH (80/20) as eluent delivered the corresponding Mito-magnolol (200 mg, 35% yield) and the Mito-bis-magnolol (80 mg, 14% yield) as white solids.

Figure 2:
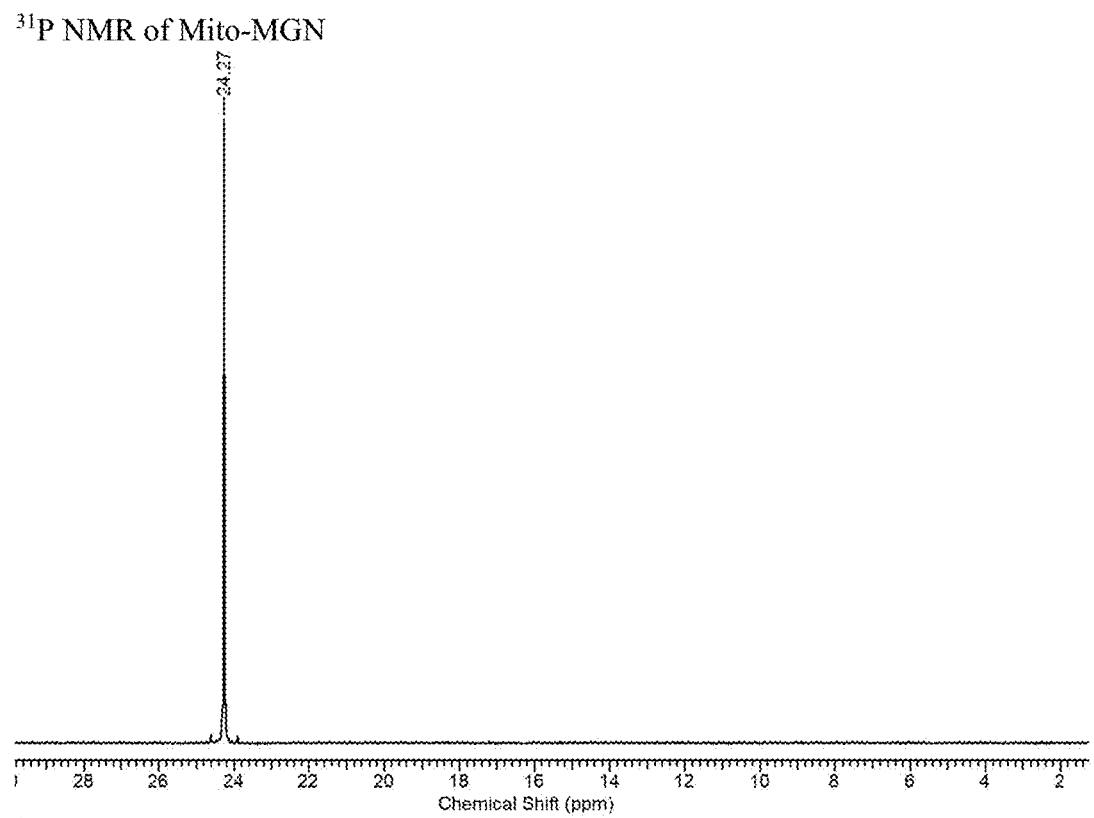
FIG. 2 shows NMR spectra of Mito-magnolol (Mito-MGN) and Mito-methylmagnolol ($\text{Mito}_{Me}$-MGN).
Figure 2:
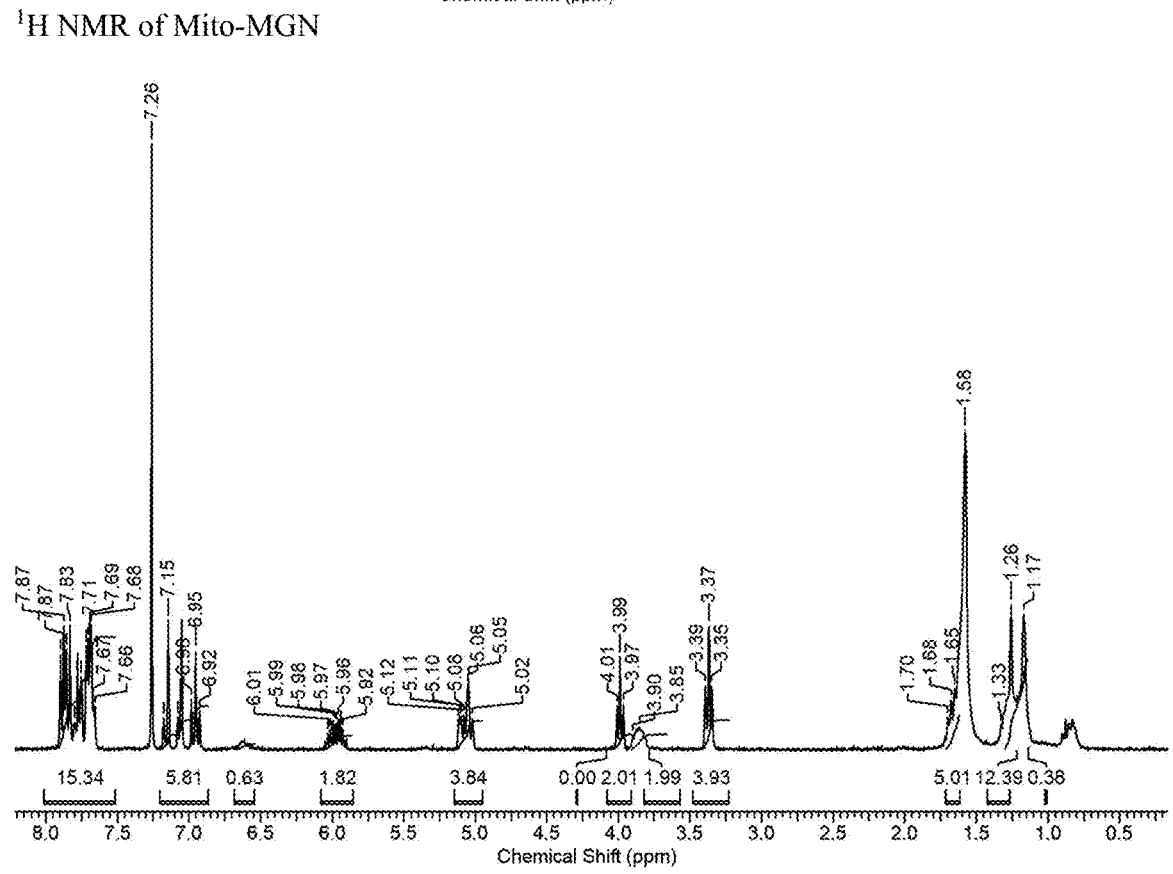
Figure 2:
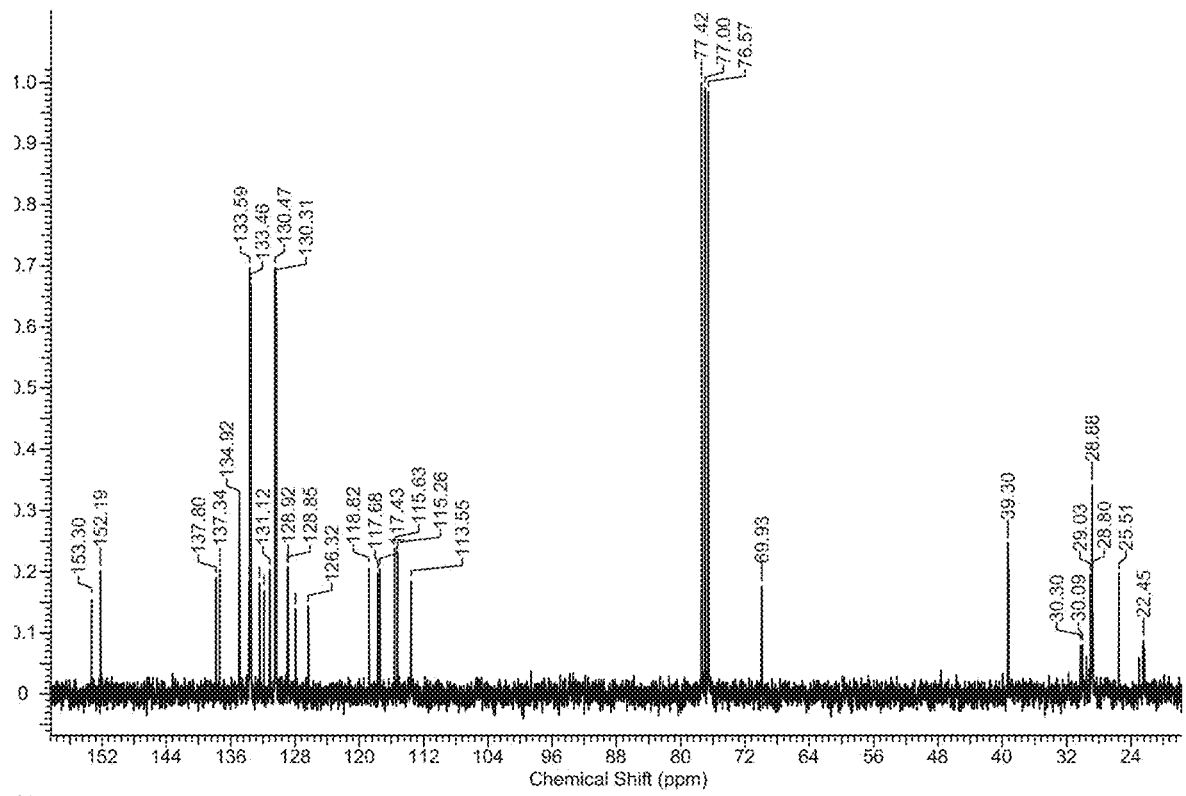
Figure 2:
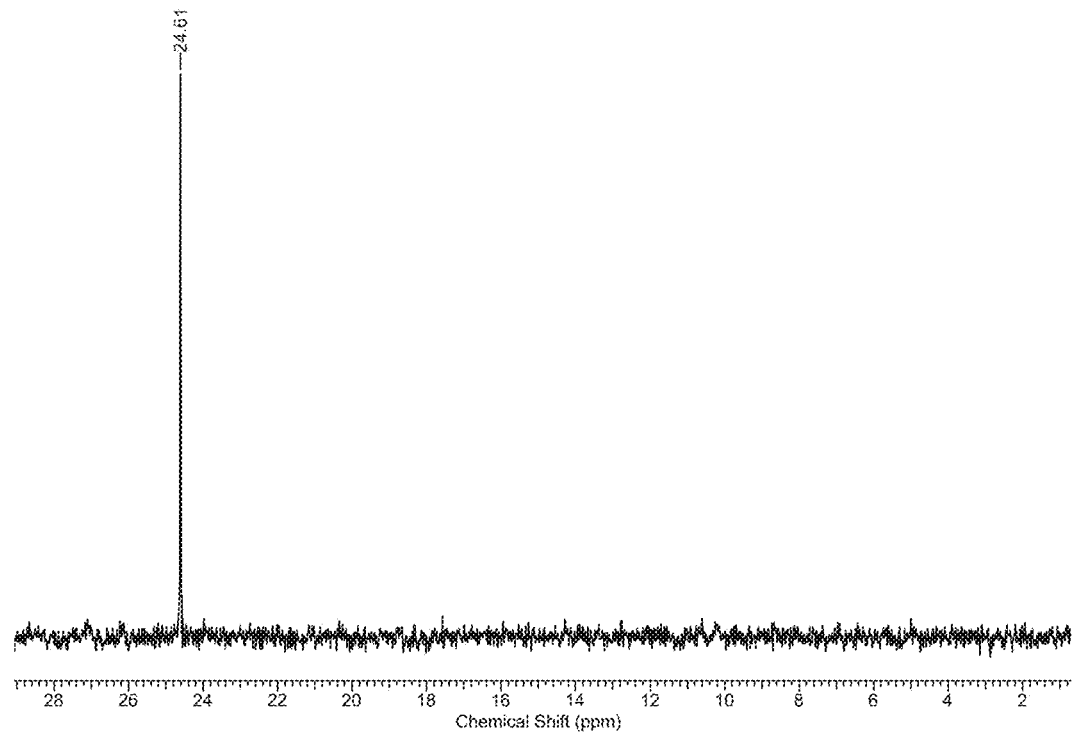
Figure 2:
Figure 2:
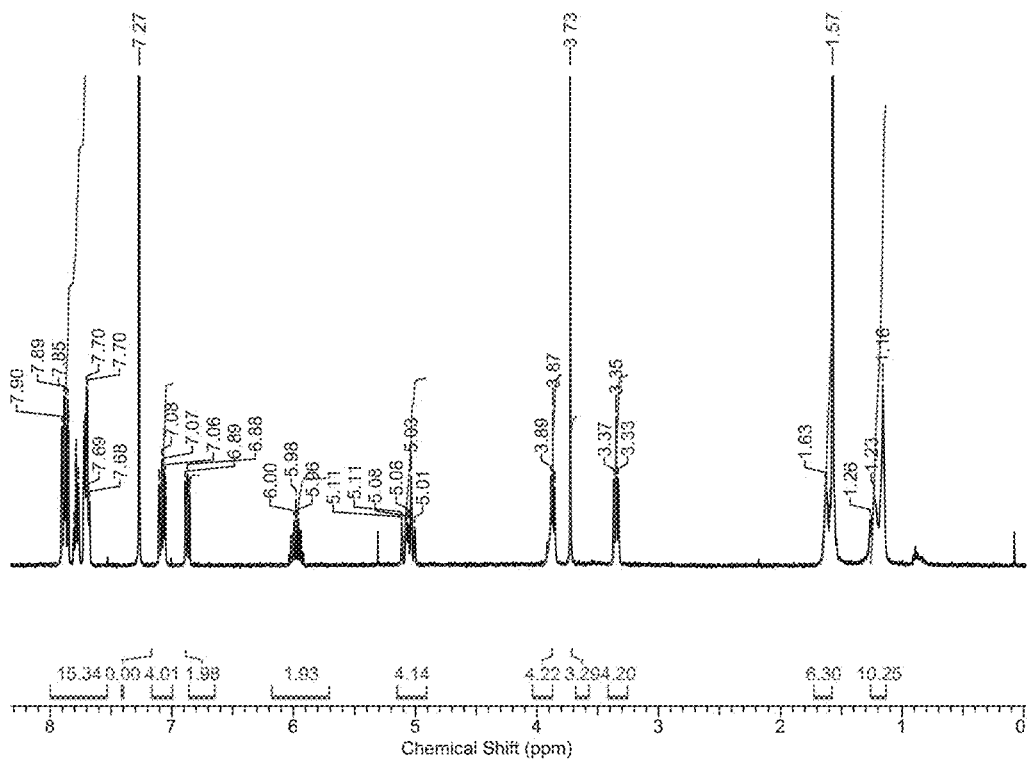
Figure 2:
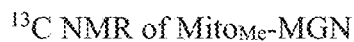
Figure 2:
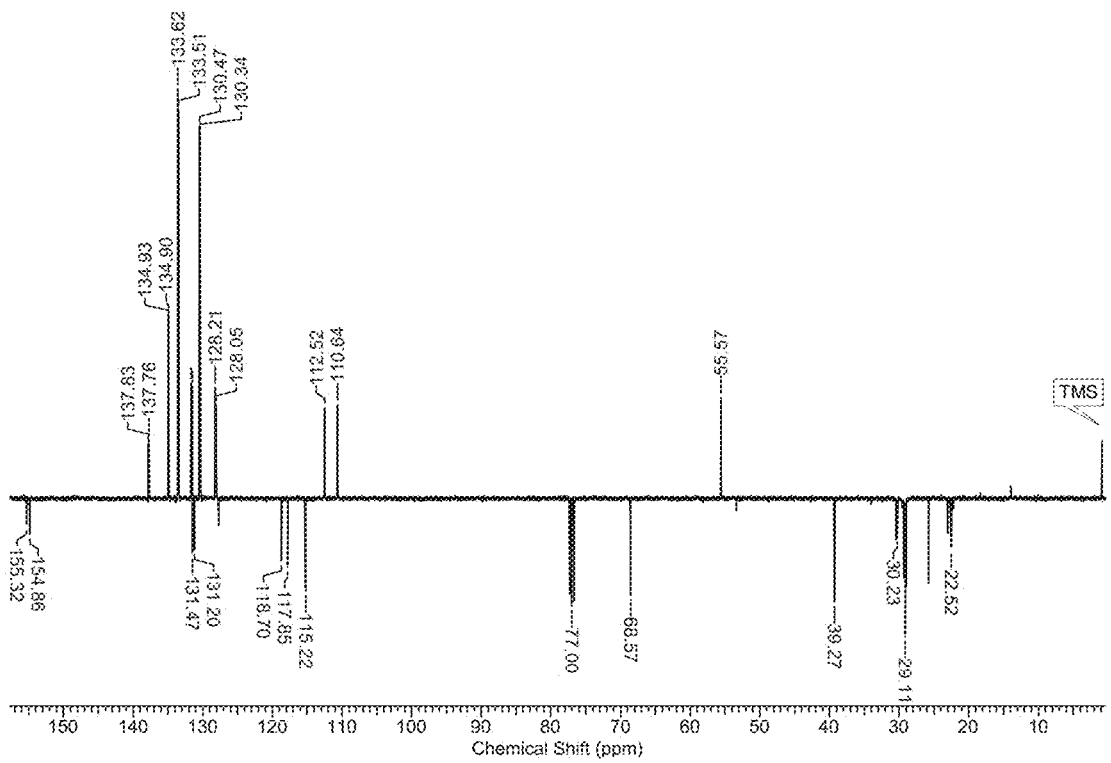

FIG. 2 shows the NMR of Mito-magnolol. HRMS calculated for Mito-magnolol C46H52O2P [MH]$^+$. 667.3699, found: 667.3699 31P (400.13 MHz, CDCl3) δ 24.27. 1H NMR (400.13 MHz, CDCl3) δ 7.80-7.65 (15H, m), 7.18-6.92 (611, m), 6.06-5.86 (211, m), 5.12-5.02 (4H, m), 3.99 (2H, t, J=6.5), 3.90-3.79 (2H, m), 3.37 (4H, t, J=6.9), 1.70-1.50 (4H, m). 1.39-1.13 (12H, m). (75 MHz, CDCl3) δ 153.3, 152.2, 137.8, 137.3, 133.9, 134.8, 133.6, 133.4, 132.4, 131.8, 131.1, 130.5, 130.3, 128.9, 128.8, 127.9, 126.3, 118.8, 117.7, 117.4, 115.6, 115.3, 113.6, 69.9, 39.3, 39.2, 30.3, 30.1, 29.0, 28.8, 25.5, 23.2, 22.5, 22.4, 22.3.

Synthesis of Mito$_{Me}$-magnolol. Me-magnolol and DiMe-magnolol were prepared by reacting methyl iodide with magnolol in the presence of potassium carbonate in DMF. Williamson reaction of 2-O-methylmagnolol and 10-bromo-decyl-triphenylphosphonium bromide in the presence of potassium carbonate led to Mito$_{Me}$-magnolol (FIG. 12B). To a mixture of 2-O-methylmagnolol (0.3 g, 1 mmol) and anhydrous potassium carbonate (0.3 g, 2 mmol) in DMF (4 mL) was added 10-bromodecyltriphenylphosphonium bromide (0.6 g, I mmol). The mixture was stirred at 40° C. for 18 h. 20 mL of water was added and the product was extracted with $CH_2Cl_2$ (80 mL). The organic layer was dried over $Na_2SO_4$, and the solvent was removed under reduced pressure. The product is precipitated with $Et_2O$. Purification by flash chromatography ($CH_2Cl_2$ and $CH_2Cl_2$/EtOH) delivered the corresponding Mito$_{Me}$-magnolol as a white solid (0.5 g, 62% yield).

FIG. 2 shows the NMR of Mito$_{Me}$-magnolol. HRMS calculated for Mito$_{Me}$-MGN C47H54O2P [M]$^+$: 681.3856, found: 681.3857. 31P (400.13 MHz, CDCl3) δ 24.61. 1H NMR (400.13 MHz, CDCl3) δ 7.90-7.65 (15H1, m), 7.07 (4H, 2dd, J=2.3, 8.3; 2.1, 5.6), 6.87 (2d, 2H, J=5.6, 5.8), 6.04-5.92 (2H, m), 5.10-4.98 (4H, m), 3.91-3.85 (4H, m), 3.73 (3H, s), 3.41-3.35 (4H, m), 1.67-1.59 (6H, m), 1.25-1.10 (10H, m). 13C NMR (75 MHz, CDCl3) δ 155.3, 154.8, 137.8, 137.7, 134.93, 134.90, 133.6, 133.5, 131.7, 131.5, 131.4, 131.2, 130.5, 130.3, 128.2, 128.0, 118.7, 117.8, 115.3, 115.2, 112.5, 110.6, 68.6, 55.6, 39.3, 30.4 (d, J=15.4), 29.3, 29.1, 29.1, 29.0, 22.8 (d, J=45.5), 22.4 (d, J=4.5).

Figure 13:
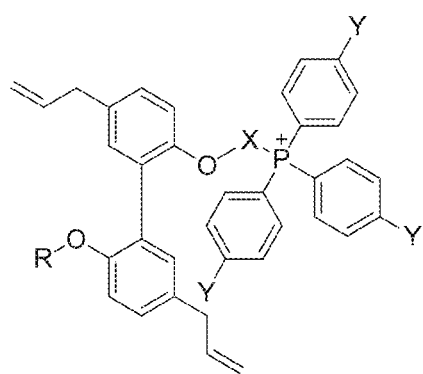
FIG. 13 demonstrates the generic structure of mito-magnolol.

FIG. 13 gives the generic structure of Mito-MGN derivatives that can be prepared using this procedure.

The MitoPEG-MGN compounds of the present invention can be synthesized according to the following reactions.

Scheme.

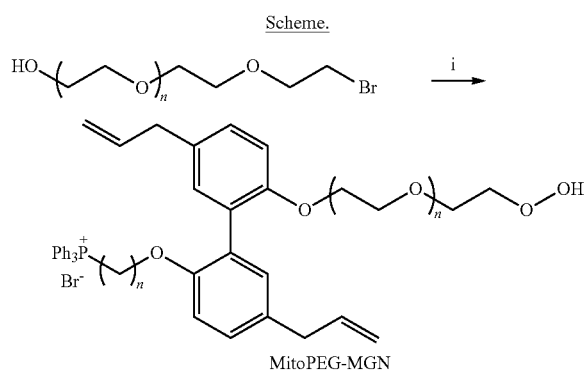

Reagents and conditions: i, Mito$_n$-MGN, K$_2$CO$_3$, DMF.

The MitoPhen-MGN compound of the present invention can be synthesized according to the following reactions.

Scheme.

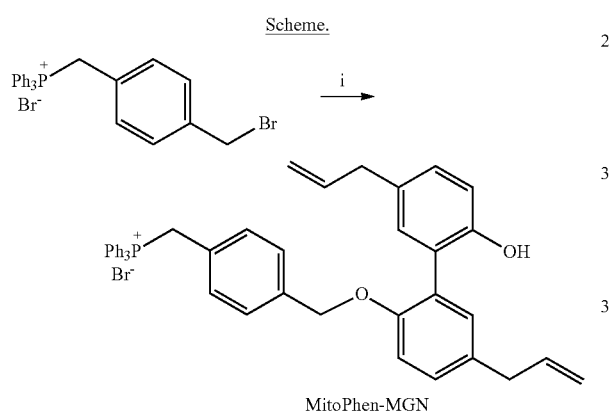

Reagents and conditions: i, MGN, K$_2$CO$_3$, DMF.

The MitoCy-MGN compound of the present invention can be synthesized according to the following reactions:

Scheme.

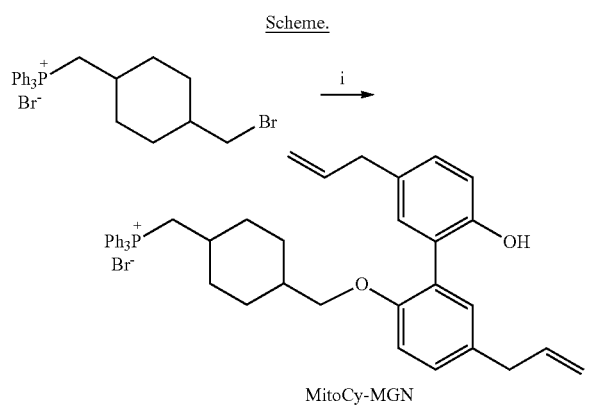

Reagents and conditions: i, MGN, K$_2$CO$_3$, DMF.

The Mito$_N$e-MGN compounds of the present invention can be synthesized according to the following reactions:

Scheme. Synthesis of Mito$_{Me}$-MGN derivatives.

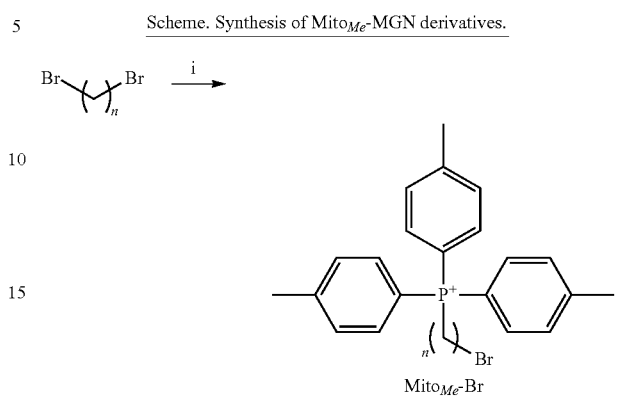

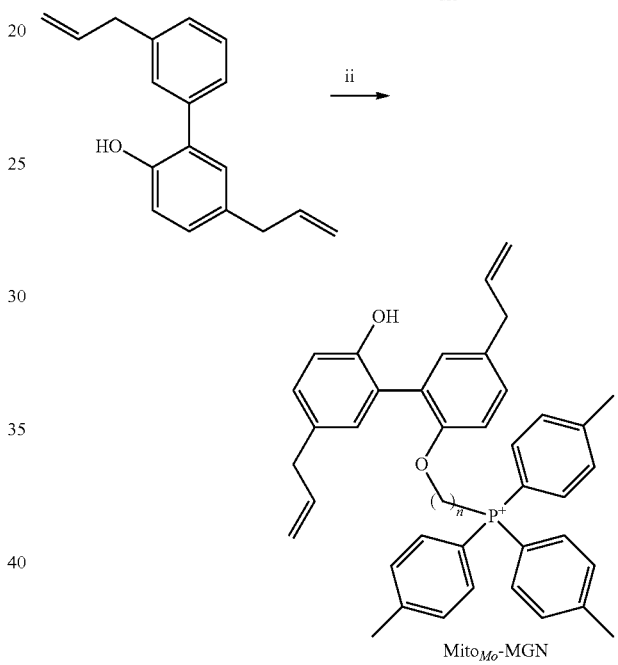

Reagents and conditions: i, tri-p-tolylphosphine, neat, 80° C., ii, Mito$_{nMe}$-Br, K$_2$CO$_3$, DMF.

The MitO$_{OMe}$-MGN compounds of the present invention can be synthesized according to the following reactions.

Scheme. Synthesis of Mito$_{OMe}$-MGN derivatives.

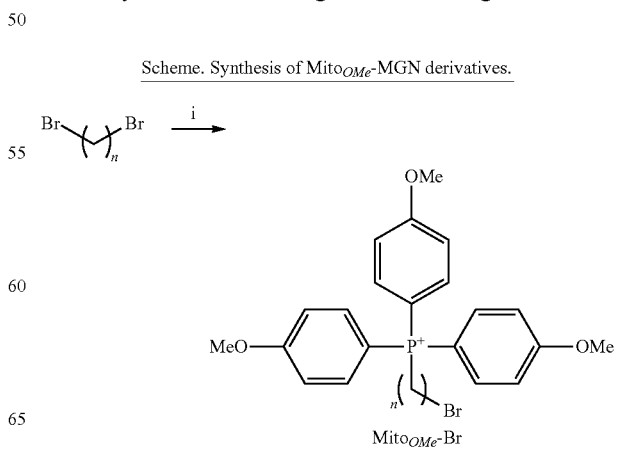

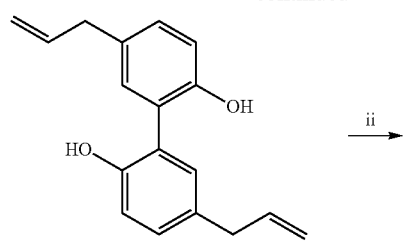

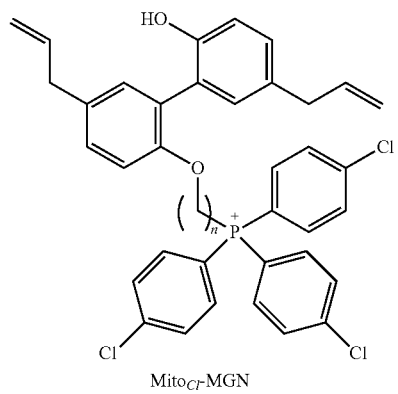

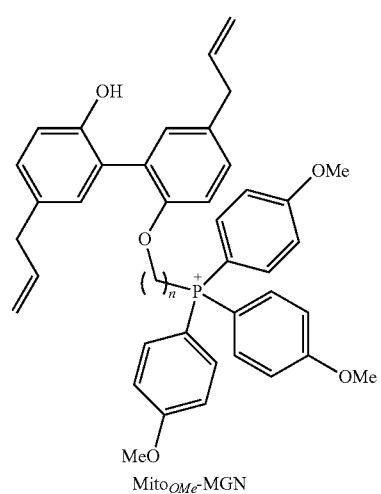

Reagents and conditions: i, tris-(4-methoxyphenyl)-phosphine, neat; ii, Mito$_{OMe}$-Br, K$_2$CO$_3$, DMF.

The Mito$_{Cl}$-MGN compounds of the present invention can be synthesized.

Scheme. Synthesis of Mito$_{Cl}$-MGN derivatives.

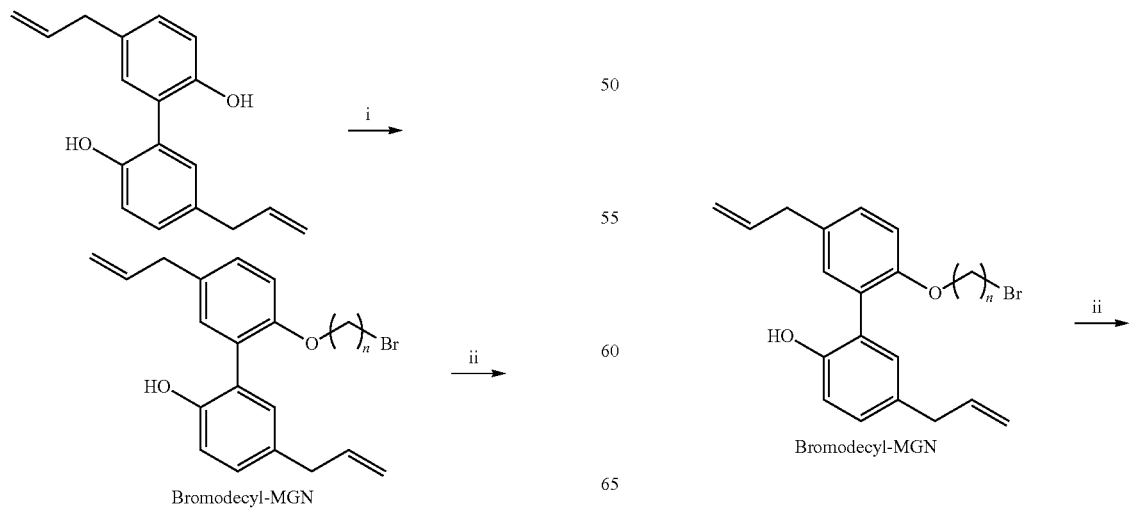

Reagents and conditions:
i, Br—(CH$_2$)$_n$—Br, K$_2$CO$_3$, DMF, rt.; ii, tris-(4-clhorophenyl)-phosphine, toluene, reflux.

The Mito$_{CF3}$-MGN compounds of the present invention can be synthesized according to the following reactions.

Scheme. Synthesis of Mito$_{CF3}$-MGN derivatives.

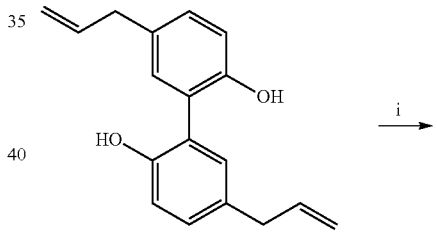

-continued

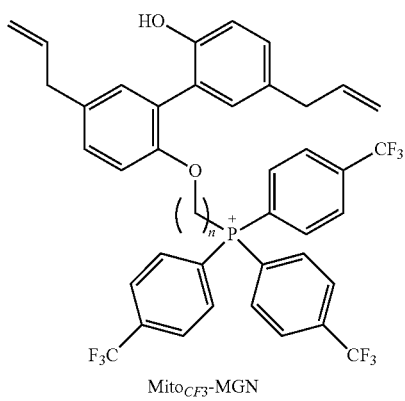

Mito$_{CF3}$-MGN

Reagents and conditions:
i, Br—(CH$_2$)$_n$—Br, K$_2$CO$_3$, DMF, rt., 33%; ii, tris-[4-(trifluoromethyl)phenyl]-phosphine, toluene, reflux.

The Mito$_n$-MGN2 compounds of the present invention can be synthesized according to the following reactions:

Scheme. Synthesis of Mito$_n$-MGN2 derivatives.

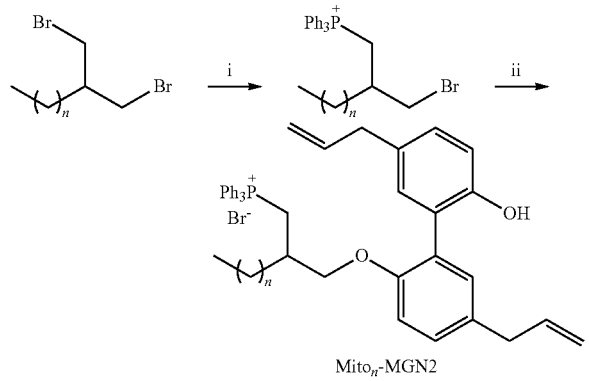

Mito$_n$-MGN2

Reagents and conditions: i, PPh$_3$, neat; ii, Magnolol, K$_2$CO$_3$, DMF, 40° C.

Figure 3:
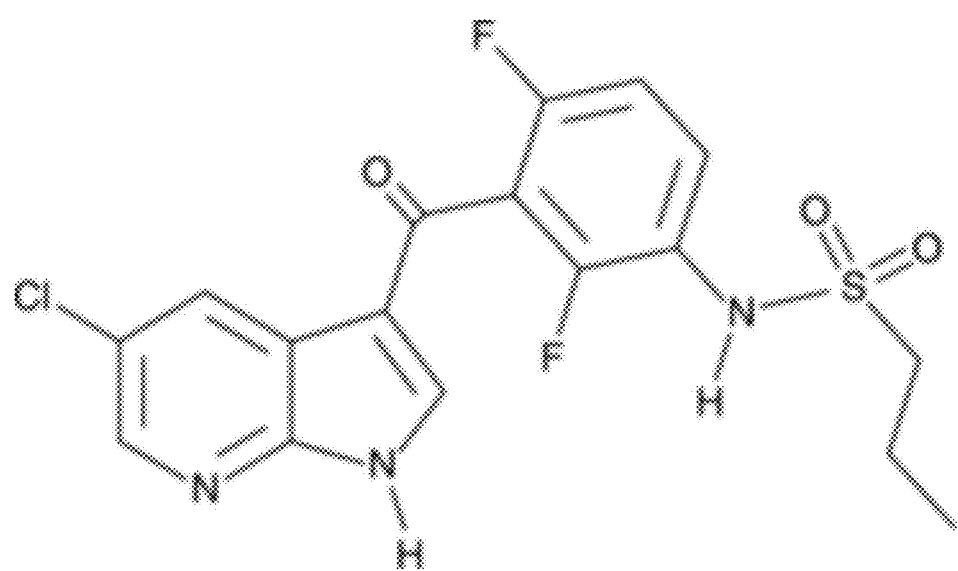
FIG. 3 shows the chemical structure of PLX4720 BRAF inhibitor. (00301 FIG. 4 demonstrates the effects of PLX4720 on proliferation of wild type UACC-62-WT cells and UACC-62 resistant to PLX4720 (UACC-62-R) cells. UACC-62-WT cells (A) or UACC-62-R cells (B) were treated with PLX4720 as indicated. Cell proliferation was monitored in real time with the continuous presence of indicated treatments until the end of each experiment. (C) Representative images shown are the segmentation of phase contrast images (segmentation mask illustrated in black). (D) The cell confluence (as control groups reach 95% confluency) is plotted against concentration of PLX4720 inhibitor. Dashed lines represent the fitting curves used to determine the $IC_{50}$ values. (E) A two-dimensional map shows the bioenergetics in WT (■) and kinase inhibitor resistant (○) cells treated with vehicle (black) or Mito-MGN (blue). (F) The effect of Mito-MGN (0.2 μM) on mitochondrial complex I and II activities (oxygen consumption rate, OCR) is shown for wild-type (red) and resistant UACC-62 (blue) melanoma cells.

Generation of PLX4720-resistant melanoma cell line. Mutations in the BRAF kinase, especially the mutation BRAFV600E, contribute to melanoma. This mutation is not effectively targeted by inhibitors of wild type BRAF. PLX4720 (FIG. 3) has been used as a highly selective inhibitor of BRAFV600E (or also Raf Kinase inhibitor V). PLX4720 was found to be much less effective against wild type BRAF and induces cell cycle arrest and apoptosis in melanoma cells expressing BRAF mutation.

Figure 4:
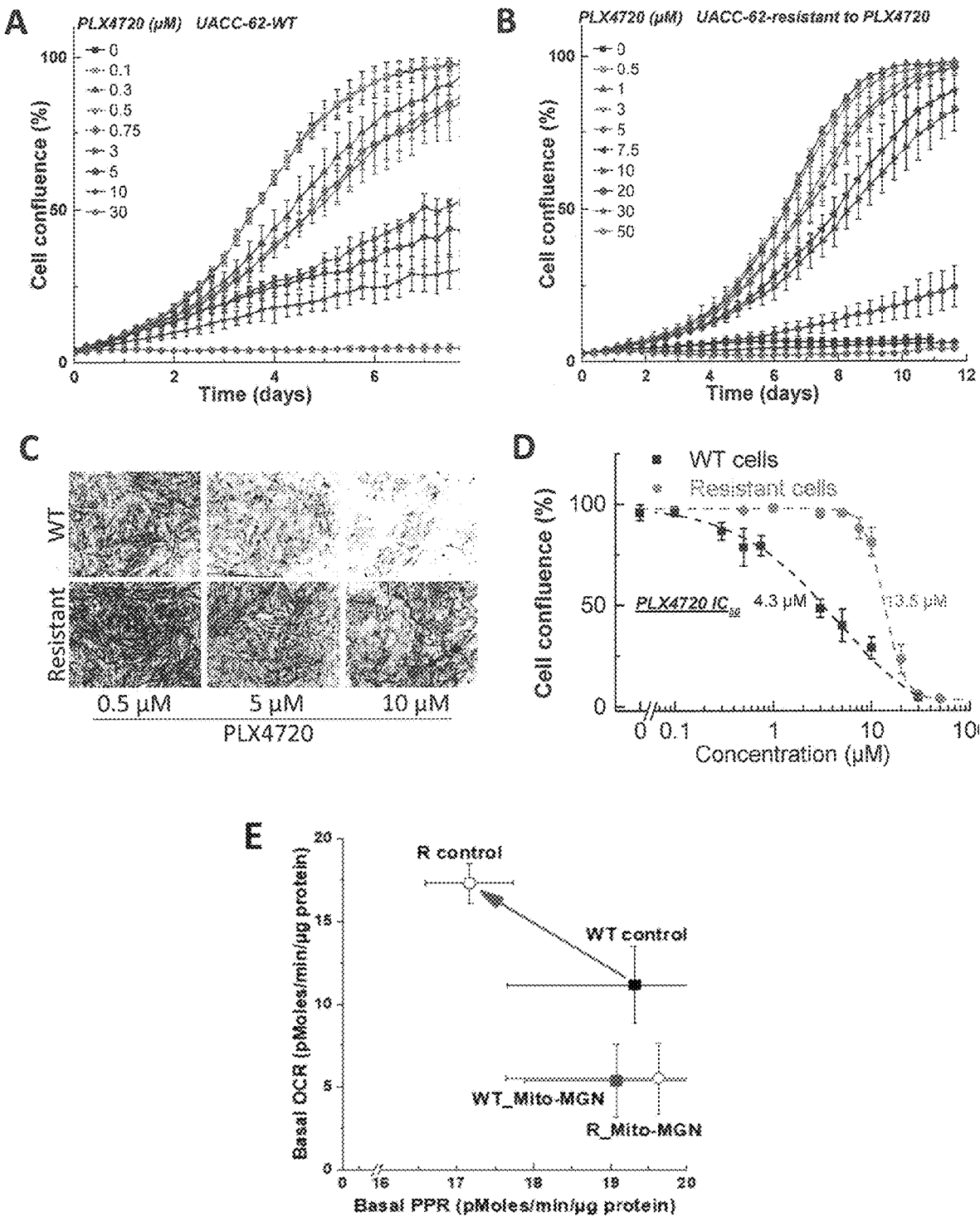
Figure 4:
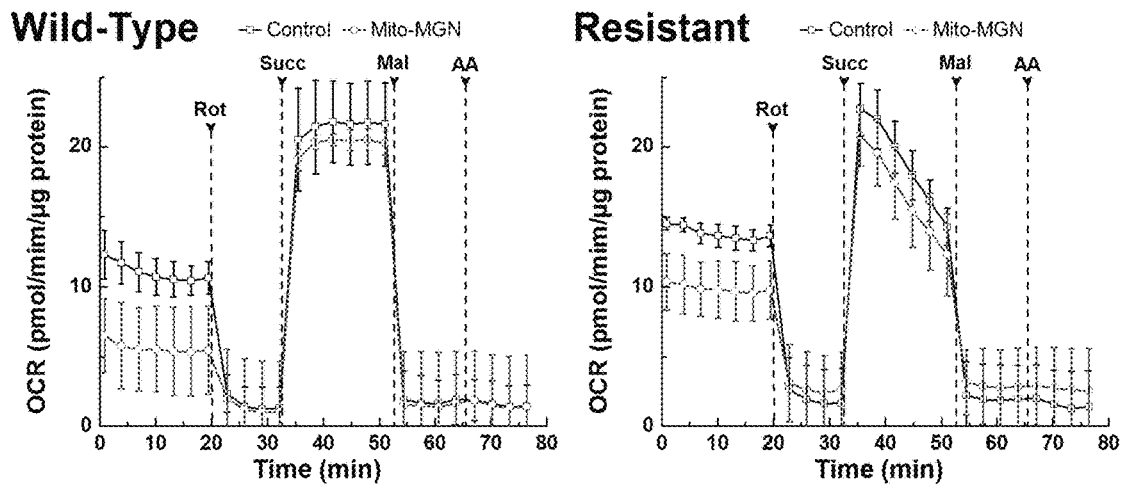

To establish PLX4720-resistant melanoma cell line. UACC-62 cells (ATCC) were continuously exposed to increasing concentrations of PLX4720 (1-20 µM) for six months until the logarithmic growth resumed. PLX4720-containing media were replaced twice a week. Resistant cell line (UACC-62R) was maintained in routine culture in the presence of 20 µM PLX4720. FIGS. 4A and 4B show the effect of PLX4720 on proliferation of UACC-62-WT and UACC-62-R cells. FIG. 4C shows the phase contrast images obtained after six days of treatment with 0.5-10 µM PLX4720 of the WT and resistant cells. As can be seen, there are considerably fewer WT cells compared to resistant cells in the presence of 10 µM PLX4720. FIG. 4D shows the IC$_{50}$ values (concentration at which 50% of cell proliferation is inhibited). These results clearly show the difference in sensitivity of UACC-62-WT and UACC-62-resistant cells to PLX4720.

Metabolic reprogramming in drug-resistant melanoma cells: Enhanced OXPHOS. Melanoma cells harboring BRAF oncogenic mutations use aerobic glycolysis (the Warburg effect) to meet their energy demands. However, cells with acquired resistance to BRAF inhibitors exhibit metabolic reprogramming, i.e., decreased glycolysis and a compensatory activation of mitochondrial OXPHOS (FIG. 4E, red arrow from WT to R). One reason for the acquired resistance to PLX4720 is the adaptive change from glycolysis to OXPHOS. The two-dimensional map of oxygen consumption rate (OCR) and extracellular acidification rate (ECAR), quantified as proton production rate (PPR), shows a ~55% increase in OCR and an 11% decrease in PPR, in UACC-62-R cells (FIG. 4E). Mito-MGN treatment minimally affected glycolysis in WT and resistant cells, while significantly inhibiting OXPHOS in both cell lines (FIG. 4E, blue).

Milo-MGN inhibits mitochondrial complex 1 activity. We used a Seahorse XF96 Analyzer to measure OCR, a readout of mitochondrial respiration, and ECAR, a surrogate marker for glycolysis, in real time. OCR is measured after adding substrates and inhibitors of complexes I-IV. In preliminary studies, Mito-MGN inhibited complex 1 activity in both WT and resistant cells (FIG. 4F). The IC$_{50}$ to inhibit complex I-mediated respiration (1 h Mito-MGN treatment) was 0.35 µM for UACC-62-WT cells, and 0.66 µM for UACC-62-R.

Figure 5:
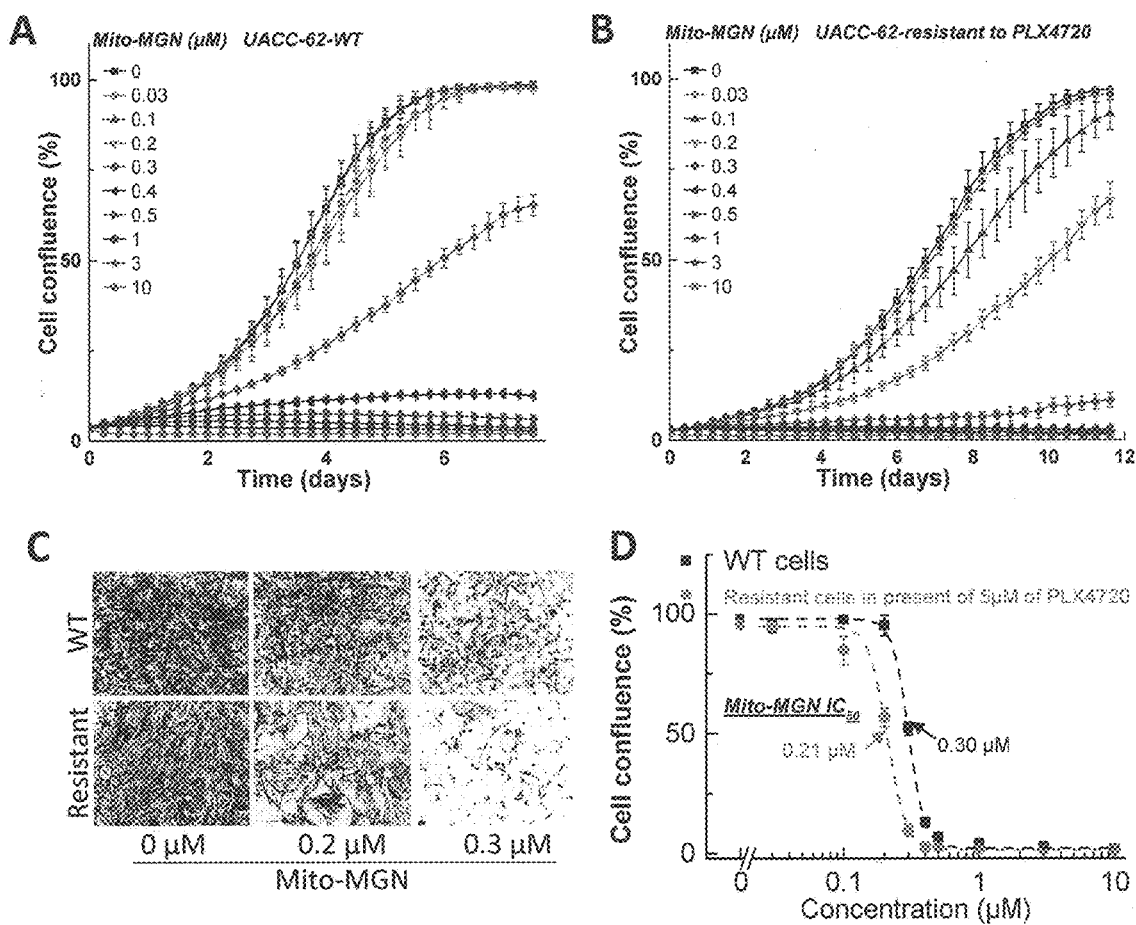
FIG. 5 demonstrates the effect of Mito-MGN on proliferation of UACC-62-WT cells and UACC-62-R cells. UACC-62-WT cells (A) or UACC-62-R cells (B) were treated with Mito-MGN as indicated. Cell proliferation was monitored in real time with the continuous presence of indicated treatments until the end of each experiment. (C) Representative images shown are the segmentation of phase contrast images (segmentation mask illustrated in black). (D) The cell confluence (as control groups reach 95% confluency) is plotted against Mito-MGN concentration Dashed lines represent the fitting curves used to determine the $IC_{50}$ values.

Mito-magnolol inhibits proliferation of both wild type and drug resistant melanoma cells. FIGS. 5A and 5B show the effect of Mito-magnolol on proliferation of UACC-62-WT and UACC-62-R cells. Cell proliferation was monitored in real time for cells incubated continuously under treatment conditions as shown. FIG. 5C shows the phase contrast images obtained after six days of treatment of WT and PLX4720-resistant cells in the presence of 0.1-0.3 µM of Mito-magnolol. As can be seen, both cell lines were exquisitely sensitive to Mito-magnolol treatment. FIG. 5D shows the IC$_{50}$ values of Mito-magnolol in WT and resistant cells. Results show that Mito-magnolol is effective in inhibiting the proliferation of drug resistant melanoma cells (FIG. 5).

Mito-magnolol inhibitory effect in drug resistant melanoma cells was a totally unexpected result Melanoma cells use metabolic reprogramming as a survival mechanism. Melanoma cells harboring BRAF mutations or BRAFV600E melanomas use aerobic glycolysis (the Warburg effect) to meet their energetic demands. Selective inhibitors of BRAF mutation (e.g., vemurafenib or PLX4032) that inhibit glycolysis cause a compensatory activation of oxidative metabolism, stimulating energy production through mitochondrial oxidative phosphorylation. It is believed that this adaptive change—from glycolysis to OXPHOS—is one of the reasons for the acquired resistance to vemurafenib. The vemurafenib-resistant melanoma cells exhibited increased oxidative stress and reactive oxygen species. One of the new strategies that was proposed to enhance the killing of vemurafenib-resistant cells involved the use of pro-oxidants or pro-oxidative drugs such as elesclomal (22). It was also suggested that mitochondrial pro-oxidants may have a clinical potential for treatment of drug resistant melanomas. Antioxidants (compounds or drugs that quench formation of oxidants and reactive oxygen species) reversed the effect of pro-oxidative drugs in vemurafenib-resistant melanoma cells.

Mito-magnolol is a structurally modified analog of magnolol, a naturally occurring bioactive polyphenol that has been shown to have an antioxidative and anti-inflammatory property (23,24). Mito-magnolol is synthesized by conjugating a triphenylphosphonium moiety to the phenolic hydroxyl group of magnolol. Magnolol elicits antioxidant behavior in both chemical and cellular systems. Magnolol inhibits oxidant-induced lipid peroxidation, a pro-oxidative process. Previously, it has been shown that Mito-Q, a triphenylphosphonium based modification of a naturally occurring antioxidant co-enzyme Q, shows potent antioxidant property in mitochondria (25).

Mito-magnolol stimulates ROS and causes oxidation of mitochondrial antioxidative enzyme in BRAFV600E inhibitor-resistant melanoma cells. UACC-62-WT and UACC-62-R cells were preincubated with Mito-magnolol for 24 h and then treated with hydroethidine. Cell lysates were analyzed by HPLC and the superoxide-specific hydroxylation product (2-OH-E$^+$) and other two-electron and one-electron oxidation products (E$^+$ and E$^+$-E+) were determined.

Figure 6:
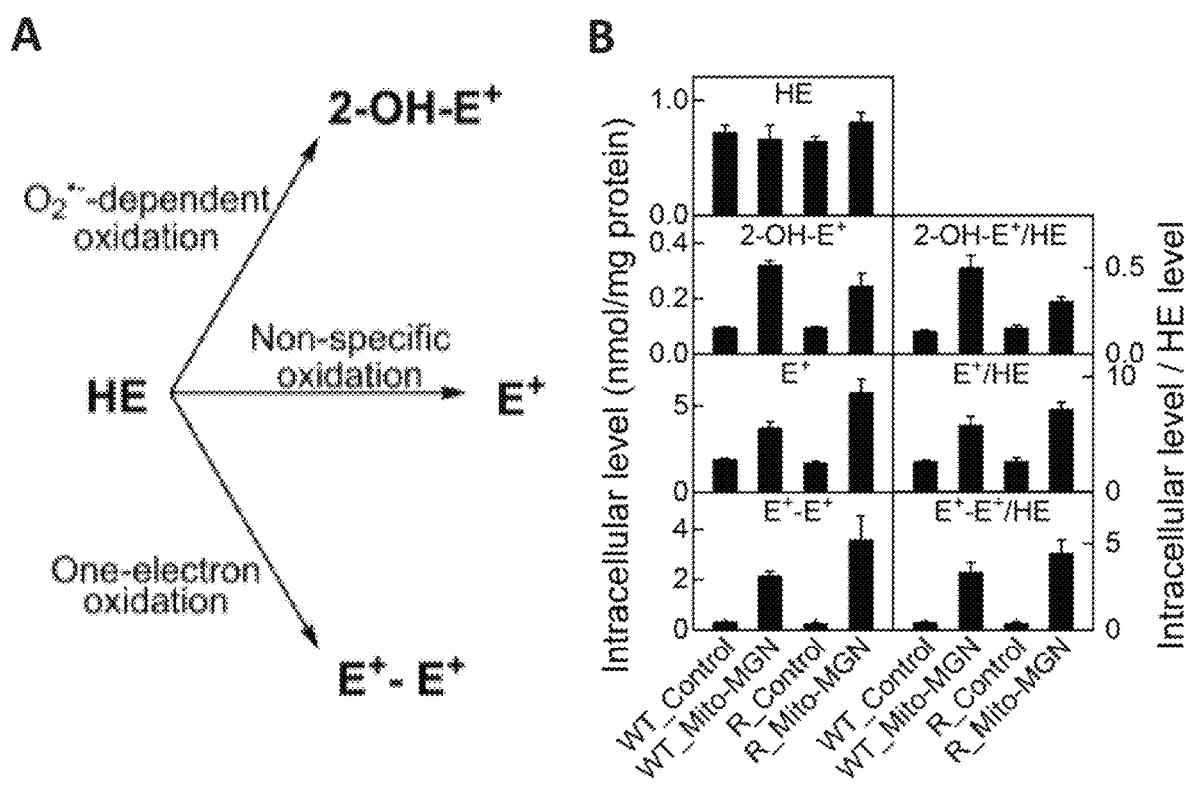
FIG. 6 shows Mito-MGN effects on oxidant production in UACC-62-WT cells and UACC-62-R cells. (A) Scheme of ROS-dependent oxidation of hydroethidine (HE) probe. (B) Effect of Mito-MGN on different oxidation products of HE probe.

As shown in FIG. 6, Mito-magnolol induces significantly higher amount of 2-OH-E$^+$ and E$^+$ and E$^+$-E$^+$ in both WT and resistant cells. Hydroethidine (IE) was used to measure intracellular $O_2^{\bullet-}$ formation. 2-Hydroxyethidium (2-OH—E$^+$), the diagnostic marker product of $O_2^{\bullet-}$/HE reaction (FIG. 6A) increased in Mito-MGN treated melanoma cells (FIG. 6B). In addition, Mito-MGN induced the iron or peroxidase-dependent oxidation of HE as evidenced by enhanced intracellular formation of E$^+$-E$^+$ and E$^+$ (FIG. 6B).

Figure 7:
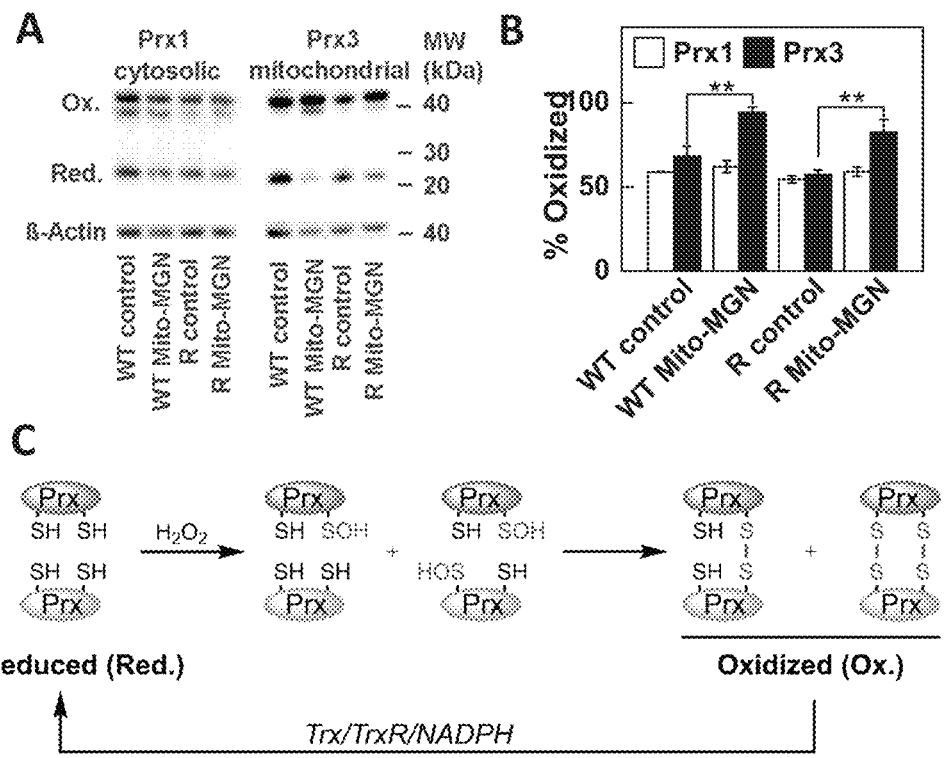
FIG. 7 shows that Mito-MGN induces the oxidation of mitochondria- and peroxide-specific antioxidative enzyme (Prx3) in wild type (WT) and resistant (R) melanoma cells. (A) Western blot show the redox status of cytosolic (Prx1) and mitochondrial (Prx3) peroxiredoxins. (B) Quantitative analysis of the extent of Prx1 and Prx3 oxidation. Values are mean±SD, n=3. **, P≤0.01. (C) Scheme showing the pathways controlling the redox state and covalent dimer formation of peroxiredoxins in cells.

Peroxiredoxins (Prx) are abundant endogenous intracellular thiol peroxidases that act as compartment-specific sensors of hydrogen peroxide ($H_2O_2$) in mitochondrial (Prx3) and cytosolic (Prx1) compartments (62-64). Prxs rapidly react with $H_2O_2$ ($k=10^6$-$10^7$ M$^{-1}$s$^{-1}$) (64, 65). Prx3 accounts for nearly 90% of mitochondrial peroxidase activity (64, 66). Experiments indicated that Mito-MGN stimulated the oxidation of mitochondrial Prx3, while cytosolic Prx1 was largely unaffected (FIGS. 7A and 7B) in both WT and resistant melanoma cells. FIG. 7C shows the scheme of oxidation of reduced thiol group in Prx3 to an oxidized form in the dimeric form.

Figure 8:
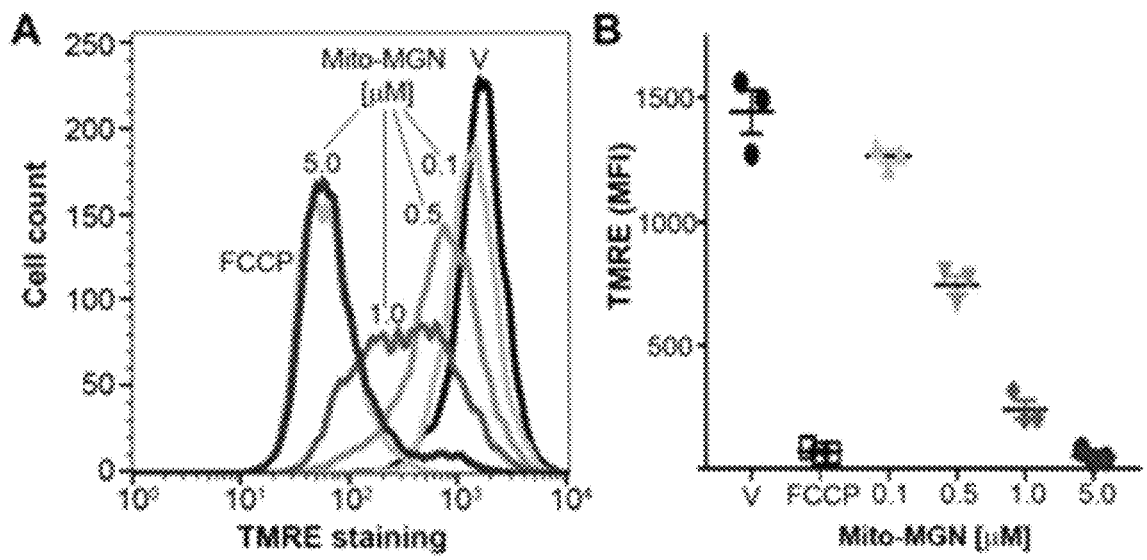
FIG. 8 demonstrates mitochondrial depolarization in response to Mito-MGN. (A) Representative TMRE quantification using flow cytometry. (B) Mean fluorescence intensity (MFI) of TMRE in Mito-MGN-treated and vehicle (V)-treated UACC-62-WT cells. Values are mean±SEM, n=3

Not to be bound by any theory, but it is believed that Mito-MGN-induced ROS halts melanoma proliferation through induction of mitophagy. ROS at high μM concentrations have detrimental effects on lipids, proteins, and DNA, whereas at nM concentrations, ROS exerts potent signaling effects (11, 41, 65). We postulate that OXPHOS inhibition by Mito-MGN increases ROS levels, which in turn stimulates mitophagy. To test this hypothesis, we will use an iterative approach to first measure mitochondrial membrane damage, followed by the parallel examination of molecular markers and phagolysome activation needed for mitophagy. Tetramethylrhodamine ethyl ester (TMRE) is retained in metabolically active mitochondria and released into the cytosol and extracellular space of cells with depolarized/damaged mitochondria (67), as illustrated in our recent paper using related mitochondria-targeted agents (12). Pilot experiments indicate that Mito-MGN dose dependently decreases mitochondrial membrane potential in treated UACC-62 cells (FIGS. 8A and 8B).

Figure 9:
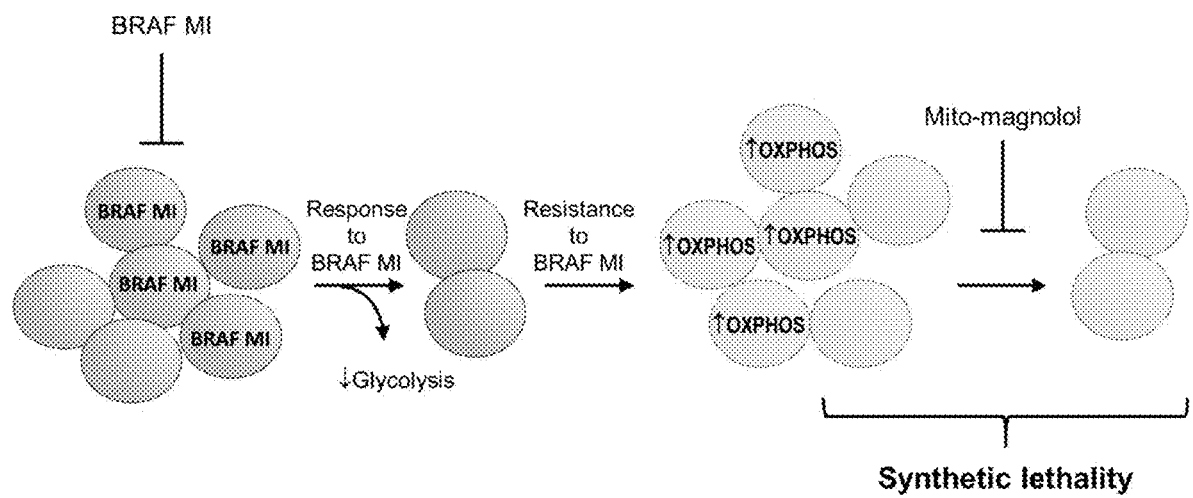
FIG. 9 is a schematic representation of Mito-magnolol inducing synthetic lethality to tumor cells resistant to kinase inhibitor (BRAF M I).
Figure 10:
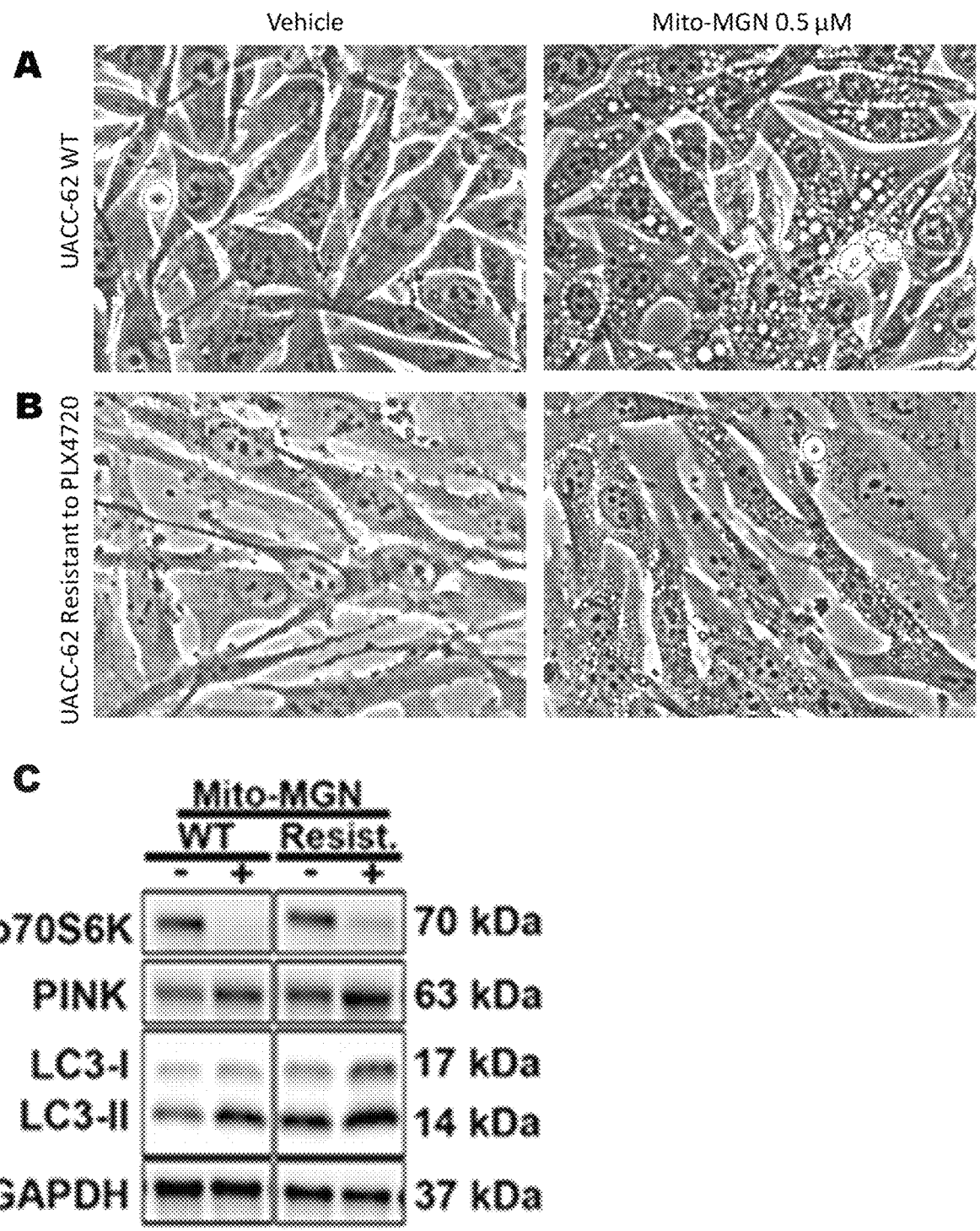
FIG. 10 shows photomicrographs and Western blot analysis of melanoma cells UACC-62-WT in the absence and presence of Mito-MGN (A), and UACC-62-R cells in the absence and presence of Mito-MGN (B). Autophagic vacuoles are seen in Mito-MGN-treated both wild type and resistant melanoma cells. (C) Western blot of cell cycle- and autophagy-regulated proteins in Mito-MGN treated melanoma cells. UACC-62-WT and UACC-62-R cells were incubated for 24 h with 0.5 μM Mito-MGN. Data are representative of 3 separate biological replicates.

Based on the results, we postulate a novel mechanism by which Mito-magnolol inhibits the proliferation of BRAFV600E inhibitor-resistant melanoma cells (FIG. 9). This is a specific example of synthetic lethality induced by Mito-magnolol. Initial studies reveal that the mechanism of inhibition of cell proliferation in Mito-magnolol-treated melanoma wild type and drug resistant cells involve autophagy as evidenced by the accumulation of vacuoles (FIGS. 10A and 10B) and induction of autophagy regulated proteins, such as LC3-II (FIG. 10C).

Synergy between Mito-magnolol and PD-1 blockade therapy. The interaction between programmed cell death (PD-1), a surface receptor expressed in activated T cells, and its ligand PD-L1 in antigen presenting cells (tumor cells) is responsible for evasion of tumor cells in humans. The idea that PD-1-PD-L1 blockade could improve the clinical outcome in patients potentially revolutionized personalized cancer therapy. Blocking PD-1 with PD-L1 monoclonal antibody (PD-L1 mAb) enhanced the tumor killing effects of T cells through increased recognition of tumor cells. PD-L1 mAb enhanced the mitochondrial oxidative metabolism and ROS in cytotoxic T cells (26).

Figure 11:
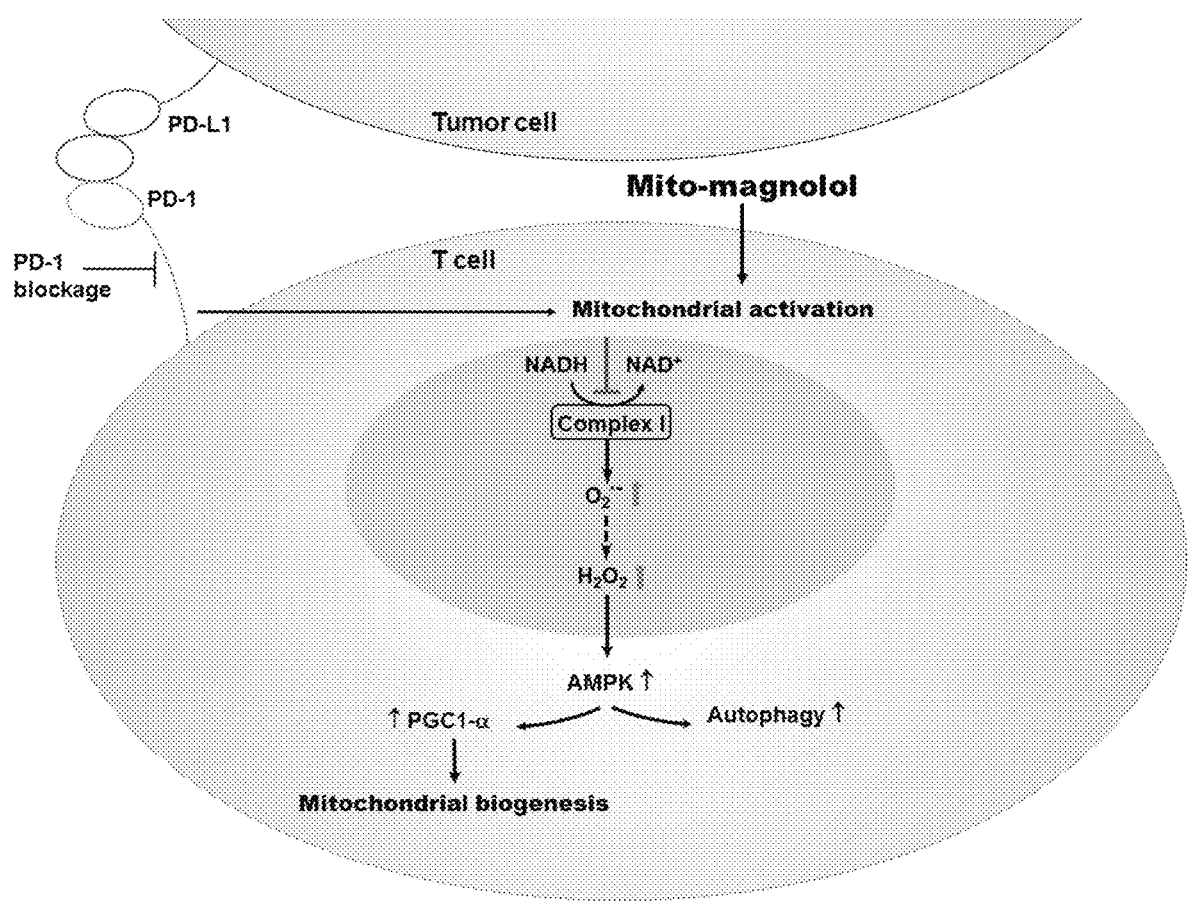
FIG. 11 shows a proposed mechanism of activation of mitochondrial biogenesis by Mito-magnolol in T cells: Enhanced tumor cell cytotoxicity.

Although PD-1 blockade immunotherapy has revolutionized treatment of some cancers (melanoma, lung cancer), many patients did not respond favorably to immunotherapy. The lack of response was attributed to an overall exhaustion of T cells (in the immunosuppressive tumor microenvironment) caused by mitochondrial dysfunction and decreased energy metabolism. During PD-1 blockade therapy, it was shown that tumor reactive CD8+ T cells exhibited higher mitochondrial membrane potential and ROS. It was suggested that mitochondrial stimulation in T cells likely supports the antitumor activity (26). It was rationalized that unresponsive T cells may be activated using combinatorial therapies involving PD-1 blockade therapy and mitochondrial ROS stimulators. Our surprising discovery-Mito-magnolol-mediated chemotherapy in drug resistant melanoma—in combination with PD-1 blockade therapy, can help overcome the unresponsiveness of immunotherapy by stimulating its mitochondrial ROS and the key energy sensors, e.g., AMP-activated protein kinase (AMPK). A hypothetical scheme combining PD-1 blockade and mitochondrial OXPHOS and ROS stimulators (Mito-magnolol) in activating and stimulating mitochondrial biogenesis in T cells (FIG. 11), thereby enhancing their tumor cell cytotoxicity.

REFERENCES EXAMPLE 1

1. Kim H K, Noh Y H, Nilius B, Ko K S, Rhee B D, Kim N, Han J. Current and upcoming mitochondrial targets for cancer therapy. Semin Cancer Biol. 2017 December; 47:154-67.
2. Gottesman M M 1, Fojo T, Bates S E. Multidrug resistance in cancer: role of ATP-dependent transporters. Nat Rev Cancer. 2002 January; 2(1):48-58.
3 Haq R, Fisher D E, Widlund H R. Molecular pathways: BRAF induces bioenergetic adaptation by attenuating oxidative phosphorylation. Clin Cancer Res. 2014 May 1; 20(9). 2257-63.
4. Berridge M V, Tan A S. Effects of mitochondrial gene deletion on tumorigenicity of metastatic melanoma: reassessing the Warburg effect. Rejuvenation Res. 2010 April-June; 13(2-3):139-41.

5. Pollak M. Targeting oxidative phosphorylation: why, when, and how. Cancer Cell. 2013 Mar. 18; 23(3):263-4.
6. Vazquez F, Lim J H, Chim 1-1, Bhalla K, Gimun G, Pierce K, Clish C B, Granter S R, Widlund H R, Spiegelman B M, Puigserver P. PGC1α expression defines a subset of human melanoma tumors with increased mitochondrial capacity and resistance to oxidative stress. Cancer Cell. 2013 Mar. 18; 23(3):287-301.
7. Haq R, Shoag J, Andreu-Perez P, Yokoyama S, Edelman H, Rowe G C, Frederick Dr, Hurley A D, Nellore A, Kung A L, Wargo J A, Song I S, Fisher D E, Arany Z, Widlund H R. Oncogenic BRAF regulates oxidative metabolism via PGC1α and MITF. Cancer Cell. 2013 Mar. 18; 23(3): 302-15.
8. Fanciulli M, Bruno T, Giovannelli A. Gentile F P, Di Padova M, Rubiu O, Floridi A. Energy Metabolism of Human LoVo Colon Carcinoma Cells: Correlation to Drug Resistance and Influence of Lonidamine. Clin Cancer Res. 2000 April: 6(4):1590-7.
9. Vellinga T T, Borovski T, de Boer V C, Fatrai S, van Schelven S, Trumpi K. Verheem A, Snoeren N, Emmink B L, Koster J, Rinkes I H, Kranenburg O. SIRT1/PGC1α-Dependent Increase in Oxidative Phosphorylation Supports Chemotherapy Resistance of Colon Cancer. Clin Cancer Res. 2015 Jun. 15; 21(12):2870-9.
10. Tan Z, Luo X, Xiao L, Tang M, Bode A M. Dong Z, Cao Y. The Role of PGC1α in Cancer Metabolism and its Therapeutic Implications. Mol Cancer Ther. 2016 May: 15(5):774-82.
11. Ippolito L, Marini A, Cavallini L, Morandi A, Pietrovito L, Pintus G, Giannoni E, Schrader T, Puhr M, Chiarugi P, Taddei M L. Metabolic shift toward oxidative phosphorylation in docetaxel resistant prostate cancer cells Oncotarget. 2016 Sep. 20; 7(38):61890-904.
12. Petrylak D P, Tangen C M, Hussain M H, Lara P N Jr. Jones J A, Taplin M E, Burch P A, Berry D, Moinpour C, Kohli M, Benson M C, Small E J, Raghavan D, Crawford E D. Docetaxel and estramustine compared with mitoxantrone and prednisone for advanced refractory prostate cancer. N Engl J Med. 2004 Oct. 7; 351(15):1513-20.
13. Gottschalk S, Anderson N, Hainz C, Eckhardt S G, Serkova N J. Imatinib (ST1571)-mediated changes in glucose metabolism in human leukemia BCR-ABL-positive cells. Clin Cancer Res. 2004 Oct. 1; 10(19):6661-8.
14. Cheng G, Zielonka J, Dranka B P, McAllister D, Mackinnon A C Jr, Joseph J, Kalyanaraman B. Mitochondria-targeted drugs synergize with 2-deoxyglucose to trigger breast cancer cell death. Cancer Res. 2012 May 15; 72(10):2634-44.
15. Cheng G, Zielonka J, McAllister D, Tsai S, Dwinell M B, Kalyanaraman B. Profiling and targeting of cellular bioenergetics inhibition of pancreatic cancer cell proliferation. Br J Cancer. 2014 Jul. 8; 111(1):85-93.
16. Weinberg F, Hamanaka R, Wheaton W W, Weinberg S. Joseph J, Lopez M, Kalyanaraman B, Mutlu G M, Budinger G R, Chandel N S. Mitochondrial metabolism and ROS generation are essential for Kras-mediated tumorigenicity. Proc Natl Acad Sci USA. 2010 May 11:107 (19):8788-93.
17. Cheng G, Zielonka J, McAllister D M, Mackinnon A C Jr, Joseph J, Dwinell M B, Kalyanaraman B. Mitochondria-targeted vitamin E analogs inhibit breast cancer cell energy metabolism and promote cell death. BMC Cancer. 2013 Jun. 13; 13:285.
18. Asin-Cayuela J, Manas A R, James A M, Smith R A, Murphy M P Fine-tuning the hydrophobicity of a mitochondria-targeted antioxidant. FEBS Lett. 2004 Jul. 30; 571(1-3):9-16.
19. Zielonka J, Joseph J, Sikora A, Hardy M, Ouari O, Vasquez-Vivar J, Cheng G. Lopez M. Kalyanaraman B. Mitochondria-Targeted Triphenylphosphonium-Based Compounds: Syntheses, Mechanisms of Action, and Therapeutic and Diagnostic Applications. Chem Rev. 2017 Aug. 9; 117(15):10043-120.
20. Brunen D, Bernards R. Drug therapy: Exploiting synthetic lethality to improve cancer therapy. Nat Rev Clin Oncol. 2017 June; 14(6):331-2.
21. Kaelin W G Jr. The concept of synthetic lethality in the context of anticancer therapy. Nat Rev Cancer. 2005 September; 5(9):689-98.
22. Corazao-Rozas P, Guerreschi P, Jendoubi M, André F, Jonneaux A, Scalbert C, Gargon G, Malet-Martino M, Balayssac S, Rocchi S, Savina A, Formstecher P, Mortier L, Kluza J, Marchetti P. Mitochondrial oxidative stress is the Achille's heel of melanoma cells resistant to Braf-mutant inhibitor. Oncotarget. 2013 November; 4(11): 1986-98.
23. Chuang D Y, Chan M H, Zong Y, Sheng W, He Y, Jiang J H, Simonyi A, Gu Z, Fritsche K L, Cui J, Lee J C, Folk W R, Lubahn D B, Sun A Y, Sun G Y. Magnolia polyphenols attenuate oxidative and inflammatory responses in neurons and microglial cells. J Neuroinflammation. 2013 Jan. 29; 10:15. doi: 10.1186/1742-2094-10-15.
24. Tian Y, Feng H, Han L, Wu L, Lv H, Shen B. Li Z, Zhang Q, Liu G. Magnolol Alleviates Inflammatory Responses and Lipid Accumulation by AMP-Activated Protein Kinase-Dependent Peroxisome Proliferator-Activated Receptor α Activation. Front Immunol. 2018 Feb. 5; 9:147. doi: 10.3389/timmu 2018.00147. eCollection 2018.
25. Murphy M P, Smith R A Targeting antioxidants to mitochondria by conjugation to lipophilic cations. Annu Rev Pharmacol Toxicol. 2007, 47:629-56.
26. Chamoto K, Chowdhury P S, Kumar A, Sonomura K, Matsuda F, Fagarasan S, Honjo T. Mitochondrial activation chemicals synergize with surface receptor PD-1 blockade for T cell-dependent antitumor activity. Proc Natl Acad Sci USA. 2017 Jan. 31; 114(5):E761-E70.

Figure 14:
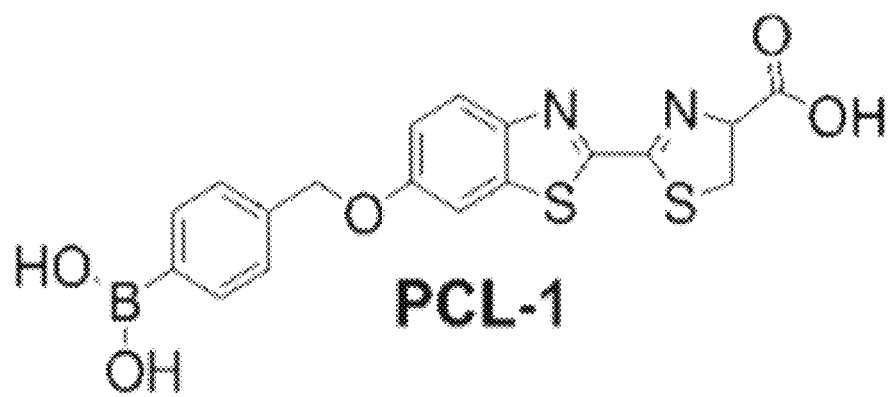
FIG. 14 shows the chemical structure of PCL-I molecular probe for oxidant detection in Vivo.

Example 2: In Vivo Efficacy and Molecular Mitochondrial Mechanism of Mito-MGN Effects on Melanoma Progression Not to be bound by any theory, but from the cell culture results, Mito-MGN seem to inhibit tumor bioenergetics, stimulate mitochondrial ROS and redox signaling, and mitigate tumorigenesis in human UACC-62 and B16 melanoma models. To investigate these effects in vivo on tumor growth, ROS formation, and mitophagy, we are using state-of-the-art analytical approaches, including micro-computed tomography (ICT), bioluminescence imaging (BLI) of a peroxycaged luciferin (PCL-1, FIG. 14) and a probe-free ex vivo cryogenic EPR technique (75, 76). Although new and improved fluorescent probes can detect specific ROS in cell culture systems, extrapolation of these assays to cancer xenografts has proven difficult (31, 50). Thus, our use of an ex vivo, low temperature, probe-free, EPR technique is vital for assessing oxidant formation and redox changes and metabolic reprogramming in tumor mitochondria.

The efficacy of Mito-MGN in a murine model of melanoma was tested using cells sensitive and resistant to BRAF inhibitors as tools to probe the anti-tumor effects of targeted OXPHOS inhibitors. Treatment of mice orthotopically engrafted with UACC-62-WT cells with 1 mg Mito-MGN, injected intratumorally in 50 µL, potently reduced tumor size as measured in vivo using µCT imaging (FIG. 15A) and ex vivo from excised tumors (FIG. 15B).

Figure 16:
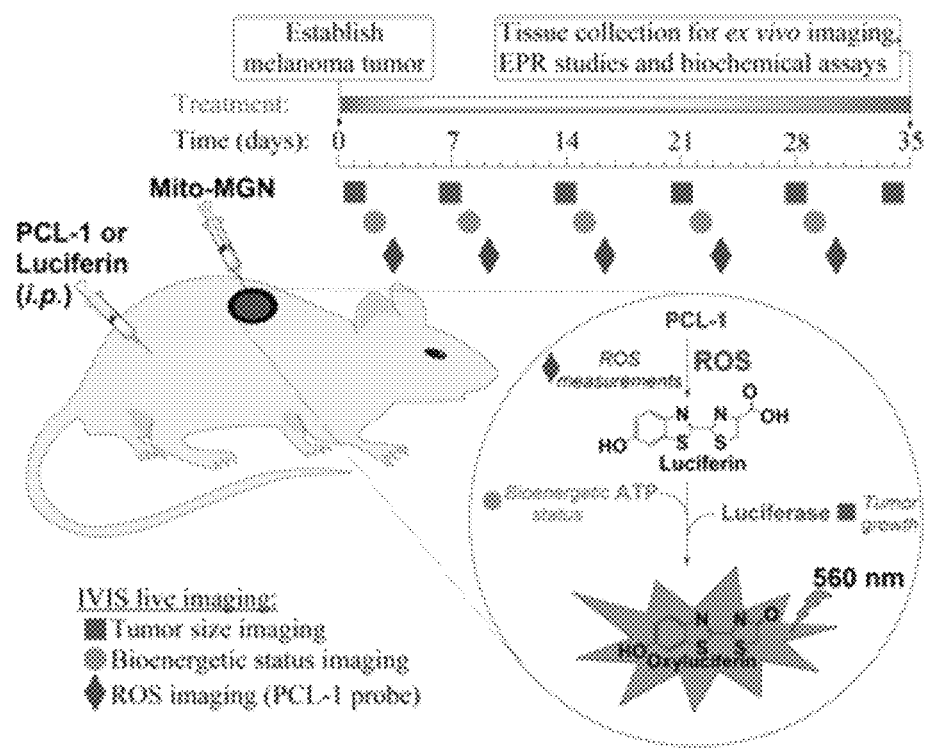
FIG. 16 depicts the protocol for in vivo bioluminescence imaging of tumor growth, bioenergetic status, and ROS in murine melanoma models.
Figure 17:
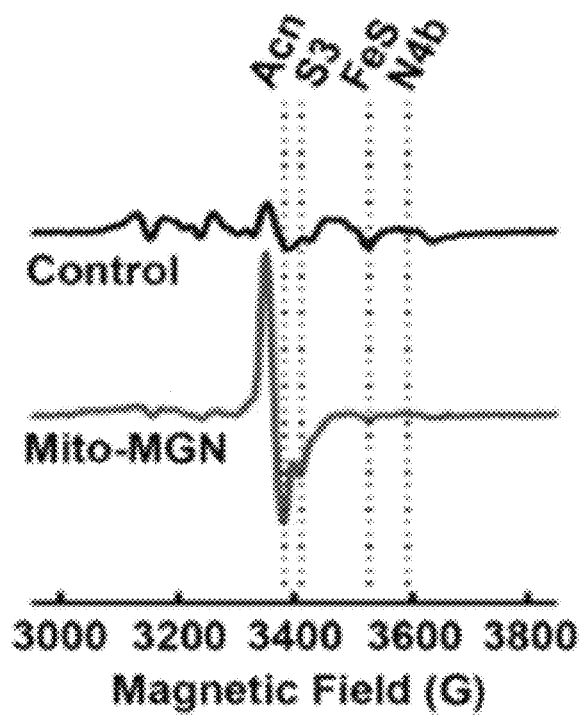
FIG. 17 demonstrates ex vivo EPR detection of oxidants in cancer. UACC-62-WT melanoma cells were examined by low-temperature EPR to monitor oxidants formed in control and Mito-MGN-treated cells. Increased levels of oxidized aconitase (Acn) provides a biomarker for in vivo Mito-MGN effect on melanoma. S3=cluster from complex I and II; FeS=reduced iron sulfur, N4b=4Fe-4 S.

Example 3: Dose Limiting Effects of Mito-MGN in BRAF Inhibitor Resistant UACC-62-R Cells as Well as B16 BRAF WT Melanoma Cells The objective of this experiment is to use human melanoma xenograft and metastatic B16.F10 syngeneic orthograft models to investigate functional effects of Mito-MGN on tumor growth and metastasis in vivo. UACC or B16 tumor-bearing mice will be treated via intra-tumoral injection with 0.1, 0.5, 1, and 5 mg Mito-MGN. Immunohistochemistry will be used to investigate tumor mitophagy, proliferation, and cell death. BLI will be performed as illustrated in FIG. 17 and described in our prior publications (6, 10, 60, 77-79). BLI is based on the ATP-dependent, luciferase-catalyzed oxidation of luciferin accompanied by light emission proportional to the number of cancer cells (FIG. 16, Tumor size imaging). To monitor tumor size and ROS formation in vivo, UACC-62 and B16 melanoma cells will be engineered to express firefly luciferase. Because luc-catalyzed oxidation of luciferin requires ATP as a cofactor, this reaction can also be used to monitor changes in ATP level, when the tumor size is not a variable. Mice will be imaged first for tumor size and again the next day for ATP, a few hours after administering Mito-MGN (FIG. 16, Bioenergetic status imaging). To detect $H_2O_2$, HOCl, and $ONOO^-$ ROS, we will use PCL-1, a small-molecule cell-permeable probe that upon oxidation, yields luciferin in situ that is further oxidized in luciferase-transfected tumor cells to produce luminescence (FIG. 16, ROS imaging). Luciferin and PCL-1 are cleared within hours, so they can be used sequentially after 24 h (75).

Figure 15:
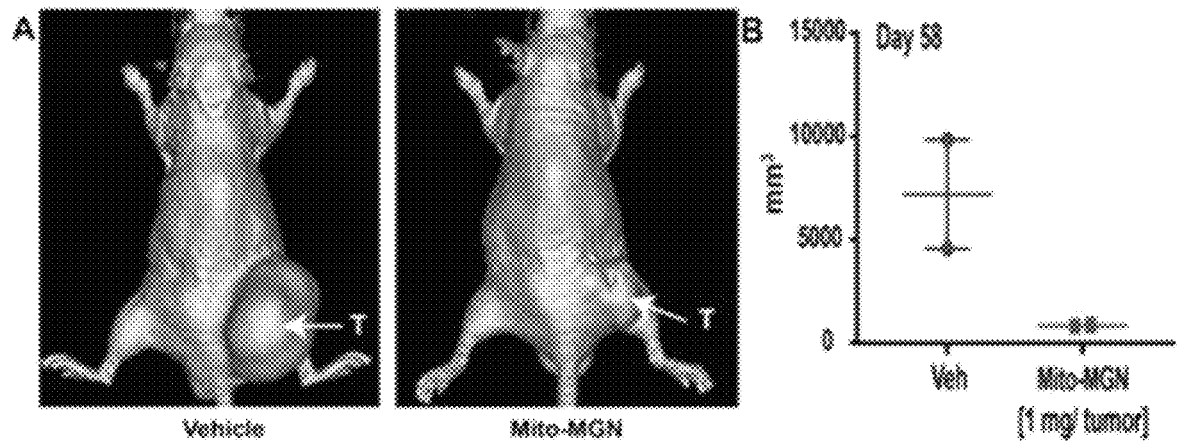
FIG. 15 shows computed tomography (CT) imaging of melanoma in control and Mito-MGN treated mice. (A) Representative μCT images on day 58 from UACC-62-WT xenographed (T=tumor) mice treated twice a week with vehicle (left) or 1 mg Mito-MGN (right). Data representative of 2 mice per group. (B) Quantification of tumor volume ($mm^3$) measured using calipers ex vivo on day 58.

Side-by-side experiments contrasting Mito-MGN effects on WT and BRAF resistant human xenograft and murine B16.F0, B16.F1, and B16.F10 melanoma progression will be completed. Mice will be randomly assigned to either Mito-MGN or vehicle treatment groups immediately after tumor cell inoculation. Tumor size will be measured weekly using BLI as we have shown previously (10, 60, 77-80), or using µCT as shown in FIG. 15. Imaging and histopathology will be completed by laboratory personnel blinded to the treatment conditions. Each group will comprise 4-6 mice and be repeated in 2-3 replicate studies to ensure sufficient statistical power. For example, a cumulative group size of 12 mice will provide 80% power to detect a difference of 1.27 radiance luminescence units (6.57 to 5.30), as calculated from our pilot studies and analyzed with a one-way ANOVA and a Tukey's multi-comparison test ($\alpha$ set at 0.05). Melanoma has a slightly higher incidence in men relative to women (1, 2), so our preclinical studies will include equal numbers of male and female mice.

Example 4: In Vivo Tumor Progression in Mito-MGN Treated Melanoma and Stimulation of ROS In Vivo Human UACC-62 xenografted SCID mice or B16 cells engrafted to C57BL/6 mice will be treated 3 times per week with 0.1, 0.5, 1, and 5 mg intratumoral doses of Mito-MGN. These doses were rationally selected based on the in vitro data and our prior reports using other mitochondria-targeted agents (8, 10, 17). Mice treated with vehicle will be the control. BLI and µCT and will be used for in vivo measurement of tumor growth and metastasis. At the completion of the experiment, mice will be sacrificed, and the primary tumor as well as the metastatic target organs (liver, lung, and brain) removed to measure overall tumor burden. Metastasis will be quantified by luminescence detection and wet weight of those organs. The incidence of metastasized tumors in control compared to treated mice will be recorded as a ratio of luminescent tumors in each organ and stated as overall tumor burden.

To quantify mitophagy in vivo, mice will be engrafted with mKeima transduced UACC-62 or B16 cells and treated with Mito-MGN. Tumors will be excised and phagosome acidification, as a measure of in vivo mitophagy, will be quantified using immunofluorescence microscopy (71) A portion of the excised tumor will be fixed in zinc formalin for histological analyses. Immunohistochemistry will be performed using anti-Ki67, anti-cleaved caspase-3, or anti-Parkin to visualize and quantify tumor cell growth, death, and mitophagy, respectively.

Ex vivo EPR analysis of mitochondrial complexes in mouse melanoma. To determine if Mito-MGN treatment stimulates ROS in vivo, low-temperature EPR spectroscopy will be employed Mitochondria exhibit multiple EPR signals, depending on the local redox environments of the individual mitochondrial complexes. EPR spectra (recorded at liquid helium temperatures) of mitochondria can be modeled as the sum of a set of simulated basis spectra from the redox centers of mitochondrial complexes I-IV and aconitase (49). FIG. 17 illustrates pilot EPR data of melanoma cells. The relative signal peaks indicate expression levels, the local and global redox states, and the integrity of the electron transport chain in control (black line) and Mito-MGN treated (red line) melanoma cells.

Melanoma tumors will be obtained from UACC xenograft or B16 engrafted mice after control and Mito-MGN treatment using an optimized sample harvesting procedure as described in our recent publication (49). Briefly, tumor tissues are flash frozen in liquid nitrogen, minced, and transferred to EPR tubes for measurements at liquid helium temperatures. A strong signal at $g=1.94$ indicates a reduced form of a $[2Fe-2S]^-$ center of mitochondrial complex I reflecting blocked electron transfer. The level of oxidatively inactivated mitochondrial aconitase is an established marker of mitochondrial oxidative stress (49). Aconitase is inactivated by superoxide-induced oxidation of the $[4Fe-4S]^{2+}$ cluster. The $[4Fe-4S]^+$ cluster of active aconitase is EPR silent, whereas superoxide-damaged aconitase has a $[3Fe-4S]^+$ cluster with characteristic EPR signals in the $g=2.03$ and 2.01 regions (49). Thus, increased ROS-mediated oxidative stress is indicated by increased aconitase (Acn) signal in the melanoma cells in vitro and tissue ex vivo.

Pilot studies indicate that three weekly treatment with Mito-Mag at 5 mg/kg resulted in little liver or kidney toxicity (Table 1)

TABLE 1

| | Toxicity | | |
|---|---|---|---|
| | ALT[IU/L] ref (22-77) | AP[IU/L] ref (45-222) | BUN[mg/dL] ref (12-28) |
| Control | 60.4 ± 22.2 | 52.2 ± 4.9 | 24.4 ± 1.6 |
| Mito-MGN | 58.7 ± 12.7 | 36.7 ± 10.8 | 24.5 ± 1.9 |

Serum levels assayed on day 19.
ALT: alanine transaminase; AP: alkaline phosphatase; BUN: Blood urea nitrogen.
Mean ± SE, n = 4-5

Example 5: Mito-MGN in Combination with BRAF Kinase Inhibitor Therapy

Multi-modal treatment approaches, including those targeting metabolism are an increasingly powerful strategy to treat cancer (28, 29). We will therefore examine the potential for Mito-MGN to provide additive or synergistic benefit to standard-of-care BRAF inhibitor chemotherapy. We hypothesize that the OXPHOS inhibitor Mito-MGN can synergize with the traditional BRAF inhibitor, vemurafenib, to abrogate melanoma progression in vivo. Tumor size and metastasis will be measured at study end (day 35). BRAF inhibitor sensitive B16 or UACC-62-WT melanoma engrafted mice will first be treated 3λ weekly starting on day 2 with Mito-MGN, at an initial 1 mg per tumor dose, followed by a weekly injection with BRAF inhibitor (500 nM) starting on day 3. Subsequent experiments will test a range of Mito-MGN doses from 0.1, 0.5 and 5 mg. Next, we will reverse the sequence of drug administration in which melanoma engrafted mice will first receive weekly vemurafenib starting on day 2 with Mito-MGN 3× per week starting on day 3.

We expect that Mito-MGN will abrogate the growth and progression of both BRAF inhibitor resistant and sensitive melanoma in vivo and block growth and metastasis across a range of non-metastatic (F0, F1) and metastatic (F10) B16 melanoma. Dual targeting of glycolysis using BRAF inhibitors plus Mito-MGN to inhibit OXPHOS is expected to strongly inhibit melanoma progression in vivo. The in vivo toxicity of Mito-MGN will be monitored using histopathologic assessment by a board-certified pathologist and serum quantification of hepatic, kidney, and cardiac biomarkers using veterinary assays. As proof of biological safety, an analogous compound, mito-honokiol, is well-tolerated, with no overt toxicity when administered at doses 20-times higher than those used for Mito-MGN (61). Prior reports effectively used catalase or superoxide dismutase overexpressing cells to scavenge cellular ROS/RNS (81). Changes in tumor cell metabolism may elicit alterations in accessory cells within the tumor microenvironment. Endothelial, fibroblast, and neuronal changes will be investigated using immunohistochemistry. While we expect the PCL-1 experiments to document changes in ROS within the tumor microenvironment, if we observe changes in those cells we would use a multiplex system to interrogate the secretome of Mito-MGN treated tumors. LCMS will be used to profile extracellular metabolites such as lactate or alanine. We will detect the major and minor products derived from Mito-B reaction with ROS/RNS.

Example 6: Analyze the Impact of Mito-MGN on Anti-Melanoma Immunity and Energy Metabolism of Tumor Reactive T Cells Melanoma is a variably immunogenic tumor with sensitivity to immune-targeted therapies (53, 82, 83). Melanoma lymphocyte infiltrate is highly associated with improved survival (84). Despite the prevalence of immune cells, anti-tumor immunity may be prevented by upregulation of checkpoint inhibitor ligands on tumor cells (85) that suppress anti-tumor effector CD8+ cytotoxic T lymphocytes (CTL) (85, 86). Paradoxically, while there are unproductive immune responses in the tumor microenvironment, there is an accumulation of tumor-reactive helper T cells and CTLs. As illustrated by Chen and Mellman (52), immune responses to cancer require effective infiltration of tumor reactive cells into the tumor and activated T cell-mediated killing of tumor cells. We propose that selectively targeting tumor mitochondria with Mito-MGN will promote anti-melanoma immune responses. Not to be bound by any theory, but we believe that Mito-MGN will promote anti-tumor immunity by inhibiting tumor cell OXPHOS and increasing ROS and mitophagy, which will in turn activate tumor killing independent of checkpoint protein expression.

Figure 18:
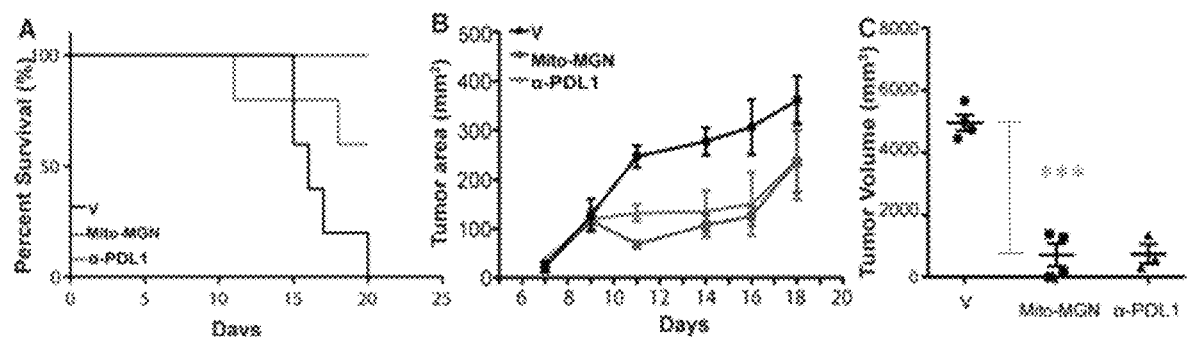
FIG. 18 demonstrates that Mito-MGN increases survival and decreases tumor size in B16-F10 melanoma. (A) Kaplan-Maier survival curves of B16-F10 engrafted mice treated on days 7, 9, 11, 14, 16, & 18 with Mito-MGN [1 mg] or with a-PD-L1 [250 μg]. (B) Tumor size (mm2) over time. (C) Tumor volume measured on day 19. Values are mean±SD, n=4 mice/group. ***, P≤0.001.
Figure 19:
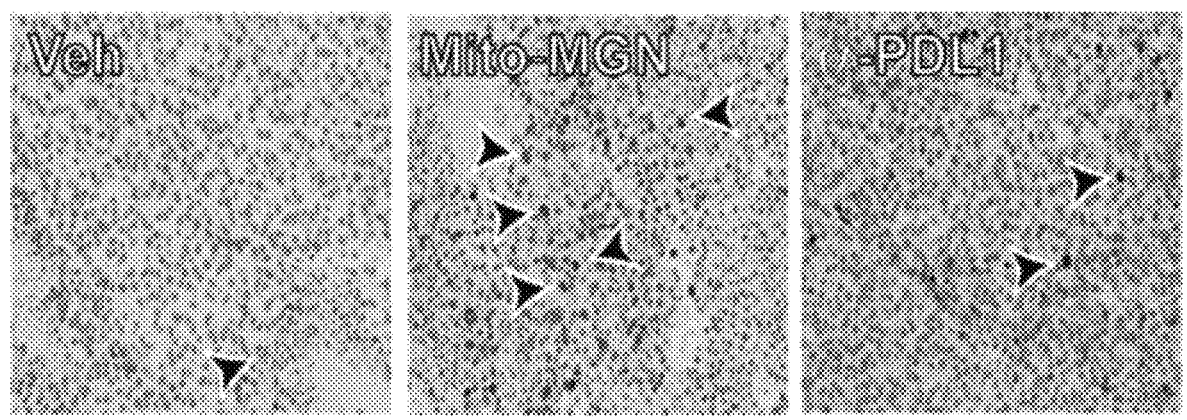
FIG. 19 demonstrates tumor infiltrating CD3+ T cells from vehicle (Veh), Mito-MGN, and anti-PD-L1 treated murine B16-F10 melanoma. T cells were detected using CD3 immunostaining (brown). Arrowheads highlight CD3+ T cells in melanoma (blue cells). Data representative of 4 separate mice.

In a pilot experiment, mice orthotopically engrafted with B16 F10 cells and treated with 1 mg/tumor Mito-MGN or 250 μg neutralizing anti-PD-L1 antibody showed increased survival (FIG. 18A) and decreased melanoma growth in vivo (FIG. 18). Mito-MGN efficiency was equal to anti-PD-L1 in abrogating tumor progression and size (FIG. 18B-C). Immunostaining of excised tumors with antibody against CD3, a pan-T cell marker, indicated that Mito-MGN and anti-PD-L1 each increased T cell levels compared to vehicle control tumors (FIG. 19), supporting our hypothesis that Mito-MGN is an immune stimulant that potently inhibits melanoma progression. Our data suggest the exciting potential for Mito-MGN to either synergize with checkpoint inhibitors such as PD-L1 or to improve immunotherapy independent of tumor checkpoint protein expression.

The B16 orthotopic syngeneic melanoma model will be used to investigate functional effects of Mito-MGN on immune cell proliferation and activation in melanoma. Flow cytometry will be used to comprehensively quantify lymphoid and myeloid cell populations within tumors of Mito-MGN treated and control mice. Immunohistochemistry will be used to visualize localization of intra-tumoral T cells and myeloid cells. To measure functional effects of Mito-MGN, apoptosis of melanoma cells cultured with tumor-reactive T cells will be measured using high-throughput IncuCyte cytotoxicity assays. Bioenergetic metabolism of immune cells will be measured using the Seahorse Extracellular Analyzer. Tumor cell levels of checkpoint inhibitor proteins will be measured by flow cytometry.

Effect of Mito-MGN on T cell activation and melanoma cell killing. To test the hypothesis that Mito-MGN enhances immune proliferation, we will first profile and quantify the lymphoid and myeloid cell subsets within melanomas of mice treated with 0.1, 0.5, 1, and 5 mg Mito-MGN or vehicle control. Mice treated with magnolol will serve as a separate control. Mice will be euthanized on days 7, 12, or 19 and bone marrow, spleen, and the tumor excised and immune cells dissociated. One half of the tumor will be fixed for immunohistochemical analysis and morphometric enumeration of immune cell localization. Immune cell subsets will be comprehensively profiled using a battery of lymphoid and myeloid markers from the remaining half of the tumor tissue (Table 1). Leukocyte proliferative capacity will be assessed by staining CD45+ cells for Ki67. Levels of tumor cell expressed PD-L1 will be measured from dissociated CD45− cells.

TABLE 1

Flow Cytometry

| Cell subset | Associated markers |
|---|---|
| Pan-leukocyte marker | CD45 |
| Activated CTL | CD3+, CD8+ CD69+ CD44+ granzyme B+ |
| Helper T cell | CD3+ CD4+ |
| Treg | CD3+ CD4+ *foxp3*+ |
| TAM | CD11b+ Ly6G+ Ly6C*low* |
| Granulocytic MDSC | CD11b+ Ly6G− Ly6C*high* |
| NK cell | CD3− NK1.1+ |

CT:, cytotixic T lymphocytes,
Treg, regulatory T cell,
TAM, Tumor-associated macrophage;
MDSC, myeloid-derived suppressor cell;
NK, Natural Killer;
*Italicized markers: intracellular*

Flow cytometry of isolated CD45+ immune cells will be used to test if Mito-MGN enhances T cell activation. T cell activation will be quantified by enumeration of Granzyme B, IFNγ, and PD-1 staining. To test the hypothesis that Mito-MGN increases tumor cell killing by infiltrating T cells, that portion of the tumor not used for flow cytometry will be digested to isolate and expand T infiltrating lymphocytes (TIL) ex vivo. TILs will be incubated 10:1 with anti-CD3/28 antibody-loaded and irradiated K562 artificial antigen presenting cells engineered to express CD32 and CD137L. TIL-K562 cells will be co-cultured in full growth medium supplemented with the proliferative cytokines IL2, IL7, and IL15. After 7-10 days in culture expanded TILs will be incubated at 5:1, 10:1, or 20.1 with $1 \times 10^5$ B16 cells and tumor cell killing measured using an IncuCyte caspase-3/7 assay. IFNγ ELISPOT will be measured as a second readout for activated T cell killing. T cells from non-tumor bearing mice will be a control.

Mito-MGN-induced ROS effects on T cell activation and melanoma cell killing. Our prediction is that mitochondrial ROS drives activation of tumor-reactive CD8+ CTLs. To test this, we will assay both T cell proliferation and activation using the IncuCyte in vitro imaging system. Naïve CD8− T cells will be isolated from the spleens of non-tumor bearing mice. TILs will be dissociated from melanoma-bearing mice. T cells will be expanded 7-10 days (see above) and incubated separated from B16 cells in a transwell (0.4 μm pore size). B16 cells will be treated with anti-proliferative doses of Mito-MGN or remain untreated as a control. Mitochondrial ROS (e.g., $H_2O2$) will be quenched by pretreating melanoma with catalase, PEG-catalase, or SOD mimetics prior to the addition of TILs to the transwell insert (102). T cell proliferation in the melanoma co-culture will be enumerated every 6 h by measuring T cell confluence using the IncuCyte imager.

Effector T cells use aerobic glycolysis while memory T cells rely on OXPHOS (88, 103). Activators of AMPK and inhibitors of mTORC1 signaling stimulate effector T cells (104). The dynamic bioenergetic metabolism of T cells may impact mitochondrial membrane potential (105). Thus, it is possible that Mito-MGN activates CTLs by inhibiting OXPHOS metabolic reprogramming. As we have done for normal and cancer epithelial cells, we will ascertain the potential for Mito-MGN to directly affect T cells, using LCMS will quantify Mito-MGN localization, or in separate experiments, ATP levels, within naïve CD8+ T cells and TILs from melanoma tumors. Separate B16 cell cultures will be treated and assayed in parallel to directly compare Mito-MGN selectivity for these cells. Seahorse bioenergetic profiles will measure ECAR and OCR, while TMRE flow cytometry will be used to measure mitochondrial metabolism and membrane potential in Mito-MGN-treated naïve T cells and effector TILs. Lastly, we will expand melanoma TILs ex vivo with CD3 and CD28 antibodies in the presence or absence of titrated levels of Mito-MGN. Proliferation of T cells will be enumerated every 2 h using IncuCyte and confirmed using Ki67 flow cytometry. To examine the potential for Mito-MGN to increase anti-tumor functional effects, TILs will be expanded ex vivo and after 7 days co-incubated with B16 cells to measure tumor cytotoxicity using the caspase 3/7 assay as illustrated above.

Mito-MGN effects in combination with checkpoint blockade. While we hypothesize that Mito-MGN stimulates T cell proliferation into the tumor mass, it remains possible that cellular mechanisms within the tumor parenchyma functionally prevent tumor cell killing by CTLs, an in vivo caveat our in vitro killing assays may not detect. The interaction between programmed death (PD-1), a surface receptor expressed on activated T cells, and its ligand, PD-L1 on tumor cells, is responsible for evasion of immune surveillant cytotoxic T cells (106). Although PD-1 blockade has revolutionized treatment in melanoma, T cell exhaustion caused by mitochondrial dysfunction and decreased energy metabolism renders cancers resistant to checkpoint (82, 10[7]). We will test the hypothesis that Mito-MGN will reverse F cell exhaustion and work independently and/or cooperatively with checkpoint inhibitors such as anti-PD-L1 in anti-melanoma immune responses. Initial experiments will group mice into Mito-MGN alone, anti-PD-L1 antibody at 250 μg only, or combinations of Mito-MGN with anti-PD-L1 treatment arms. The negative control groups will receive vehicle or 250 μg isotype control antibody. Mito-MGN will be administered three times per week by intra-tumoral injection starting on day 1 post-implantation while anti-PD-L1 will be administered on days 7, 11, and 16. The rationale for this initial treatment sequence is that we believe Mito-MGN will increase T cell proliferation and/or infiltration prior to blocking the suppressive effects mediated by PD-L1 blockade. Experiments reversing the sequence, with anti-PD-L1 treatment preceding the OXPHOS inhibitor will also be completed. Tumor wet weights and metastasis will be measured, and the tumor processed for flow cytometry. EPR will also be performed to assess metabolic reprogramming, as assessed by an increase in oxidized Acn signal (shown in FIG. 17).

We predict that Mito-MGN will increase levels of T cells throughout the melanoma tumor mass. Levels of PD-L1 on the tumors may diminish with Mito-MGN treatment (92). While not expected, if CD8+ T cell proliferation remains unchanged upon treatment, we would shift our attention to the effects of Mito-MGN on myeloid cells or natural killer cells. Indeed, because OXPHOS supports the differentiation of regulatory T cells and suppressive myeloid cells, we expect our immune profile analysis to detect decreases in both of those suppressive cell populations. Other checkpoint inhibitor antibodies against CTLA-4 or PD-1 expressed on immune cell subsets would be a viable complement for the proposed checkpoint inhibitor experiments (25). In vivo monitoring of T cell-cancer interactions will utilize our published intravital microscopy approach to visualize and quantify TIL movement in the melanoma microenvironment in real time, using Imaris software to identify and track individual TILs and calculate speed and contact time with melanoma cells (108-111). It is also possible that any elevation in T cells within the tumor may reflect Mito-MGN stimulating the mobilization of tumor reactive, as well as non-tumor reactive, T cells, into the peripheral blood, where they can then traffic into the melanoma tumor. To assess this potential. we will use flow cytometry to quantify T cells within the peripheral blood and, use IFNγ ELISPOT to determine the tumor reactivity of any circulating T cells. Experiments will be repeated in $RAG^{-/-}$-mice that lack T and B cells to rigorously resolve if the therapeutic effects of Mito-MGN are T cell mediated. To assess the potential for Mito-MGN to increase TILs by stimulating T cell migration and tumor infiltration, we will use $CXCR3^{-/-}$ mice to disrupt T cell chemotaxis. Autophagy plays a role in down-regulating tumor immune suppression in myeloid-derived suppressor cells or suppressive tumor-associated macrophages, a potential we fully expect our immune profiling to detect. If myeloid cell populations are affected by Mito-MGN, we would use flow cytometry to measure their activation and cell culture suppression assays to investigate functional changes. Organoid-T cell co-culture systems show increasing utility and provide an approach with which to examine tumor-immune interactions in a more physiologically relevant microenvironment. We have recently established a patient-derived organoid biomimetic system in pancreatic cancer (112) and envision future studies using this approach to examine ROS and mitophagy interactions between melanoma and reactive T cells (113, 114).

BIBLIOGRAPHY

1. Batus M, Waheed S, Ruby C, Petersen L, Bines S D. Kaufman H L. 2013. Optimal management of metastatic melanoma: current strategies and future directions. *Am J Clin Dermatol* 14:179-94
2. Miller K D, Siegel R L, Lin C C, Mariotto A B, Kramer J L, Rowland J H, Stein K D, Alteri R, Jemal A. 2016. Cancer treatment and survivorship statistics, 2016. *CA Cancer J Clin* 66: 271-89
3. Domingues B, Lopes J M, Soares P, Populo H. 2018. Melanoma treatment in review. *Immuntotargets Ther* 7: 35-49
4. Tsao H, Goel V, Wu H, Yang G, Haluska F G 2004. Genetic interaction between NRAS and BRAF mutations and PTEN/MMAC1 inactivation in melanoma. *J Invest Dermatol* 122: 337-41
5. Abildgaard C, Dahl C, Basse A L, Ma T, Guldberg P. 2014. Bioenergetic modulation with dichloroacetate reduces the growth of melanoma cells and potentiates their response to BRAFV600E inhibition. *J Transl Med* 12: 247
6. Cheng G, Zielonka J, Dranka B P, McAllister D, Mackinnon A C, Jr., Joseph J, Kalyanaraman B. 2012. Mitochondria-targeted drugs synergize with 2-deoxyglucose to trigger breast cancer cell death. *Cancer Res* 72: 2634-44
7. Cheng G, Zielonka J, McAllister D M, Mackinnon A C, Jr., Joseph J, Dwinell M B, Kalyanaraman B. 2013. Mitochondria-targeted vitamin E analogs inhibit breast cancer cell energy metabolism and promote cell death. *BMC. Cancer* 13: 285
8. Cheng G, Zielonka J, McAllister D, Tsai S, Dwinell M B, Kalyanaraman B. 2014. Profiling and targeting of cellular bioenergetics. inhibition of pancreatic cancer cell proliferation. *Br. J. Cancer* 1111: 85-93
9. Cheng G. Zielonka J, McAllister D, Hardy M, Ouari O, Joseph J, Dwinell M B, Kalyanaraman B. 2015. Antiproliferative effects of mitochondria-targeted cationic antioxidants and analogs: Role of mitochondrial bioenergetics and energy-sensing mechanism. *Cancer Lett* 365: 96-106
10. Cheng G, Zielonka J, Ouari O, Lopez M, McAllister D, Boyle K, Barrios C S, Weber J J, Johnson B D, Hardy M, Dwinell M B, Kalyanaraman B. 2016. Mitochondria-Targeted Analogues of Metformin Exhibit Enhanced Antiproliferative and Radiosensitizing Effects in Pancreatic Cancer Cells. *Cancer Res* 76: 3904-15
11. Kalyanaraman B, Cheng G, Hardy M, Ouari O, Lopez M, Joseph J, Zielonka J, Dwinell M B. 2018. A review of the basics of mitochondrial bioenergetics, metabolism, and related signaling pathways in cancer cells: Therapeutic targeting of tumor mitochondria with lipophilic cationic compounds *Redox Biol* 14: 316-27
12. Boyle K A, Van Wickle J, Hill R B, Marchese A, Kalyanaraman B, Dwinell M B. 2018. Mitochondria-targeted drugs stimulate mitophagy and abrogate colon cancer cell proliferation. *J Biol Chem* 293: 14891-904
13. Nadakavukaren K K, Nadakavukaren J J, Chen L B. 1985. Increased rhodamine 123 uptakeby carcinoma cells. *Cancer Res* 45: 6093-9
14. Modica-Napolitano J S, Aprille J R. 1987. Basis for the selective cytotoxicity of rhodamine 123 *Cancer Res* 47: 4361-5
15. Hong S K, Starenki D, Wu P K, Park J I. 2017. Suppression of B-Raf(V600E) melanoma cell survival by targeting mitochondria using triphenyl-phosphonium-conjugated nitroxide or ubiquinone. *Cancer Bio Ther* 18: 106-14
16. Smith R A, Adlam V J, Blaikie F H, Manas A R, Porteous C M, James A M, Ross M F, Logan A. Cocheme H M, Trnka J, Prime T A, Abakumova I, Jones B A, Filipovska A, Murphy N P. 2008. Mitochondria-targeted antioxidants in the treatment of disease. *Ann. N. Y. Acad. Sci* 1147: 105-11
17. Cheng G, Lopez M, Zielonka J, Hauser A D, Joseph J, McAllister D, Rowe J J, Sugg S L, Williams C L, Kalyanaraman B. 2011. Mitochondria-targeted nitroxides exacerbate fluvastatin-mediated cytostatic and cytotoxic effects in breast cancer cells. *Cancer Biol. Ther* 12: 707-17
18. Mukhopadhyay P, Horvath B, Zsengeller Z, Batkai S, Cao Z, Kechrid M, Holovac E, Erdelyi K. Tanchian G, Liaudet L, Stillman I E, Joseph J, Kalyanaraman B, Pacher P. 2012. Mitochondrial reactive oxygen species generation triggers inflammatory response and tissue injury associated with hepatic ischemia-reperfusion: Therapeutic potential of mitochondrially targeted antioxidants *Free Radic. Biol. Med* 53: 1123-38
19. Chandran K, Aggarwal D, Migrino R Q, Joseph J, McAllister D. Konorev E A, Antholine W E, Zielonka J, Srinivasan S, Avadhani N G, Kalyanaraman B. 2009. Doxorubicin inactivates myocardial cytochrome c oxidase in rats: cardioprotection by Mito-Q. *Biophys. J*96: 1388-98
20. Gide T N, Wilmott J S, Scolyer R A, Long G V. 2018. Primary and Acquired Resistance to Immune Checkpoint Inhibitors in Metastatic Melanoma. *Clin Cancer Res* 24: 1260-70
21. Vazquez F, Lim J H, Chim H, Bhalla K, Girnun G, Pierce K, Clish C B, Granter S R, Widlund H R, Spiegelman B M, Puigserver P. 2013. PGClalpha expression defines a subset of human melanoma tumors with increased mitochondrial capacity and resistance to oxidative stress. *Cancer Cell* 23: 287-301

22. Roesch A, Vultur A, Bogeski I, Wang H, Zimmermann K M, Speicher D, Korbel C, Laschke M W, Gimotty P A, Philipp S E, Krause E, Patzold S, Villanueva J, Krepler C, Fukunaga-Kalabis M, Hoth M, Bastian B C, Vogt T, Herlyn M. 2013. Overcoming intrinsic multidrug resistance in melanoma by blocking the mitochondrial respiratory chain of slow-cycling JARIDIB(high) cells. *Cancer Cell* 23:811-25

23. Hardeman K N, Peng C, Paudel B B, Meyer C T, Luong T, Tyson D R, Young J D, Quaranta V, Fessel J P. 2017. Dependence On Glycolysis Sensitizes BRAF-mutated Melanomas For Increased Response To Targeted BRAF Inhibition. *Sci Rep* 7: 42604

24. Haq R, Shoag J, Andreu-Perez P, Yokoyama S, Edelman H-Rowe G C, Frederick D T, Hurley A D, Nellore A, Kung A L, Wargo J A, Song J S, Fisher D E, Arany Z, Widlund H R 2013. Oncogenic BRAF regulates oxidative metabolism via PGClalpha and MITF. *Cancer Cell* 23: 302-15

25. Bengsch F, Knoblock D M, Liu A, McAllister F. Beatty G L. 2017. CTLA-4/CD80 pathway regulates T cell infiltration into pancreatic cancer. *Cancer Immunol Immunother* 66: 1609-17

26. Molina J R, Sun Y, Protopopova M, Gera S, Bandi M, Bristow C, McAfoos T, Morlacchi P, Ackroyd J, Agip A A, AI-Atrash G, Asara J, Bardenhagen J, Carrillo C C, Carroll C, Chang E, Ciurea S, Cross J B, Czako B, Deem A, Daver N, de Groot J F, Dong J W, Feng N, Gao G, Gay J, Do M G, Greer J, Giuliani V, Han J, Han L, Henry V K, Hirst J, Huang S, Jiang Y, Kang Z, Khor T, Konoplev S, Lin Y H, Liu G, Lodi A, Lofton T, Ma H, Mahendra M, Matre P, Mullinax R, Peoples M, Petrocchi A, Rodriguez-Canale J, Serreli R, Shi T, Smith M, Tabe Y, Theroff J, Tiziani S, Xu Q, Zhang Q, Muller F, DePinho R A, Toniatti C, Draetta G F, Heffernan T P, Konopleva M, Jones P, Di Francesco M E, Marszalek J R. 2018. An inhibitor of oxidative phosphorylation exploits cancer vulnerability. *Nat Med* 24: 1036-46

27. Weinberg F, Hamanaka R, Wheaton W W, Weinberg S, Joseph J, Lopez M, Kalyanaraman B, Mutlu G M, Budinger G R, Chandel N S. 2010. Mitochondrial metabolism and ROS generation are essential for Kras-mediated tumorigenicity. *Proc. Natl. Acad Sci. U. S A* 107:8788-93

28. Luengo A, Gui D Y, Vander Heiden M G. 2017. Targeting Metabolism for Cancer Therapy. *Cell Chem Bio/*24: 1161-80

29. Vander Heiden M G, DeBerardinis R J. 2017. Understanding the Intersections between Metabolism and Cancer Biology. *Cell* 168: 657-69

30. Weinberg S E, Chandel N S. 2015. Targeting mitochondria metabolism for cancer therapy *Nat Chem Biol* 11: 9-15

31. Zielonka J, Kalyanaraman B. 2018. Small-molecule luminescent probes for the detection of cellular oxidizing and nitrating species. *Free Radic Biol Med* 128: 3-22

32. Sarrica A. Kirika N. Romeo M, Salmona M, Diomede L. 2018. Safety and Toxicology of Magnolol and Honokiol. *Planta Med* 84: 1151-64

33. Zielonka J, Joseph J, Sikora A, Hardy M. Ouari O, Vasquez-Vivar J, Cheng G, Lopez M, Kalyanaraman B 2017. Mitochondria-Targeted Triphenylphosphonium-Based Compounds: Syntheses, Mechanisms of Action, and Therapeutic and Diagnostic Applications. *Chem Rev* 117: 10043-120

34. Sena L A, Li S, Jairaman A, Prakriya M, Ezponda T, Hildeman D A, Wang C R, Schumacker P T. Licht J D, Perlman H, Bryce P J, Chandel N S. 2013. Mitochondria are required for antigen-specific T cell activation through reactive oxygen species signaling. *Immunity* 38: 225-36

35. Weinberg S E, Sena L A, Chandel N S. 2015. Mitochondria in the regulation of innate and adaptive immunity. *Immunity* 42: 406-17

36. Schlie K, Westerback A, DeVorkin L, Hughson L R, Brandon J M, MacPherson S, Gadawski I, Townsend K N, Poon V I, Elrick M A, Cote H C, Abraham N, Wherry E J, Mizushima N, Lum J J. 2015. Survival of effector $CD8^+$ T cells during influenza infection is dependent on autophagy. *J Immuniol* 194:4277-86

37. Chamoto K, Chowdhury P S, Kumar A, Sonomura K, Matsuda F, Fagarasan S, Honjo T. 2017. Mitochondrial activation chemicals synergize with surface receptor PD-1 blockade for T cell-dependent antitumor activity. *Proc Natl Acad Sci USA* 114: E761-e70

38. Hosios A M, Vander Heiden M G. 2018. The redox requirements of proliferating mammalian cells. *J Biol Chem* 293: 7490-8

39. Beier U H, Angelin A, Akimova T, Wang L, Liu Y, Xiao H1, Koike M A, Hancock S A, Bhatti T R, Han R, Jiao J, Veasey S C, Sims C A, Baur J A, Wallace D C, Hancock W W. 2015. Essential role of mitochondrial energy metabolism in Foxp3(+) T-regulatory cell function and allograft survival. *Faseb j* 29: 2315-26

40. Goffaux G, Hammami 1, Jolicoeur M. 2017. A Dynamic Metabolic Flux Analysis of Myeloid-Derived Suppressor Cells Confirms Immunosuppression-Related Metabolic Plasticity. *Sci Rep* 7: 9850

41. Le Bourgeois T, Strauss L, Aksoylar H I, Daneshmandi S, Seth P, Patsoukis N, Boussiotis V A. 2018. Targeting T Cell Metabolism for Improvement of Cancer Immunotherapy. *Front Oncol* 8: 237

42. Kaelin W G, Jr. 2005. The concept of synthetic lethality in the context of anticancer therapy. *Nat Rev Cancer* 5: 689-98

43. Brunen D, Bernards R. 2017. Drug therapy: Exploiting synthetic lethality to improve cancer therapy. *Nat Rev Clin Oncol* 14: 331-2

44. Gopal Y N, Rizos H, Chen G, Deng W, Frederick D T, Cooper Z A, Scolyer R A, Pupo G, Komurov K, Sehgal V, Zhang J, Patel L, Pereira C G, Broom B M, Mills G B, Ram P. Smith P D, Wargo J A, Long G V, Davies M A. 2014. Inhibition of mTORC1/2 overcomes resistance to MAPK pathway inhibitors mediated by PGClalpha and oxidative phosphorylation in melanoma. *Cancer Res* 74: 7037-47

45. Schockel L, Glasauer A, Basit F, Bitschar K, Truong H, Erdmann G, Algire C, Hagebarth A, Willems P H, Kopitz C, Koopman W J, Heroult M. 2015. Targeting mitochondrial complex 1 using BAY 87-2243 reduces melanoma tumor growth. *Cancer Metab* 3: 11

46. Liberman E A, Topaly V P, Tsotina L M, Jasaitis A A, Skulachev V P. 1969. Mechanism of coupling of oxidative phosphorylation and the membrane potential of mitochondria. *Nature* 222-1076-8

47. Lichtshtein D, Kaback H R, Blume A J. 1979. Use of a lipophilic cation for determination of membrane potential in neuroblastoma-glioma hybrid cell suspensions. *Proc Nad Acad Sci US A* 76:650-4

48. Hanahan D, Weinberg R A. 2011. Hallmarks of cancer: the next generation. *Cell* 144: 646-74

49. Cheng G, Zielonka M, Dranka B, Kumar S N, Myers C R, Bennett B, Garces A M, Dias Duarte Machado L G, Thiebaut D, Ouari O, Hardy M, Zielonka J, Kalyanaraman B. 2018. Detection of mitochondria-generated reactive oxygen species in cells using multiple probes and methods: Potentials, pitfalls, and the future. *J Biol Chem* 293: 10363-80
50. Kalyanaraman B, Cheng G. Zielonka J, Bennett B. 2018. Low-Temperature EPR Spectroscopy as a Probe-Free Technique for Monitoring Oxidants Formed in Tumor Cells and Tissues: Implications in Drug Resistance and OXPHOS-Targeted Therapies. *Cell Biochem Biophys* 2018 Sep. 26. doi: 10.1007/s12013-018-0858-1. [Epub ahead of print]
51. Brahmer J R, Drake C G, Wollner I, Powderly J D, Picus J, Sharfman W H, Stankevich E, Pons A, Salay T $_M$, McMiller T L, Gilson M M, Wang C, Selby M, Taube J M, Anders R, Chen L, Korman A J, Pardoll D M, Lowy I, Topalian S L. 2010. Phase I study of single-agent anti-programmed death-1 (MDX-1106) in refractory solid tumors: safety. clinical activity, pharmacodynamics, and immunologic correlates. *J Clin Oncol* 28: 3167-75
52. Chen D S, Mellman 1. 2013. Oncology meets immunology: the cancer-immunity cycle. *Immunity* 39: 1-10
53. Hamid O, Robert C, Daud A, Hodi F S, Hwu W J, Kefford R, Wolchok J D, Hersey P, Joseph R W, Weber J S, Dronca R, Gangadhar T C, Patnaik A, Zarour H, Joshua A M, Gergich K, Elassaiss-Schaap J, Algazi A, Mateus C, Boasberg P, Tumeh P C, Chmielowski B, Ebbinghaus S W, Li X N, Kang S P, Ribas A. 2013. Safety and tumor responses with lambrolizumab (anti-PD-1) in melanoma. *N Engl J Med* 369: 134-44
54. Bryant K G, Chae Y C, Martinez R L, Gordon J C, Elokely K M, Kossenkov A V, Grant S, Childers W E, Abou-Gharbia M, Altieri D C. 2017. A Mitochondrial-targeted purine-based HSP90 antagonist for leukemia therapy. *Oncotarget* 8: 112184-98
55. Ozsvari B, Sotgia F, Lisanti M P. 2018. Exploiting mitochondrial targeting signal(s), TPP and bis-TPP, for eradicating cancer stem cells (CSCs). *Aging* (Albany N.Y.) 10: 229-40
56. Titova E, Shagieva G, Ivanova O, Domnina L, Domninskaya M, Strelkova O, Khromova N, Kopnin P. Chernyak B, Skulachev V, Dugina V. 2018. Mitochondria-targeted antioxidant SkQ1 suppresses fibrosarcoma and rhabdomyosarcoma tumour cell growth. *Cell Cycle* 17:1797-811
57. Hardy M, Zielonka J, Karoui H, Sikora A, Michalski R, Podsiadly R, Lopez M, Vasquez-Vivar J, Kalyanaraman B, Ouari O. 2018. Detection and Characterization of Reactive Oxygen and Nitrogen Species in Biological Systems by Monitoring Species-Specific Products. *Antioxid Redox Signal* 28: 1416-32
58. Nakamura K, Yoshikawa N, Yamaguchi Y, Kagota S, Shinozuka K, Kunitomo M. 2002. Characterization of mouse melanoma cell lines by their mortal malignancy using an experimental metastatic model. *Life Sci* 70: 791-8
59. Melnikova V O, Bolshakov S V, Walker C, Ananthaswamy H N. 2004. Genomic alterations in spontaneous and carcinogen-induced murine melanoma cell lines. *Oncogene* 23: 2347-56
60. Roy I, McAllister D, Gorse E, Dixon K, Piper C T, Zimmerman N P, Getschman A E, Tsai S, Engle D D, Evans D B, Volkman B F, Kalyanaraman B, Dwinell M B. 2015. Pancreatic Cancer Cell Migration and Metastasis Is Regulated by Chemokine-Biased Agonism and Bioenergetic Signaling. *Cancer Res* 75: 3529-42
61. Pan J Y L, Cheng G, Zielonka J, Zhang Q, Bajzikova M, Xiong D, Tsaih S-W, Hardy M, Flister M, Olsen C M, Wang Y, Vang O, Neuzil J, Myers C R, Kalyanaraman B, You M. 2018. Mitochondria-Targeted flonokiol Confers a Striking Inhibitory Effect on Lung Cancer via Inhibiting Complex I Activity. *iScience* 3: 192-207
62. Wood Z A, Poole L B, Karplus P A. 2003. Peroxiredoxin evolution and the regulation of hydrogen peroxide signaling. *Science* 300: 650-3
63. Cox A G, Winterbourn C C, Hampton M B. 2009. Mitochondrial peroxiredoxin involvement in antioxidant defence and redox signalling. *Biochem J* 425: 313-25
64. Myers C R. 2016. Enhanced targeting of mitochondrial peroxide defense by the combined use of thiosemicarbazones and inhibitors of thioredoxin reductase. *Free Radic Biol Med* 91: 81-92
65. Holmstrom K M, Finkel T. 2014. Cellular mechanisms and physiological consequences of redox-dependent signalling. *Nat Rev Mol Cell Biol* 15: 411-21
66. Andreyev A Y, Kushnareva Y E, Murphy A N, Starkov A A. 2015. Mitochondrial ROS Metabolism: 10 Years Later. *Biochemistry (Mosc)* 80: 517-31
67. Johnson L V, Walsh M L, Bockus B J, Chen L B. 1981. Monitoring of relative mitochondrial membrane potential in living cells by fluorescence microscopy. *J Cell Biol* 88: 526-35
68. Hardie D G, Ashford M L. 2014. AMPK: regulating energy balance at the cellular and whole body levels. *Physiology. (Bethesda.)* 29: 99-10$^7$
69. Allavena G, Boyd C, Oo K S, Maellaro E, Zhivotovsky B, Kaminskyy V O. 2016. Suppressed translation and ULKI degradation as potential mechanisms of autophagy limitation under prolonged starvation. *Autophagy* 12: 2085-97
70. Katayama H, Kogure T, Mizushima N, Yoshimori T, Miyawaki A. 2011. A sensitive and quantitative technique for detecting autophagic events based on lysosomal delivery. *Chem Biol* 18:1042-52
71. Sun N, Malide D, Liu J, Rovira, I I, Combs C A, Finkel T. 2017. A fluorescence-based imaging method to measure in vitro and in vivo mitophagy using mt-Keima. *Nat Protoc* 12: 1576-87
72. Das S, Alhasson F, Dattaroy D, Pourhoseini S, Seth R K, Nagarkatti M, Nagarkatti P S, Michelotti G A, Diehl A M, Kalyanaraman B, Chatterjee S. 2015. NADPH Oxidase-Derived Peroxynitrite Drives Inflammation in Mice and Human Nonalcoholic Steatohepatitis via rLR4-Lipid Raft Recruitment. *Am J Pathol* 185: 1944-57
73. Chandrashekaran V, Seth R K, Dattaroy D, Alhasson F, Ziolenka J, Carson J, Berger F G, Kalyanaraman B, Diehl A M, Chatterjee S. 2017. HMGBI-RAGE pathway drives peroxynitrite signaling-induced IBD-like inflammation in murine nonalcoholic fatty liver disease. *Redox Biol* 13:8-19
74. Deng J, Wang K, Wang M, Yu P, Mao L. 2017. Mitochondria Targeted Nanoscale Zeolitic Imidazole Framework-90 for ATP Imaging in Live Cells. *J Am Chem Soc* 139: 5877-82
75. Van de Bittner G C, Dubikovskaya E A, Bertozzi C R, Chang C J. 2010. In vivo imaging of hydrogen peroxide production in a murine tumor model with a chemoselective bioluminescent reporter. *Proc Nat Acad Sci USA* 107: 21316-21
76. Zielonka J, Podsiadly R, Zielonka M, Hardy M, Kalyanaraman B. 2016. On the use of peroxy-caged luciferin (PCL-1) probe for bioluminescent detection of inflammatory oxidants in vitro and in vivo—Identification of reaction intermediates and oxidant-specific minor products. *Free Radic Bio/Med* 99: 32-42

77. Wendt M K, Cooper A N, Dwinell M B. 2008. Epigenetic silencing of CXCL12 increases the metastatic potential of mammary carcinoma cells. *Oncogene* 27: 1461-71
78. Drury L J, Ziarek J J, Gravel S, Veldkamp C T, Takekoshi T, Hwang S T, Heveker N, Volkman B F, Dwinell M B. 2011. Monomeric and dimeric CXCL12 inhibit metastasis through distinct CXCR4 interactions and signaling pathways. *Proc. Natl. Acad. Sci. U. S A* 108: 17655-60
79. Roy I, Zimmerman N P, Mackinnon A C, Tsai S, Evans D B, Dwinell M B. 2014. CXCL12 chemokine expression suppresses human pancreatic cancer growth and metastasis. *PloS. ONE* 9: e90400
80. Wendt M K, Drury L J, Vongsa R A, Dwinell M B. 2008. Constitutive CXCL12 expression induces anoikis in colorectal carcinoma cells. *Gastroenterology* 135: 508-17
81. Brandt K E, Falls K C, Schoenfeld J D, Rodman S N, Gu Z, Zhan F, Cullen J J, Wagner B A, Buettner G R, Allen B G, Berg D J, Spitz D R, Fath M A. 2018. Augmentation of intracellular iron using iron sucrose enhances the toxicity of pharmacological ascorbate in colon cancer cells. *Redox Biol* 14: 82-7
82. Gajewski T F. 2006. Identifying and overcoming immune resistance mechanisms in the melanoma tumor microenvironment. *Clin Cancer Res* 12: 2326s-30s
83. Hodi F S, O'Day S J, McDermott D F, Weber R W, Sosman J A, Iiaanen J B, Gonzalez R, Robert C, Schadendorf D, Hassel J C, Akerley W, van den Eertwegh A J, Lutzky J, Lorigan P, Vaubel J M, Linette G P, Hogg D, Ottensmeier C H, Lebbe C, Peschel C, Quirt I, Clark J I, Wolchok J D, Weber J S, Tian J, Yellin M J, Nichol G M, Hoos A, Urba W J. 2010. Improved survival with ipilimumab in patients with metastatic melanoma. *N Engl J Med* 363: 711-23
84. Mihm M C, Jr., Clemente C G, Cascinelli N. 1996. Tumor infiltrating lymphocytes in lymph node melanoma metastases: a histopathologic prognostic indicator and an expression of local immune response. *Lab Invest* 74: 43-7
85. Chen D S, Mellman I. 2017. Elements of cancer immunity and the cancer-immune set point. *Nature* 541: 321-30
86. Gajewski T F, Schreiber H, Fu Y X. 2013. Innate and adaptive immune cells in the tumor microenvironment. *Nat Immunol* 14: 1014-22
87. Pearce E L. Walsh M C, Cejas P J, Harms G M, Shen H, Wang L S, Jones R G, Choi Y. 2009. Enhancing C D8 T-cell memory by modulating fatty acid metabolism. *Nature* 460: 103-7
88. Gubser P M, Bantug G R, Razik L, Fischer M, Dimeloe S, Hoenger G, Durovic B, Jauch A, Hess C. 2013. Rapid effector function of memory $CD8^+$ T cells requires an immediate-early glycolytic switch. *Nat Immunol* 14: 1064-72
89. Eikawa S, Nishida M, Mizukami S, Yamazaki C, Nakayama E, Udono H. 2015. Immune-mediated antitumor effect by type 2 diabetes drug, metformin. *Proc Natl Acad Sci USA* 112:1809-14
90. Pereira F V, *Melo* ACL, Low J S, de Castro I A, Braga T T, Almeida D C, Batista de Lima A G U, Hiyane M I, Correa-Costa M, Andrade-Oliveira V, Origassa C S T, Pereira R M, Kaech S M, Rodrigues E G, Camara N O S 2018. Metformin exerts antitumor activity via induction of multiple death pathways in tumor cells and activation of a protective immune response. *Oncotarget* 9: 25808-25
91. Li L, Wang L, Li J, Fan Z, Yang L, Zhang Z, Zhang C, Yue D, Qin G, Zhang T, Li F, Chen X, Ping Y, Wang D, Gao Q, He Q, Huang L, Li H, Huang J, Zhao X, Xue W. Sun Z, Lu J, Yu J J, Zhao J, Zhang B, Zhang Y. 2018. Metformin-Induced Reduction of CD39 and CD73 Blocks Myeloid-Derived Suppressor Cell Activity in Patients with Ovarian Cancer. *Cancer Res* 78:1779-91
92. Cha J H, Yang W H, Xia W, Wei Y, Chan L C, Lim S O, Li C W, Kim T, Chang S S, Lee H H, Hsu J L, Wang H L, Kuo C W, Chang W C, Hadad S, Purdie C A, McCoy A M, Cai S, Tu Y, Litton J K, Mittendorf E A, Moulder S L, Symmans W F, Thompson A M, Piwnica-Worms H, Chen C H. Khoo K H, Hung M C. 2018. Metformin Promotes Antitumor Immunity via Endoplasmic-Reticulum-Associated Degradation of PD-L1. *Mol Cell* 71: 606-20.e7
93. Ziegler P K, Bollrath J, Pallangyo C K, Matsutani T, Canli O, De Oliveira T, Diamanti M A, Muller N, Gamrekelashvili J, Putoczki T, Horst D, Mankan A K, Oner M G, Muller S, Muller-Hocker J, Kirchner T, Slotta-Huspenina J, Taketo M M, Reinheckel T, Drose S, Lamer A C, Wels W S, Ernst M, Greten T F, Arkan M C, Korn T, Wirth D, Greten F R. 2018. Mitophagy in Intestinal Epithelial Cells Triggers Adaptive Immunity during Tumorigenesis. *Cell* 174: 88-101.e16
94. Ma X H, Piao S F, Dey S, McAfee Q, Karakousis G, Villanueva J, Hart L S, Levi S, Hu J, Zhang G, Lazova R, Klump V, Pawelek J M, Xu X, Xu W, Schuchter L M, Davies M A, Herlyn M, Winkler J, Koumenis C, Amaravadi R K. 2014. Targeting E R stress-induced autophagy overcomes BRAF inhibitor resistance in melanoma. *J Clin Invest* 124: 1406-17
95. Kaminski M M, Sauer S W, Kaminski M, Opp S, Ruppert T, Grigaravicius P, Grudnik P, Grone H J, Krammer P H, Gulow K. 2012. T cell activation is driven by an ADP-dependent glucokinase linking enhanced glycolysis with mitochondrial reactive oxygen species generation. *Cell Rep* 2: 1300-15
96. Puleston Di, Simon A K. 2014. Autophagy in the immune system. *Immunology* 141:1-8
97. Janji B, Viry E, Moussay E, Paggetti J, Arakelian T, Mgrditchian T, Messai Y, Noman M Z, Van Moer K, Iasmim M, Mami-Chouaib F, Berchem G, Chouaib S. 2016. The multifaceted role of autophagy in tumor evasion from immune surveillance. *Oncotarget* 7: 17591-607
98. Cunha L D, Yang M, Carter R, Guy C, Harris L, Crawford J C, Quarato G, Boada-Romero E, Kalkavan H, Johnson M D L, Natarajan S, Turnis M E, Finkelstein D. Opferman J T, Gawad C, Green D R. 2018. LC3-Associated Phagocytosis in Myeloid Cells Promotes Tumor immune Tolerance. *Cell* 75: 429-41
99. Dowling S D, Macian F. 2018. Autophagy and T cell metabolism. *Cancer Lett* 419: 20-6
100. Mocholi E, Dowling S D, Botbol Y, Gruber R C, Ray A K, Vastert S, Shafit-Zagardo B, Coffer P J, Macian F. 2018. Autophagy Is a Tolerance-Avoidance Mechanism that Modulates TCR-Mediated Signaling and Cell Metabolism to Prevent Induction of T Cell Anergy. *Cell Rep* 24: 1136-50
101. Wang J M, Deng X, Gong W, Su S. 1998. Chemokines and their role in tumor growth and metastasis. *J. Immunol. Methods* 220: 1-17
102. Owens K M, Aykin-Burns N, Dayal D, Coleman M C, Domann F E, Spitz D R. 2012. Genomic instability induced by mutant succinate dehydrogenase subunit D (SDHD) is mediated by $O2(-*)$ and $H_2O_2$. *Free Radic Biol Med* 52: 160-6
103. Buck M D, O'Sullivan D, Pearce E L. 2015. T cell metabolism drives immunity. *J Exp Med* 212: 1345-60

104. Araki K, Turner A P, Shaffer V O, Gangappa S, Keller S A, Bachmann M F, Larsen C P, Ahmed R. 2009. mTOR regulates memory CD8 T-cell differentiation. *Nature* 460: 108-12
105. Sukumar M, Liu J, Mehta G U, Patel S J, Roychoudhuri R, Crompton J G, Klebanoff C A, Ji Y, Li P, Yu Z. Whitehill G D, Clever D, Eil R L, Palmer D C, Mitra S, Rao M, Keyvanfar K, Schrump D S, Wang E, Marincola F M, Gattinoni L., Leonard W J, Muranski P, Finkel T, Restifo N P. 2016. Mitochondrial Membrane Potential Identifies Cells with Enhanced Sternness for Cellular Therapy. *Cell Metab* 23: 63-76
106. Zha Y, Blank C, Gajewski T F. 2004. Negative regulation of T-cell function by PD-1. *Crit Rev Immunol* 24: 229-37
107. Blank C, Kuball J, Voelkl S, Wiendl H, Becker B, Walter B, Majdic O, Gajewski T F, Theobald M, Andreesen R, Mackensen A. 2006. Blockade of PD-L1 (B7-H1) augments human tumor-specific T cell responses in vitro. *Int J Cancer* 119: 317-27
108. Zimmerman N P, Vongsa R A, Faherty S L, Salzman N H, Dwinell M B. 2011. Targeted intestinal epithelial deletion of the chemokine receptor CXCR4 reveals important roles for extracellular-regulated kinase-1/2 in restitution. *Lab Invesvt* 91: 1040-55
109. Hwang S, Zimmerman N P, Agle K A, Turner J R, Kumar S N, Dwinell M B. 2012. E-cadherin is critical for collective sheet migration and is regulated by the chemokine CXCL12 protein during restitution. *J. Biol. Chem* 287: 22227-40
110. Gropper Y, Feferman T, Shalit T, Salame T M, Porat Z, Shakhar G. 2017. Culturing CTLs under Hypoxic Conditions Enhances Their Cytolysis and Improves Their Anti-tumor Function. *Cell Rep* 20:2547-55
111. Bentolila N Y, Barnhill R L, Lugassy C, Bentolila L A. 2018. Intravital Imaging of Human Melanoma Cells in the Mouse Ear Skin by Two-Photon Excitation Microscopy. *Methods Mol Biol* 1755: 223-32
112. Tsai S, McOlash L, Palen K, Johnson B, Duris C, Yang Q, Dwinell M B, Hunt B, Evans D B, Gershan J, James M A. 2018 Development of primary human pancreatic cancer organoids, matched stromal and immune cells and 3D tumor microenvironment models. *BMC Cancer* 18: 335
113. Spoerri L, Beaumont K A, Anfosso A, Haass N K. 2017. Real-Time Cell Cycle Imaging in a 3D Cell Culture Model of Melanoma. *Methods Mol Biol* 1612:401-16
114. Muller I, Kulms D. 2018. A 3D Organotypic Melanoma Spheroid Skin Model. *J Vis Exp* 2018 May 18; (135). doi: 10.3791/57500.

We claim:

1. A mito-magnolol compound of:

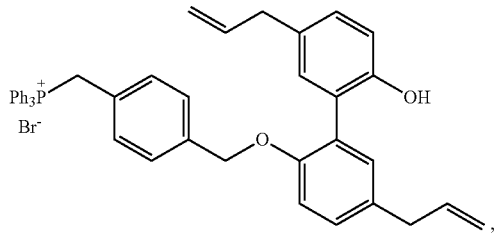

MitoPhen-MGN (i)

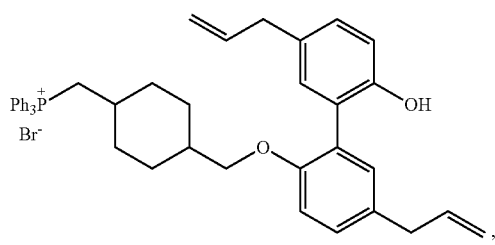

MitoCy-MGN (ii)

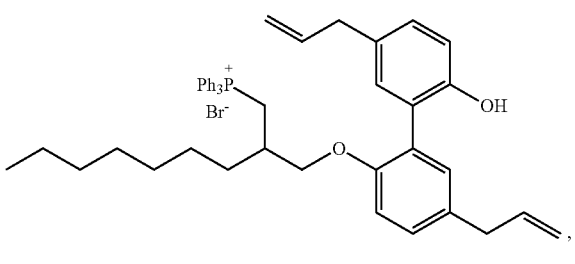

Mito$_{10}$-MGN2

(iii)

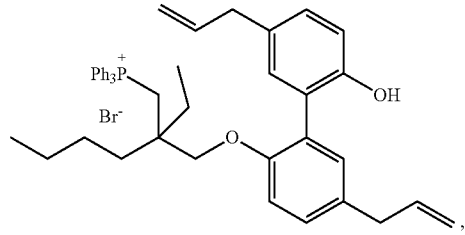

Mito$_9$-MGN2

(iv)

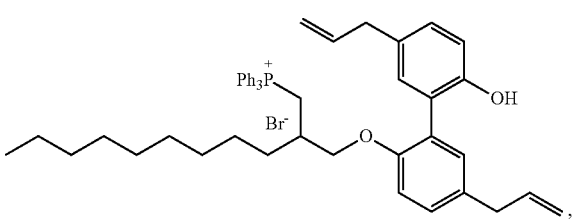

Mito$_{12}$-MGN2

(v)

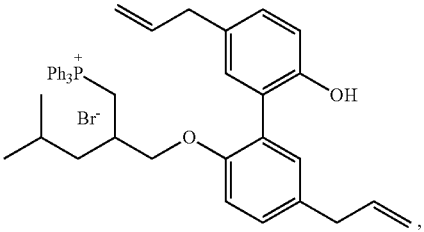

Mito$_7$-MGN2

(vi)

(vii)

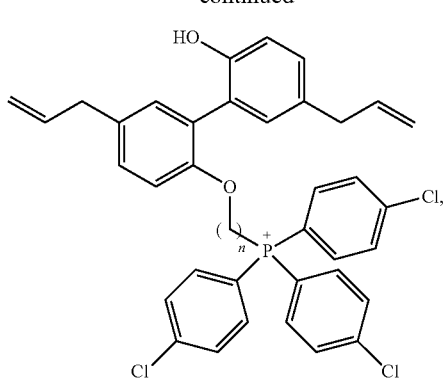

wherein n is an integer selected from 1-18, or (viii)

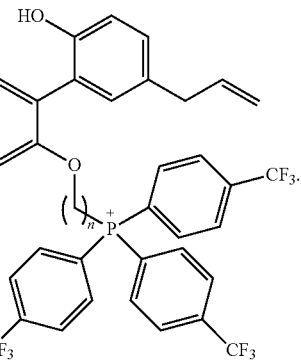

wherein n is an integer selected from 1-18.

2. A composition comprising the mito-magnolol compound of claim 1 and a pharmaceutically acceptable carrier.

3. A method of treating cancer in a subject having cancer comprising:
   administering the mito-magnolol compound of claim 1 in a therapeutically effective amount to treat the cancer, wherein the cancer is melanoma.

4. The method of claim 3, wherein the cancer is resistant to anti-cancer therapy.

5. The method of claim 4, wherein the anti-cancer therapy is a BRAF inhibitor.

6. The method of claim 4, wherein the anti-cancer therapy is a checkpoint inhibitor.

7. The method of claim 3, wherein the mito-magnolol compound is administered in combination with one or more additional anti-cancer therapies.

8. The method of claim 7, wherein the anti-cancer therapy is a BRAF inhibitor.

9. A method of reducing or inhibiting melanoma cancer cell growth in a subject having cancer, the method comprising:
   administering the mito-magnolol compound of claim 1 in a therapeutically effective amount to reduce or inhibit melanoma cancer cell growth.

10. The method of claim 9, wherein the mito-magnolol compound is administered in combination with one or more anti-cancer therapies.

11. A method of preventing or delaying resistance of a melanoma cancer to an anti-cancer therapy in a subject, the method comprising:
    administering the mito-magnolol compound of claim 1 in a therapeutically effective amount to prevent or delay resistance of the melanoma cancer to the anti-cancer therapy.

12. The method of claim 11, wherein the mito-magnolol compound is administered in combination with an anti-cancer therapy.

13. The method of claim 12, wherein the anti-cancer therapy is co-currently administered.

14. A method of increasing a T cell response to an anti-cancer therapy in a cancer patient, the method comprising administering the mito-magnolol compound of claim 1 in a therapeutically effective amount to increase the T cell response to the anti-cancer therapy, wherein the cancer is melanoma.

15. The method of claim 14, wherein the anti-cancer therapy is an inhibitor of an oncogenic kinase.

16. The method of claim 14, wherein the anti-cancer therapy is a checkpoint inhibitor.

17. The method of claim 14, wherein the mito-magnolol compound is administered in combination with one or more anti-cancer therapies.

18. A kit comprising at least one mito-magnolol compound of claim 1, a pharmaceutically acceptable carrier or diluent, and instructional material.

* * * * *

UNITED STATES PATENT AND TRADEMARK OFFICE
CERTIFICATE OF CORRECTION

PATENT NO. : 11,612,610 B2
APPLICATION NO. : 17/397672
DATED : March 28, 2023
INVENTOR(S) : Balaraman Kalyanaraman et al.

It is certified that error appears in the above-identified patent and that said Letters Patent is hereby corrected as shown below:

In the Specification

Column 4, Line 1, "comp und" should be --compound--.

Column 8, Line 59, "a-PD-L1" should be --α-PD-L1--.

Column 10, Line 51, "CF" should be --$CF_3$--.

Column 10, Line 52, "C(O)CHI" should be --$C(O)CH_3$--.

Column 11, Line 1, "mito-magnolo can" should be --mito-magnolol compound can--.

Column 16, Line 9, "(Imtinzi)" should be --(Imfinzi)--.

Column 17, Line 42, "40% NO" should be --40%--.

Column 19, Lines 63-64, "claims. 100%1 Example 1" should be
--claims.
      Example 1--.

Column 20, Line 27, "(611, m)" should be --(6H, m)--.

Column 20, Line 27, "(211, m)" should be --(2H, m)--.

Column 20, Line 44, "(I mmol)" should be --(1 mmol)--.

Column 20, Line 55, "(15H1, m)" should be --(15H, m)--.

Column 26, Line 31, "Milo-MGN" should be --Mito-MGN--.

Signed and Sealed this
Ninth Day of May, 2023

Katherine Kelly Vidal
*Director of the United States Patent and Trademark Office*

CERTIFICATE OF CORRECTION (continued)
U.S. Pat. No. 11,612,610 B2

Column 26, Line 31, "complex 1 activity" should be --complex I activity--.

Column 26, Line 36, "complex 1 activity" should be --complex I activity--.

Column 27, Line 32, "(IE)" should be --(HE)--.

Column 29, Line 3, "Chim 1-1" should be --Chim H--.

Column 29, Line 3, "Gimun G" should be --Girnun G--.

Column 29, Line 10, "Frederick Dr" should be --Frederick DT--.

Column 29, Line 11, "Song I S" should be --Song JS--.

Column 30, Line 19, "Gargon G" should be --Garçon G--.

Column 30, Line 37, "10.3389/timmu" should be --10.3389/fimmu--.

Column 30, Line 59, "(ICT)" should be --(μCT)--.

Column 33, Line 31, "3λ" should be --3x--.

Column 36, Line 29, "reverse F cell" should be --reverse T cell--.

Column 38, Line 22, "uptakeby" should be --uptake by--.

Column 39, Line 47, "Bio/24:" should be --Biol 24:--.

Column 40, Line 27, "Hammami 1" should be --Hammami I--.

Column 40, Line 54, "Tsotina L M" should be --Tsofina LM--.

Column 40, Line 61, "Nad Acad" should be --Natl Acad--.

Column 41, Line 19, "Mellman 1" should be --Mellman I--.

Column 42, Line 1, "flonokiol" should be --Honokiol--.

Column 42, Line 30, "ULKI" should be --ULK1--.

Column 42, Line 45, "rLR4-Lipid" should be --TLR4-Lipid--.

Column 42, Line 60, "Nat Acad" should be --Natl Acad--.

Column 43, Line 26, "Iiaanen JB" should be --Haanen JB--.

Column 44, Line 17, "Lamer AC" should be --Larner AC--.

Column 44, Line 36, "Puleston Di" should be --Puleston DJ--.

Column 44, Line 40, "Iasmim M" should be --Hasmim M--.

Column 45, Line 11, "Sternness" should be --Stemness--.

Column 45, Line 25, "Invesvt" should be --Invest--.